United States Patent
Liu et al.

(10) Patent No.: US 11,202,853 B2
(45) Date of Patent: *Dec. 21, 2021

(54) POROGEN COMPOSITIONS, METHODS OF MAKING AND USES

(71) Applicant: Allergan, Inc., Irvine, CA (US)

(72) Inventors: Futian Liu, Sunnyvale, CA (US); Nicholas J Manesis, Escondido, CA (US); Xiaojie Yu, Irvine, CA (US); Athene W. Chan, South San Francisco, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/850,981

(22) Filed: Apr. 16, 2020

(65) Prior Publication Data

US 2020/0237968 A1 Jul. 30, 2020

Related U.S. Application Data

(63) Continuation of application No. 14/960,075, filed on Dec. 4, 2015, now Pat. No. 10,624,997, which is a
(Continued)

(51) Int. Cl.
| | |
|---|---|
| *A61L 27/56* | (2006.01) |
| *B29C 41/14* | (2006.01) |
| *B29C 41/22* | (2006.01) |
| *A61L 28/00* | (2006.01) |
| *A61L 31/14* | (2006.01) |

(Continued)

(52) U.S. Cl.
CPC ............ *A61L 27/56* (2013.01); *A61L 24/001* (2013.01); *A61L 24/0036* (2013.01); *A61L 27/18* (2013.01); *A61L 27/20* (2013.01); *A61L 27/26* (2013.01); *A61L 27/34* (2013.01); *A61L 28/0034* (2013.01); *A61L 28/0053* (2013.01); *A61L 31/041* (2013.01); *A61L 31/042* (2013.01); *A61L 31/06* (2013.01); *A61L 31/10* (2013.01); *A61L 31/14* (2013.01); *A61L 31/146* (2013.01); *B29C 41/14* (2013.01);
(Continued)

(58) Field of Classification Search
None
See application file for complete search history.

(56) References Cited

U.S. PATENT DOCUMENTS

| | | |
|---|---|---|
| 2,762,476 A | 9/1956 | Gaylord et al. |
| 2,805,208 A | 9/1957 | Roche |

(Continued)

FOREIGN PATENT DOCUMENTS

| | | |
|---|---|---|
| CA | 2049377 | 3/1992 |
| CA | 2811975 | 11/2011 |

(Continued)

*Primary Examiner* — Peter A Salamon
(74) *Attorney, Agent, or Firm* — Nathan S. Smith; Sujohn Das; Morgan, Lewis & Bockius LLP

(57) ABSTRACT

The present specification discloses porogen compositions comprising a core material and shell material, methods of making such porogen compositions, methods of forming such porous materials using such porogen compositions, biocompatible implantable devices comprising such porous materials, and methods of making such biocompatible implantable devices.

19 Claims, 12 Drawing Sheets

Under-fused and over-fused porogens

Uniformly-fused porogens

Related U.S. Application Data continuation of application No. 13/631,091, filed on Sep. 28, 2012, now Pat. No. 9,205,577, which is a continuation-in-part of application No. 13/104,811, filed on May 10, 2011, now Pat. No. 8,685,296.

(60) Provisional application No. 61/333,599, filed on May 11, 2010.

(51) Int. Cl.

| | | |
|---|---|---|
| A61L 24/00 | (2006.01) | |
| A61L 27/18 | (2006.01) | |
| A61L 27/20 | (2006.01) | |
| A61L 27/26 | (2006.01) | |
| A61L 27/34 | (2006.01) | |
| A61L 31/04 | (2006.01) | |
| A61L 31/06 | (2006.01) | |
| A61L 31/10 | (2006.01) | |
| A61F 2/12 | (2006.01) | |

(52) U.S. Cl.
CPC ............... *B29C 41/22* (2013.01); *A61F 2/12* (2013.01); *A61L 2400/18* (2013.01); *Y10T 428/2989* (2015.01)

(56) References Cited

U.S. PATENT DOCUMENTS

| | | | |
|---|---|---|---|
| 3,189,921 A | 6/1965 | Pangman | |
| 3,293,663 A | 12/1966 | Cronin | |
| 3,366,975 A | 2/1968 | Pangman | |
| 3,558,768 A * | 1/1971 | Klippel | A61K 9/2063 |
| | | | 424/480 |
| 3,559,214 A | 2/1971 | Pangman | |
| 3,600,718 A | 8/1971 | Boone | |
| 3,665,520 A | 5/1972 | Perras | |
| 3,700,380 A | 10/1972 | Kitrilakis | |
| 3,852,832 A | 12/1974 | McGhan et al. | |
| 3,934,274 A | 1/1976 | Hartley | |
| 4,034,751 A | 7/1977 | Hung | |
| 4,157,085 A | 6/1979 | Austad | |
| 4,231,979 A | 11/1980 | White | |
| 4,237,237 A | 12/1980 | Jarre et al. | |
| 4,264,990 A | 5/1981 | Hamas | |
| 4,284,786 A * | 8/1981 | Kammerer | C07D 261/18 |
| | | | 514/903 |
| 4,298,997 A | 11/1981 | Rybka | |
| 4,298,998 A | 11/1981 | Naficy | |
| 4,329,385 A | 5/1982 | Banks | |
| 4,428,082 A | 1/1984 | Naficy | |
| 4,433,440 A | 2/1984 | Cohen | |
| 4,470,160 A | 9/1984 | Cavon | |
| 4,482,577 A | 11/1984 | Goldstein | |
| 4,499,211 A | 2/1985 | Walch | |
| 4,531,244 A | 7/1985 | Hamas | |
| 4,533,568 A | 8/1985 | McClinton et al. | |
| 4,568,559 A * | 2/1986 | Nuwayser | A61K 9/1647 |
| | | | 424/493 |
| 4,573,999 A | 3/1986 | Netto | |
| 4,584,324 A | 4/1986 | Bauman et al. | |
| 4,592,755 A | 6/1986 | Penton | |
| 4,608,396 A | 8/1986 | Bauman et al. | |
| 4,610,690 A | 9/1986 | Tiffany | |
| 4,636,213 A | 1/1987 | Pakiam | |
| 4,643,733 A | 2/1987 | Becker | |
| 4,647,618 A | 3/1987 | Bauman et al. | |
| 4,648,880 A | 3/1987 | Brauman | |
| 4,650,487 A | 3/1987 | Chaglassian | |
| 4,651,717 A | 3/1987 | Jakubczak | |
| 4,652,441 A * | 3/1987 | Okada | A61K 9/1647 |
| | | | 264/4.6 |
| 4,681,587 A | 7/1987 | Eberl | |
| 4,740,208 A | 4/1988 | Cavon | |
| 4,772,285 A | 9/1988 | Ksander | |
| 4,773,908 A | 9/1988 | Becker | |
| 4,773,909 A | 9/1988 | Chaglassian | |
| 4,790,848 A | 12/1988 | Cronin | |
| 4,795,464 A | 1/1989 | Eberl | |
| 4,803,025 A | 2/1989 | Brockmeyer | |
| 4,822,789 A * | 4/1989 | Yamaguchi | A61K 31/55 |
| | | | 514/211.07 |
| 4,828,560 A | 5/1989 | Heyler | |
| 4,832,686 A * | 5/1989 | Anderson | A61K 9/1647 |
| | | | 264/4.6 |
| 4,840,628 A | 6/1989 | Cavon | |
| 4,841,992 A | 6/1989 | Sasaki | |
| 4,859,383 A | 8/1989 | Dillon | |
| 4,859,712 A | 8/1989 | Cox | |
| 4,889,744 A | 12/1989 | Quaid | |
| 4,892,544 A * | 1/1990 | Frisch | A61F 2/06 |
| | | | 128/898 |
| 4,899,764 A | 2/1990 | Gauger | |
| 4,902,294 A | 2/1990 | Gosserez | |
| 4,906,423 A | 3/1990 | Frisch | |
| 4,936,858 A | 6/1990 | O'Keeffe | |
| 4,944,749 A | 7/1990 | Becker | |
| 4,944,750 A | 7/1990 | Cox | |
| 4,950,292 A | 8/1990 | Audretsch | |
| 4,955,907 A | 9/1990 | Ledergerber | |
| 4,955,909 A | 9/1990 | Ersek et al. | |
| 4,960,425 A | 10/1990 | Yan | |
| 4,965,430 A | 10/1990 | Curtis | |
| 4,969,899 A | 11/1990 | Cox | |
| 5,002,572 A | 3/1991 | Picha | |
| 5,007,929 A | 4/1991 | Quaid | |
| 5,007,940 A | 4/1991 | Berg | |
| 5,011,494 A | 4/1991 | von Recum et al. | |
| 5,022,942 A | 6/1991 | Yan et al. | |
| 5,026,394 A | 6/1991 | Baker | |
| 5,034,422 A | 7/1991 | Triolo et al. | |
| 5,035,249 A | 7/1991 | Sasaki | |
| 5,092,348 A | 3/1992 | Dubrul | |
| 5,092,882 A | 3/1992 | Lynn | |
| 5,104,409 A | 4/1992 | Baker | |
| 5,116,387 A | 5/1992 | Berg | |
| 5,128,088 A | 7/1992 | Shimomura et al. | |
| 5,135,959 A | 8/1992 | Hill | |
| 5,146,933 A | 9/1992 | Boyd | |
| 5,147,398 A | 9/1992 | Lynn | |
| 5,158,571 A | 10/1992 | Picha | |
| 5,158,573 A | 10/1992 | Berg | |
| 5,171,269 A | 12/1992 | Bark | |
| 5,185,297 A | 2/1993 | Park | |
| 5,204,024 A | 4/1993 | Onaka et al. | |
| 5,207,709 A | 5/1993 | Picha | |
| 5,219,361 A | 6/1993 | von Recum et al. | |
| 5,236,453 A | 8/1993 | Picha | |
| 5,236,454 A | 8/1993 | Miller | |
| 5,236,457 A | 8/1993 | Devanathan | |
| 5,246,454 A | 9/1993 | Peterson | |
| 5,279,826 A * | 1/1994 | Inamura | C07K 14/811 |
| | | | 424/117 |
| 5,282,856 A | 2/1994 | Ledergerber | |
| 5,296,069 A | 3/1994 | Robert | |
| 5,340,656 A | 8/1994 | Sachs et al. | |
| 5,348,788 A | 9/1994 | White | |
| 5,354,338 A | 10/1994 | Ledergerber | |
| 5,358,521 A | 10/1994 | Shane | |
| 5,376,117 A | 12/1994 | Pinchuk | |
| 5,383,929 A | 1/1995 | Ledergerber | |
| 5,437,824 A | 8/1995 | Carlisle | |
| 5,441,919 A | 8/1995 | Park | |
| 5,447,535 A | 9/1995 | Muller | |
| 5,455,100 A | 10/1995 | White | |
| 5,480,430 A | 1/1996 | Carlisle et al. | |
| 5,496,367 A | 3/1996 | Fisher | |
| 5,496,370 A | 3/1996 | Hamas | |
| 5,507,808 A | 4/1996 | Becker | |
| 5,522,896 A | 6/1996 | Prescott | |
| 5,525,275 A | 6/1996 | Iversen | |
| 5,534,023 A | 7/1996 | Henley | |
| 5,545,217 A | 8/1996 | Offray | |
| 5,545,220 A | 8/1996 | Andrews | |

(56) References Cited

U.S. PATENT DOCUMENTS

| | | | |
|---|---|---|---|
| 5,549,671 A | 8/1996 | Waybright | |
| 5,571,179 A | 11/1996 | Manders | |
| 5,575,987 A * | 11/1996 | Kamei | A61K 9/1647 264/4.1 |
| RE35,391 E | 12/1996 | Brauman | |
| 5,589,176 A | 12/1996 | Seare | |
| 5,594,091 A * | 1/1997 | Igari | A61K 9/1647 514/772.3 |
| 5,605,693 A | 2/1997 | Seare | |
| 5,607,473 A | 3/1997 | Weber-Unger | |
| 5,611,971 A * | 3/1997 | Maedera | A61K 9/1647 264/4.1 |
| 5,624,674 A | 4/1997 | Seare | |
| 5,630,843 A | 5/1997 | Rosenberg | |
| 5,630,844 A | 5/1997 | Dogan | |
| 5,653,755 A | 8/1997 | Ledergerber | |
| 5,658,330 A | 8/1997 | Carlisle | |
| 5,674,285 A | 10/1997 | Quaid | |
| 5,681,572 A | 10/1997 | Seare | |
| 5,776,159 A | 7/1998 | Young | |
| 5,779,734 A | 7/1998 | Ledergerber | |
| 5,798,065 A | 8/1998 | Picha | |
| 5,824,081 A | 10/1998 | Knapp | |
| 5,843,189 A | 12/1998 | Perouse | |
| 5,855,588 A | 1/1999 | Young | |
| 5,871,497 A | 2/1999 | Young | |
| 5,876,756 A * | 3/1999 | Takada | A61K 9/1647 264/4.6 |
| 5,895,423 A | 4/1999 | Becker et al. | |
| 5,935,164 A | 8/1999 | Iversen | |
| 5,961,552 A | 10/1999 | Iversen et al. | |
| 5,964,803 A | 10/1999 | Iversen et al. | |
| 5,965,076 A | 10/1999 | Banks | |
| 5,984,943 A | 11/1999 | Young | |
| 5,993,716 A | 11/1999 | Draenert | |
| 6,045,830 A * | 4/2000 | Igari | A61K 9/1647 424/426 |
| 6,071,309 A | 6/2000 | Knowlton | |
| 6,074,421 A | 6/2000 | Murphy | |
| 6,083,262 A | 7/2000 | Caravel | |
| 6,099,565 A | 8/2000 | Sakura | |
| 6,113,634 A | 9/2000 | Weber-Unger | |
| 6,113,941 A * | 9/2000 | Takada | A61K 9/1647 424/426 |
| 6,113,943 A * | 9/2000 | Okada | A61K 9/1647 424/423 |
| 6,117,455 A * | 9/2000 | Takada | A61K 9/1611 424/426 |
| 6,146,418 A | 11/2000 | Berman | |
| 6,183,514 B1 | 2/2001 | Becker | |
| 6,187,043 B1 | 2/2001 | Ledergerber | |
| 6,203,570 B1 | 3/2001 | Baeke | |
| 6,206,930 B1 | 3/2001 | Burg | |
| 6,214,045 B1 | 4/2001 | Corbitt, Jr. et al. | |
| 6,214,926 B1 | 4/2001 | Winn | |
| 6,291,456 B1 * | 9/2001 | Stein | C07D 311/16 514/233.5 |
| 6,315,796 B1 | 11/2001 | Eaton | |
| 6,331,562 B1 * | 12/2001 | Bhagwat | C07D 311/16 514/456 |
| 6,340,648 B1 | 1/2002 | Imura et al. | |
| 6,387,133 B1 | 5/2002 | Perouse | |
| 6,419,961 B1 * | 7/2002 | Igari | A61K 9/1647 424/426 |
| 6,432,138 B1 | 8/2002 | Offray | |
| 6,436,923 B1 * | 8/2002 | Bhagwat | C07D 209/44 514/213.01 |
| 6,464,726 B1 | 10/2002 | Heljenck | |
| 6,520,989 B1 | 2/2003 | Eaton | |
| 6,531,523 B1 | 3/2003 | Davankov | |
| 6,544,287 B1 | 4/2003 | Johnson et al. | |
| 6,593,322 B1 * | 7/2003 | Bhagwat | C07D 209/44 514/213.01 |
| 6,602,452 B2 | 8/2003 | Schuessler | |
| 6,605,116 B2 | 8/2003 | Falcon et al. | |
| 6,620,838 B1 * | 9/2003 | McKie | C07D 311/16 514/422 |
| 6,638,308 B2 | 10/2003 | Corbitt | |
| 6,673,285 B2 | 1/2004 | Ma | |
| 6,692,527 B1 | 2/2004 | Bellin et al. | |
| 6,755,861 B2 | 6/2004 | Nakao | |
| 6,802,861 B1 | 10/2004 | Hamas | |
| 6,811,570 B1 | 11/2004 | Gehl | |
| 6,818,673 B2 | 11/2004 | Ferguson | |
| 6,875,233 B1 | 4/2005 | Turner | |
| 6,881,226 B2 | 4/2005 | Corbitt | |
| 6,900,055 B1 | 5/2005 | Fuller | |
| 6,913,626 B2 | 7/2005 | McGhan | |
| 6,916,339 B1 | 7/2005 | Missana | |
| 6,921,418 B2 | 7/2005 | Ledergerber | |
| 6,932,840 B1 | 8/2005 | Bretz | |
| 6,993,406 B1 | 1/2006 | Cesarano, III | |
| 7,081,135 B2 | 7/2006 | Smith | |
| 7,081,136 B1 | 7/2006 | Becker | |
| 7,105,116 B2 | 9/2006 | Bellin et al. | |
| 7,169,180 B2 | 1/2007 | Brennan | |
| 7,192,450 B2 | 3/2007 | Brauker | |
| 7,244,270 B2 | 7/2007 | Lesh | |
| 7,309,232 B2 | 12/2007 | Rutherford et al. | |
| 7,323,208 B2 | 1/2008 | Ma | |
| 7,476,249 B2 | 1/2009 | Frank | |
| 7,520,896 B2 | 4/2009 | Benslimane | |
| 7,547,393 B2 | 6/2009 | Ramaswamy | |
| 7,625,405 B2 | 12/2009 | Purkait | |
| 7,632,228 B2 | 12/2009 | Brauker | |
| 7,632,291 B2 | 12/2009 | Stephens | |
| 7,641,688 B2 | 1/2010 | Lesh | |
| 7,645,475 B2 | 1/2010 | Prewett | |
| 7,758,788 B2 | 7/2010 | Job | |
| 7,867,061 B2 | 1/2011 | Elshout | |
| 8,202,317 B2 | 6/2012 | Becker | |
| 8,313,527 B2 | 11/2012 | Powell et al. | |
| 8,506,627 B2 | 8/2013 | Van Epps et al. | |
| 8,546,458 B2 | 10/2013 | Thompson et al. | |
| 8,562,677 B2 | 10/2013 | Job | |
| 8,679,279 B2 | 3/2014 | Thompson et al. | |
| 8,728,159 B2 | 5/2014 | Kim | |
| 8,765,039 B1 | 7/2014 | Ledergerber | |
| 9,011,333 B2 | 4/2015 | Geissler et al. | |
| 9,044,897 B2 | 6/2015 | Manesis et al. | |
| 9,155,613 B2 | 10/2015 | Thompson et al. | |
| 9,205,238 B2 | 12/2015 | Ledergerber | |
| 9,205,577 B2 * | 12/2015 | Liu | A61L 28/0034 |
| 9,593,224 B2 | 3/2017 | Liu et al. | |
| 9,673,516 B2 | 6/2017 | Mejia | |
| 9,688,006 B2 | 6/2017 | Nieto et al. | |
| 9,750,600 B2 | 9/2017 | Mayo | |
| 9,901,438 B2 | 2/2018 | Mejia et al. | |
| 10,111,744 B2 | 10/2018 | Mora et al. | |
| 10,176,412 B2 | 1/2019 | Geissler et al. | |
| 2001/0014339 A1 * | 8/2001 | Shigeyuki | A61K 9/1617 424/400 |
| 2002/0005600 A1 * | 1/2002 | Ma | B01J 20/285 264/49 |
| 2002/0032149 A1 * | 3/2002 | Kensey | G01N 11/00 514/1 |
| 2002/0038147 A1 | 3/2002 | Miller | |
| 2002/0103229 A1 * | 8/2002 | Bhagwat | C07D 231/56 514/338 |
| 2002/0132854 A1 * | 9/2002 | Zemlan | A61K 9/1647 514/625 |
| 2002/0193885 A1 | 12/2002 | Legeay | |
| 2003/0036803 A1 | 2/2003 | McGhan | |
| 2003/0093151 A1 | 5/2003 | Zhang | |
| 2003/0105469 A1 | 6/2003 | Karmon | |
| 2003/0129717 A1 * | 7/2003 | Becker | C11D 3/38 435/174 |
| 2003/0203027 A1 * | 10/2003 | Verreck | A61K 9/2086 424/471 |
| 2003/0203926 A1 * | 10/2003 | Kois | C07D 239/42 514/275 |
| 2003/0205846 A1 | 11/2003 | Bellin | |

(56) References Cited

U.S. PATENT DOCUMENTS

| | | |
|---|---|---|
| 2003/0208269 A1 | 11/2003 | Eaton et al. |
| 2003/0220330 A1* | 11/2003 | Yoshitaka ............ A61K 31/496 514/227.8 |
| 2003/0232082 A1* | 12/2003 | Li ........................ A23G 1/54 424/473 |
| 2004/0010225 A1 | 1/2004 | Schuessler |
| 2004/0106634 A1* | 6/2004 | Satoh ................... A61K 31/496 514/275 |
| 2004/0115241 A1 | 6/2004 | Calhoun |
| 2004/0127536 A1* | 7/2004 | Bhagwat .............. A61K 31/416 514/406 |
| 2004/0127985 A1 | 7/2004 | Bellin |
| 2004/0137032 A1 | 7/2004 | Wang |
| 2004/0143327 A1 | 7/2004 | Ku |
| 2004/0148024 A1 | 7/2004 | Williams |
| 2004/0153151 A1 | 8/2004 | Gonzales de Vicente |
| 2004/0176493 A1 | 9/2004 | Ferguson |
| 2004/0213986 A1 | 10/2004 | Kim |
| 2005/0009876 A1* | 1/2005 | Bhagwat .............. A61K 31/416 514/338 |
| 2005/0055093 A1 | 3/2005 | Brennan |
| 2005/0070124 A1 | 3/2005 | Miller |
| 2005/0112169 A1 | 5/2005 | Brauker |
| 2005/0122169 A1 | 6/2005 | Watanabe |
| 2005/0137231 A1* | 6/2005 | McKie ................. C07D 311/14 514/320 |
| 2005/0175702 A1 | 8/2005 | Muller-Schulte |
| 2005/0196452 A1 | 9/2005 | Boyan |
| 2005/0216094 A1 | 9/2005 | Prewett |
| 2005/0238683 A1* | 10/2005 | Adhikari .................. A61F 2/30 424/423 |
| 2005/0251083 A1 | 11/2005 | Carr-Brendel et al. |
| 2006/0002810 A1 | 1/2006 | Grohowski, Jr. |
| 2006/0018957 A1* | 1/2006 | Lerner ................. A61K 9/2018 424/451 |
| 2006/0036266 A1 | 2/2006 | Andreevich |
| 2006/0036320 A1 | 2/2006 | Job |
| 2006/0051394 A1* | 3/2006 | Moore .................... A61L 27/18 424/423 |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2006/0257377 A1 | 11/2006 | Atala et al. |
| 2006/0287344 A1* | 12/2006 | Albers ................... A61K 31/52 514/263.2 |
| 2007/0004777 A1* | 1/2007 | Bhagwat ............. A61K 31/4196 514/322 |
| 2007/0015817 A1* | 1/2007 | McKie ................. C07D 311/16 514/422 |
| 2007/0036844 A1* | 2/2007 | Ma ........................ A61L 27/56 424/443 |
| 2007/0037882 A1* | 2/2007 | Kita ...................... A61K 31/192 514/548 |
| 2007/0060598 A1* | 3/2007 | Albers ................... A61K 31/52 514/263.23 |
| 2007/0093911 A1 | 4/2007 | Fricke |
| 2007/0104693 A1 | 5/2007 | Quijano et al. |
| 2007/0104695 A1 | 5/2007 | Quijano |
| 2007/0116735 A1 | 5/2007 | Calhoun |
| 2007/0135916 A1 | 6/2007 | Maxwell et al. |
| 2007/0154525 A1 | 7/2007 | Calhoun |
| 2007/0190108 A1 | 8/2007 | Datta |
| 2007/0198085 A1 | 8/2007 | Benslimane |
| 2008/0009830 A1 | 1/2008 | Fujimoto |
| 2008/0071371 A1 | 3/2008 | Elshout |
| 2008/0075752 A1* | 3/2008 | Ratner ................. A61F 2/0077 424/426 |
| 2008/0095823 A1 | 4/2008 | Williams et al. |
| 2008/0118545 A1* | 5/2008 | Futo ..................... A61K 9/0019 424/426 |
| 2008/0138453 A1* | 6/2008 | Gu .......................... A61K 36/48 424/776 |
| 2008/0154366 A1 | 6/2008 | Frank |
| 2008/0241212 A1 | 10/2008 | Moses |
| 2008/0242694 A1* | 10/2008 | D'Sidocky .......... C07D 285/135 514/300 |
| 2008/0268019 A1 | 10/2008 | Badylak |
| 2008/0312739 A1 | 12/2008 | Agerup |
| 2009/0023724 A1* | 1/2009 | Mortensen ........... C07D 471/04 514/234.2 |
| 2009/0028941 A1* | 1/2009 | Cowles ................ A61K 9/0065 424/469 |
| 2009/0042890 A1* | 2/2009 | Mortensen ........... C07D 473/00 514/249 |
| 2009/0045166 A1 | 2/2009 | Li |
| 2009/0048275 A1* | 2/2009 | Beauchamps ........ C07D 487/04 514/263.23 |
| 2009/0082864 A1 | 3/2009 | Chen |
| 2009/0087641 A1 | 4/2009 | Favis |
| 2009/0093878 A1 | 4/2009 | Glicksman |
| 2009/0118829 A1 | 5/2009 | Powell |
| 2009/0125107 A1 | 5/2009 | Maxwell |
| 2009/0148829 A1 | 6/2009 | Ecker |
| 2009/0162447 A1* | 6/2009 | Kaully ................ A61K 9/0017 424/490 |
| 2009/0169716 A1 | 7/2009 | Linhardt |
| 2009/0198331 A1 | 8/2009 | Kesten |
| 2009/0198332 A1 | 8/2009 | Becker |
| 2009/0198333 A1 | 8/2009 | Becker |
| 2009/0270418 A1* | 10/2009 | Sloss .................... C07D 401/14 514/255.05 |
| 2009/0326025 A1* | 12/2009 | Lu ......................... A61K 9/1623 514/381 |
| 2010/0042211 A1 | 2/2010 | Van Epps et al. |
| 2010/0075056 A1 | 3/2010 | Axisa et al. |
| 2010/0093698 A1* | 4/2010 | Bahmanyar .......... C07D 471/04 514/210.21 |
| 2010/0112032 A1 | 5/2010 | Guicher |
| 2010/0120727 A1* | 5/2010 | Xu ........................ A61K 31/195 514/165 |
| 2010/0190708 A1* | 7/2010 | Tsuno .................. A61K 38/168 514/21.2 |
| 2010/0234288 A1* | 9/2010 | Jain ....................... A61K 9/2853 514/7.7 |
| 2010/0292790 A1 | 11/2010 | Stroumpoulis et al. |
| 2011/0054605 A1 | 3/2011 | Becker |
| 2011/0082148 A1* | 4/2011 | Klopman .............. A61K 31/381 514/248 |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0172798 A1 | 7/2011 | Staiger |
| 2011/0196488 A1 | 8/2011 | Goraltchouk et al. |
| 2011/0196489 A1 | 8/2011 | Van Epps et al. |
| 2011/0257623 A1 | 10/2011 | Marshall et al. |
| 2011/0276133 A1 | 11/2011 | Liu et al. |
| 2011/0276134 A1 | 11/2011 | Manesis et al. |
| 2011/0278755 A1* | 11/2011 | Liu ........................ A61L 27/16 264/41 |
| 2011/0282444 A1 | 11/2011 | Liu et al. |
| 2011/0300214 A1* | 12/2011 | Rimkus ................ A61K 9/2027 424/465 |
| 2011/0309541 A1 | 12/2011 | Thompson et al. |
| 2011/0313073 A1 | 12/2011 | Goraltchouk et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077891 A1 | 3/2012 | Liu et al. |
| 2012/0101574 A1 | 4/2012 | Goraltchouk et al. |
| 2012/0232652 A1 | 9/2012 | Mora et al. |
| 2012/0245685 A1 | 9/2012 | Yu |
| 2012/0321777 A1 | 12/2012 | Stroumpoulis et al. |
| 2013/0013062 A1 | 1/2013 | Thompson et al. |
| 2013/0023987 A1 | 1/2013 | Liu et al. |
| 2013/0030025 A1* | 1/2013 | Wessel .................. A61K 31/44 514/352 |
| 2013/0032962 A1* | 2/2013 | Liu ..................... A61L 28/0034 264/41 |

(56) References Cited

U.S. PATENT DOCUMENTS

| | | | |
|---|---|---|---|
| 2013/0034633 A1* | 2/2013 | von Hasseln | B33Y 10/00 426/104 |
| 2013/0053956 A1 | 2/2013 | Powell et al. | |
| 2013/0158657 A1 | 6/2013 | Nofrey et al. | |
| 2013/0209661 A1 | 8/2013 | Goraltchouk et al. | |
| 2013/0245148 A1 | 9/2013 | Thompson et al. | |
| 2013/0261745 A1 | 10/2013 | Van Epps | |
| 2013/0302511 A1 | 11/2013 | Goraltchouk et al. | |
| 2013/0310934 A1 | 11/2013 | Van Epps et al. | |
| 2015/0282926 A1 | 10/2015 | Chacon et al. | |
| 2016/0022866 A1 | 1/2016 | Liu et al. | |
| 2016/0130690 A1 | 5/2016 | Winn et al. | |
| 2017/0049549 A1 | 2/2017 | Bayat et al. | |
| 2017/0256850 A1 | 9/2017 | Mejia | |
| 2017/0290652 A1 | 10/2017 | Nieto et al. | |
| 2018/0092726 A1 | 4/2018 | Van Epps et al. | |
| 2018/0200043 A1 | 7/2018 | Mejia et al. | |
| 2018/0360594 A1 | 12/2018 | Schuessler et al. | |
| 2019/0029807 A1 | 1/2019 | Nieto et al. | |
| 2020/0237968 A1* | 7/2020 | Liu | A61L 27/26 |

FOREIGN PATENT DOCUMENTS

| | | |
|---|---|---|
| CA | 2975348 | 8/2015 |
| CA | 3007138 | 6/2017 |
| CA | 3013698 | 8/2017 |
| CA | 3019747 | 10/2017 |
| CA | 3020876 | 10/2017 |
| CA | 3023507 | 11/2017 |
| CN | 2587376 | 11/2003 |
| CN | 104837441 | 8/2015 |
| CN | 108697337 | 10/2018 |
| CN | 109069251 | 12/2018 |
| CN | 109152531 | 1/2019 |
| CN | 109152640 | 1/2019 |
| EP | 0230672 | 8/1987 |
| EP | 0293256 | 11/1988 |
| EP | 0315814 | 5/1989 |
| EP | 0332371 | 9/1989 |
| EP | 0419134 | 3/1991 |
| EP | 0522585 | 1/1993 |
| EP | 0710468 | 1/2002 |
| EP | 1532942 | 5/2005 |
| EP | 1796595 | 6/2007 |
| EP | 1847369 | 12/2008 |
| EP | 2446858 | 5/2012 |
| EP | 2568875 | 3/2013 |
| EP | 2895994 | 7/2015 |
| EP | 2921137 | 9/2015 |
| EP | 2931490 | 10/2015 |
| EP | 2962662 | 1/2016 |
| EP | 3107487 | 12/2016 |
| EP | 3383314 | 10/2018 |
| EP | 3413788 | 12/2018 |
| EP | 2895109 B1 | 1/2019 |
| EP | 3439543 | 2/2019 |
| EP | 3442468 | 2/2019 |
| EP | 3443933 | 2/2019 |
| EP | 2227175 B1 | 3/2019 |
| ES | 2409691 | 6/2013 |
| FR | 2840617 | 12/2003 |
| GB | 1022736 | 3/1966 |
| GB | 2225016 | 5/1990 |
| JP | H 01-271438 | 10/1989 |
| JP | H 02-251544 | 10/1990 |
| JP | H 10-512176 | 11/1998 |
| JP | 2003-062062 | 4/2003 |
| JP | 2007-029717 | 8/2007 |
| JP | 2009-502364 | 1/2009 |
| JP | 2006-512171 | 4/2016 |
| KR | 20180103873 | 9/2018 |
| KR | 20180116302 | 10/2018 |
| KR | 20180134358 | 12/2018 |
| KR | 20180137503 | 12/2018 |
| KR | 20190008252 | 1/2019 |
| MX | 2012012801 | 5/2014 |
| RU | 2340308 | 12/2008 |
| WO | WO 90/14927 | 12/1990 |
| WO | WO 97/15242 | 5/1997 |
| WO | WO 98/010803 | 3/1998 |
| WO | WO 98/42318 | 10/1998 |
| WO | WO 00/024437 | 5/2000 |
| WO | WO 00/56376 | 9/2000 |
| WO | WO 2004/037318 | 5/2004 |
| WO | WO 2004/062531 | 7/2004 |
| WO | WO 2005/020849 | 3/2005 |
| WO | WO 2006/133366 | 12/2006 |
| WO | WO 2007/126411 | 11/2007 |
| WO | WO 2008/001591 | 1/2008 |
| WO | WO 2009/061672 | 5/2009 |
| WO | WO 2009/110917 | 9/2009 |
| WO | WO 2010/019292 | 2/2010 |
| WO | WO 2010/019761 | 2/2010 |
| WO | WO 2010/136840 | 12/2010 |
| WO | WO 2011/066441 | 6/2011 |
| WO | WO 2011/094155 | 8/2011 |
| WO | WO 2011/097499 | 8/2011 |
| WO | WO 2011/143324 | 11/2011 |
| WO | WO 2013/184569 | 12/2013 |
| WO | WO 2014/043631 | 3/2014 |
| WO | WO 2014/047013 | 3/2014 |
| WO | WO 2014/076339 | 5/2014 |
| WO | WO 2015/121686 | 8/2015 |
| WO | WO 2017/093528 | 6/2017 |
| WO | WO 2017/137853 | 7/2017 |
| WO | WO 2017/175055 | 10/2017 |
| WO | WO 2017/181144 | 10/2017 |
| WO | WO 2017/184962 | 10/2017 |
| WO | WO 2017/196973 | 11/2017 |
| WO | WO 2018/078446 | 5/2018 |
| WO | WO 2018/188930 | 10/2018 |

* cited by examiner

Under-fused and over-fused porogens

Uniformly-fused porogens

POROGEN COMPOSITIONS, METHODS OF MAKING AND USES

This application is a continuation of U.S. patent application Ser. No. 14/960,075 filed on Dec. 4, 2015, which is a continuation of U.S. patent application Ser. No. 13/631,091, filed Sep. 28, 2012, now U.S. Pat. No. 9,205,577, issued Dec. 8, 2015, which is a continuation-in-part application of U.S. patent application Ser. No. 13/104,811, filed May 10, 2011, now U.S. Pat. No. 8,685,296, issued Apr. 1, 2014, which claims priority to U.S. Provisional App. No. 61/333,599, filed May 11, 2010; each of which is hereby incorporated by reference in its entirety.

Porous materials are widely used in biomedical, industrial, and household applications. In the biomedical field, porous materials have been used as a matrix for tissue engineering/regeneration, wound dressings, drug release matrices, membranes for separations and filtration, sterile filters, artificial kidneys, absorbents, hemostatic devices, and the like. In various industrial and household applications, porous materials have been used as insulating materials, packaging materials, impact absorbers, liquid or gas absorbents, membranes, filters and so forth.

One general method of making a porous material relies on a three-dimensional scaffold used as a negative template. One such example is the porogen scaffold method. In this method, porogens are poured into a mold and treated, such as, e.g., by physical and/or chemical means to fuse the porogens, thereby forming a porogen scaffold comprising fused porogens that are all connected to one another. A material is then poured into the mold to coat the porogen scaffold and this material is then stabilized, such as, e.g., a curing process or a freezing process. After stabilization, the porogen scaffold is removed, leaving behind a porous material. See, e.g., Ma, Reverse Fabrication of Porous Materials, U.S. Patent Pub. No. 2002/0005600; Ratner and Marshall, Novel Porous Materials, U.S. Patent Pub. No. 2008/0075752; Ma and Chen, Porous Materials having Multi-Sized Geometries, U.S. Patent Pub. No. 2007/0036844, each of which is incorporated by reference in its entirety.

The porogens used to make the porogen scaffolds are currently composed of a single material, such as, e.g., gelatin, sucrose, or poly(lactide-co-glycolide). Controlling the fusion of these single-material porogens during treatment is difficult, in part due to the random timing with which each individual porogen transitions from its solid phase to its liquid phase. For example, most porogens are fused using thermal means where the porogens, in the solid phase, are heated to a temperature above their melting point (or glass transition point). At this temperature, the porogens transition to a liquid phase, allowing the porogens to melt together. Too short a thermal treatment will result in an insufficient number of porogen fusions, whereas too long a treatment will result in formation of a solid block of fused porogens. However, even though comprised of the same material, not all porogens will melt at the same time. Under any given treatment condition designed to cause porogen fusion, there will generally be a population of porogens that are in the solid phase, while at the same time will be a population of porogens that have completely transitioned into the liquid or rubbery phase (FIG. 1). This unequal or uncontrolled transition from the solid phase to the liquid or rubbery phase results in a porogen scaffold that comprises regions of insufficient porogen fusion (or under-fusion) and/or too much porogen fusion (over-fusion). The poorly controlled nature of the fusion process results in a porogen scaffold that is not of uniform structure, which in turn results in porous materials that are not of uniform porosity and hence have lower utility.

As such, there is a continuing need for porogens that upon physical and/or chemical treatment, a porogen scaffold of uniformly fused porogens is produced.

SUMMARY

The present application discloses porogen compositions comprising a shell material and a core material and methods of making these porogen compositions. Upon physical and/or chemical treatment the porogen compositions disclosed herein produce porogen scaffold of uniformly fused porogens.

Thus, aspects of the present specification disclose a porogen composition comprising a shell material and a core material.

Other aspects of the present specification disclose a method of forming a porogen composition, the method comprising the steps of: a) making a particle out of a core material; and b) coating the particle with a shell material.

Yet other aspects of the present specification disclose a method of forming a porous material, the method comprising the steps of: a) fusing porogens disclosed herein to form a porogen scaffold comprising fused porogens; b) coating the porogen scaffold with a substance base to form a substance coated porogen scaffold; c) treating the substance coated porogen scaffold to stabilize the substance; and d) removing the porogen scaffold, wherein porogen scaffold removal results in a porous material, the porous material comprising a matrix defining an array of interconnected pores.

Yet other aspects of the present specification disclose a method of forming a porous material, the method comprising the steps of: a) coating porogens disclosed herein with a substance base to form a substance coated porogen mixture; b) treating the substance coated porogen mixture to form a porogen scaffold and stabilize the substance; and c) removing the porogen scaffold, wherein porogen scaffold removal results in a porous material, the porous material comprising a matrix defining an array of interconnected pores.

Still other aspects of the present specification disclose a method of forming a porous material, the method comprising the steps of: a) packing porogens disclosed herein into a mold; b) fusing the porogens to form a porogen scaffold comprising fused porogens; c) coating the porogen scaffold with a substance base to form a substance coated porogen scaffold; d) treating the substance coated porogen scaffold to stabilize the substance; and e) removing the porogen scaffold, wherein porogen scaffold removal results in a porous material, the porous material comprising a matrix defining an array of interconnected pores.

Still other aspects of the present specification disclose a method of forming a porous material, the method comprising the steps of: a) coating porogens disclosed herein with a substance base to form a substance coated porogen mixture; b) packing substance coated porogen mixture into a mold; c) treating the substance coated porogen mixture to form a porogen scaffold and stabilize the substance; and d) removing the porogen scaffold, wherein porogen scaffold removal results in a porous material, the porous material comprising a matrix defining an array of interconnected pores.

Further aspects of the present specification disclose a method of making a biocompatible implantable device, the method comprising the steps of: a) preparing the surface of a biocompatible implantable device to receive a porous material; b) attaching a porous material to the prepared surface of the biocompatible implantable device. The porous material can be made by the method disclosed herein.

Further aspects of the present specification disclose a method for making a biocompatible implantable device, the method comprising the step of: a) coating a mandrel with a substance base; b) curing the substance base to form a base layer; c) coating the cured base layer with a substance base; d) coating the substance base with porogens to form a substance coated porogen mixture, the porogens disclosed herein; e) treating the substance coated porogen mixture to form a porogen scaffold comprising fused porogens and cure the substance base; and f) removing the porogen scaffold, wherein porogen scaffold removal results in a porous material, the porous material comprising a non-degradable, biocompatible, substance matrix defining an array of interconnected pores. In this method steps (c) and (d) can be repeated multiple times until the desired thickness of the material layer is achieved.

Further aspects of the present specification disclose a method of making a biocompatible implantable device, the method comprising the steps of: a) preparing the surface of a biocompatible implantable device to receive a porous material; and, b) attaching a porous material disclosed herein to the prepared surface of the biocompatible implantable device.

In some aspects of the present specification the biocompatible implantable device is a breast implant.

BRIEF DESCRIPTION OF THE DRAWINGS

FIG. 2 illustrates a representative biocompatible implantable device covered with a porous material of the present specification.

FIG. 3 illustrates a representative porous material shell of the present specification.

FIG. 4 illustrates a representative biocompatible implantable device covered with a porous material of the present specification.

FIG. 5A is scanning electron micrograph image at 50× magnification of the top-view of the porous material. FIG. 5B is scanning electron micrograph image at 50× magnification of the cross-section of the porous material.

FIG. 6A is scanning electron micrograph image at 50× magnification of the top-view of the porous material. FIG. 6B is scanning electron micrograph image at 50× magnification of the cross-section of the porous material.

FIG. 7A is scanning electron micrograph image at 50× magnification of the top-view of the porous material. FIG. 7B is scanning electron micrograph image at 50× magnification of the cross-section of the porous material.

FIG. 8A is scanning electron micrograph image at 50× magnification of the top-view of the porous material. FIG. 8B is scanning electron micrograph image at 50× magnification of the cross-section of the porous material.

FIG. 9A shows a bar graph of thickness data as normalized mean±normalized standard deviation. FIG. 9B shows a bar graph of disorganization normalized with a standard deviation with upper and lower bounds of confidence intervals.

DETAILED DESCRIPTION

Figure 1:
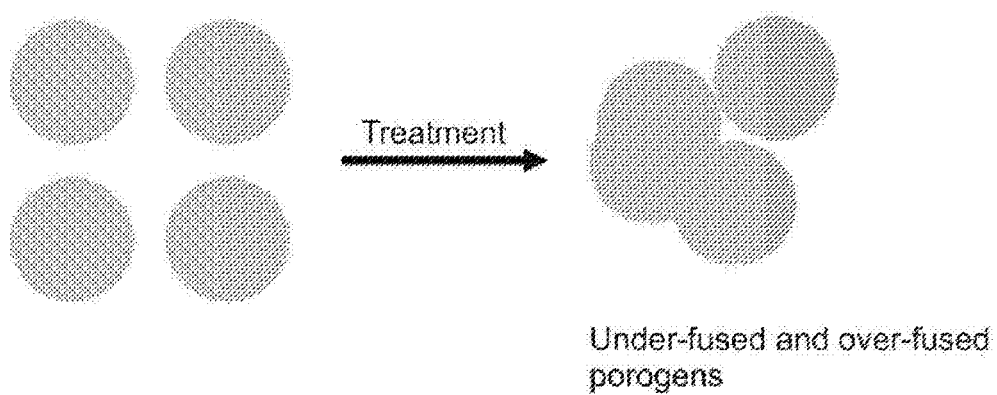
FIG. 1 illustrates the porogens consisting of a single material and porogens comprising a shell material and a core material as disclosed in the present specification. Controlled fusion of porogens consisting of a single material is difficult due to the random timing that each porogen transitions from its solid phase to its liquid phase. As such, fusing porogens under a treatment results in insufficient fusion of the porogens (or under-fusion) and/or too much fusion of porogens (over-fusion). Controlled fusion of porogens can be accomplished using the porogen compositions disclosed in the present specification. Treatment is done under conditions that allow the shell material to transition from its solid phase to its liquid phase, but maintain the core material in its solid phase. As such, fusion of porogen compositions disclosed herein result in a more uniform porogen scaffold.
Figure 1:
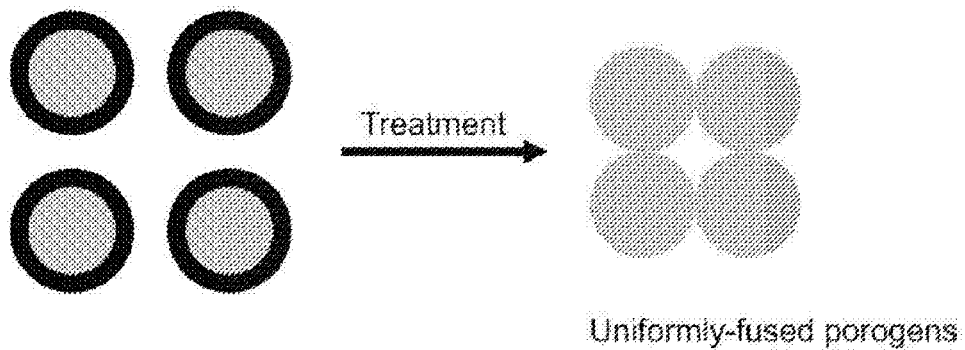

The porogen compositions disclosed herein provide a means to control the degree and amount of fusion that occurs during a treatment. This is accomplished, in part, by providing a shell material and a core material, where the shell material has a lower melting point temperature and/or glass transition temperature relative to the core material. Currently, porogens are composed of a single material. Controlling the fusion of these single material porogens is difficult, due, in part, to the random timing that each individual porogen transitions from its solid phase to its liquid phase. As such, under any given treatment condition designed to cause porogen fusion, there will be a population of porogens that have remained in the solid phase, and yet at the same time, a population of porogens that have completely transitioned into their liquid or rubbery phase (FIG. 1). This unequal or uncontrolled transition from the solid phase to the liquid or rubbery phase results in a porogen scaffold that comprises regions of insufficient porogen fusion (or under-fusion) and/or too much porogen fusion (over-fusion). The uncontrolled nature of the fusion process produces an un-uniform porogen scaffold that ultimately results in porous materials with a matrix of un-uniform pore sizes and interconnections. Such a disorganized structure can reduce the utility of porous materials. The porogen compositions disclosed herein overcome the uncontrollable fusion rates observed in single material porogens. The compositions disclosed herein comprise porogens comprising a shell material and a core material. Controlled fusion of porogens is achieved because fusion treatment is performed under conditions that allow the shell material to transition from its solid phase to its liquid or rubbery phase, but the core material is maintained in its solid phase. As such, fusion of porogen compositions disclosed herein result in a more uniform porogen scaffold (FIG. 1). Thus, a method of making a porous material that utilizes a porogen composition of the present specification will produce a porous material with a more uniform matrix of pore size and interconnections.

The present specification discloses, in part, a porogen composition. As used herein, the term "porogen composition" or "porogen(s)" refers to any structured material that can be used to create a porous material.

Porogens have a shape sufficient to allow formation of a porogen scaffold useful in making a substance matrix as disclosed herein. Any porogen shape is useful with the proviso that the porogen shape is sufficient to allow formation of a porogen scaffold useful in making a substance matrix as disclosed herein. Useful porogen shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

In an embodiment, porogens have a shape sufficient to allow formation of a porogen scaffold useful in making a substance matrix that allows tissue growth within its array of interconnected of pores. In aspects of this embodiment, porogens have a shape that is roughly spherical, perfectly spherical, ellipsoidal, polyhedronal, triangular, pyramidal, quadrilateral, or polygonal.

Porogens have a roundness sufficient to allow formation of a porogen scaffold useful in making a matrix defining an array of interconnected of pores. As used herein, "roundness" is defined as $(6 \times V)/(\pi \times D3)$, where V is the volume and D is the diameter. Any porogen roundness is useful with the proviso that the porogen roundness is sufficient to allow formation of a porogen scaffold useful in making a substance matrix as disclosed herein.

In an embodiment, porogens have a roundness sufficient to allow formation of a porogen scaffold useful in making a matrix defining an array of interconnected of pores. In aspects of this embodiment, porogens have a mean roundness of, e.g., about 0.1, about 0.2, about 0.3, about 0.4, about 0.5, about 0.6, about 0.7, about 0.8, about 0.9, or about 1.0. In other aspects of this embodiment, porogens have a mean roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, porogens have a mean roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, have a mean roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

A porogen has a thickness sufficient to allow formation of a porogen scaffold. As such, a porogen can be of any thickness, with the proviso that the thickness of the porogen is sufficient to create a porogen scaffold useful for its intended purpose. The thickness of a porogen can be measured base on its shape. For example, for spherical and elliptical porogens, thickness is measured based on the diameter of the core material. For example, for sided-shaped porogens, like polyhedrons, triangles, pyramids, quadrilateral, or polygons, thickness is measured based on the base width of the porogen.

In another embodiment, a porogen comprises mean porogen diameter sufficient to allow formation of a porogen scaffold useful in making a matrix defining an array of interconnected of pores. In aspects of this embodiment, a porogen comprises mean porogen diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen comprises mean porogen diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen comprises mean porogen diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porogen comprises mean porogen diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen comprises mean porogen diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porogen comprises mean porogen diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen comprises mean porogen diameter of, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porogen comprise mean porogen base sufficient to allow formation of a porogen scaffold useful in making a matrix defining an array of interconnected of pores. In aspects of this embodiment, a porogen comprises mean porogen base of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen comprises mean porogen base of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen comprises mean porogen base of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porogen comprises mean porogen base of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen comprises mean porogen base of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porogen comprises mean porogen base of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen comprises mean porogen base of, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

The present specification discloses, in part, a porogen comprising a shell material. A shell material of a porogen can be made of any material with the proviso that 1) the melting point temperature (Tm) of the shell material is lower than the melting point temperature of the core material; and/or 2) the glass transition temperature (Tg) of the shell material is lower than the glass transition temperature of the core material. As used herein, the term "melting point temperature" or "melting point" refers to the temperature at which the solid and liquid phases of a material exist in equilibrium, at any fixed pressure, and is the temperature at which the first trace of liquid appears. For a material made of a pure substance, the melting, or fusion, process occurs at a single temperature. For a material made of two or more substances, the melting process normally occurs over a range of temperatures, and a distinction is made between the melting point and the freezing point temperature. As used herein, the term "freezing point temperature" or "freezing point" refers to the temperature at which the solid and liquid phases of a material exist in equilibrium, at any fixed pressure, and is the temperature at which the last trace of solid disappears. The freezing point temperature is usually higher than the melting point temperature in materials made from two or more substances.

Amorphous materials, as well as some polymers, do not have a true melting point temperature as there is no abrupt phase change from a solid phase to a liquid phase at any specific temperature. Instead, amorphous materials and polymers exhibit a gradual change in viscoelastic properties over a range of temperatures. Such materials are characterized by vitrification, or glass transition, the process of converting a material into a glassy amorphous solid that is free from crystalline structure. Vitrification occurs at a glass transition temperature. As used herein, the term "glass transition temperature" refers to the temperature at which the glass and liquid phases of an amorphous material exist in equilibrium, at any fixed pressure, and is the temperature that roughly defined the "knee" point of the material's density vs. temperature graph. The glass transition temperature of an amorphous material is lower than its melting temperature.

A shell material can comprise a natural or synthetic, inorganic or organic material. Exemplary materials suitable as a shell material disclosed herein, include, without limitation, natural and synthetic salt and its derivatives, natural and synthetic ceramic and/or its derivatives, natural and synthetic sugar and its derivatives, natural and synthetic polysaccharide and its derivatives, natural and synthetic wax and its derivatives, natural and synthetic metal and its derivatives, natural and synthetic surfactant and its derivatives, natural and synthetic organic solid and its derivatives, natural and synthetic water soluble solid and its derivatives, and/or natural and synthetic polymer and its derivatives, composites thereof, and/or combinations thereof.

A natural or synthetic salt and its derivatives refer to ionic compounds composed of cations and anions so that the product is electrically neutral. The component ions of a salt can be inorganic or organic, as well as, a monoatomic ion or a polyatomic ion. Common salt-forming cations include, without limitation, Ammonium $NH_4^+$, Calcium $Ca^{2+}$, Iron $Fe^{2+}$ and $Fe^{3+}$, Magnesium $Mg^{2+}$, Potassium $K^+$, Pyridinium $C_5H_5NH^+$, Quaternary ammonium $NR_4^+$, and Sodium $Na^+$. Common salt-forming anions include, without limitation, Acetate $CH_3COO^-$, Carbonate $CO_3^{2-}$, Chloride $Cl^-$, Citrate $HOC(COO^-)(CH_2COO^-)_2$, Cyanide $C\equiv N^-$, Hydroxide $OH^-$, Nitrate $NO_3^-$, Nitrite $NO_2^-$, Oxide $O^{2-}$, Phosphate $PO_4^{3-}$, and Sulfate $SO_4^{2-}$. Non-limiting examples of salts include, cobalt chloride hexahydrate, copper sulfate pentahydrate, ferric hexacyanoferrate, lead diacetate, magnesium sulfate, manganese dioxide, mercury sulfide, monosodium glutamate, nickel chloride hexahydrate, potassium bitartrate, potassium chloride, potassium dichromate, potassium fluoride, potassium permanganate, sodium alginate, sodium chromate, sodium chloride, sodium fluoride, sodium iodate, sodium iodide, sodium nitrate, sodium sulfate, and/or mixtures thereof.

A natural or synthetic ceramic and its derivatives refer to inorganic, non-metallic solids that can have a crystalline or partly crystalline structure, or can be amorphous (e.g., a glass). Ceramics include oxides, such as, e.g., alumina and zirconium dioxide, non-oxides, such as, e.g., carbides, borides, nitrides, and silicides; and composites comprising combinations of oxides and non-oxides. Non-limiting examples of salts include, alumina, barium titanate, bismuth strontium calcium copper oxide, boron nitride, lead zirconate titanate, magnesium diboride, Silicon aluminum oxynitride, silicon carbide, silicon nitride, strontium titanate, titanium carbide, uranium oxide, yttrium barium copper oxide, zinc oxide, and zirconium dioxide.

A natural or synthetic sugar and its derivatives refer to a compound comprising one to 10 monosaccharide units, e.g., a monosaccharide, a disaccharide, a trisaccharide, and an oligosaccharide comprising four to ten monosaccharide units. Monosaccharides are polyhydroxy aldehydes or polyhydroxy ketones with three or more carbon atoms, including aldoses, dialdoses, aldoketoses, ketoses and diketoses, as well as cyclic forms, deoxy sugars and amino sugars, and their derivatives, provided that the parent monosaccharide has a (potential) carbonyl group. Oligosaccharides are compounds in which at least two monosaccharide units are joined by glycosidic linkages. According to the number of units, they are called disaccharides, trisaccharides, tetrasaccharides, pentasaccharides, hexoaccharides, heptoaccharides, octoaccharides, nonoaccharides, decoaccharides, etc. An oligosaccharide can be unbranched, branched or cyclic. Non-limiting examples of sugars include, monosacchrides, such as, e.g., trioses, like glyceraldehyde and dihydroxyacetone; tetroses, like erythrose, threose and erythrulose; pentoses, like arabinose, lyxose, ribose, xylose, ribulose, xylulose; hexoses, like allose, altrose, galactose, glucose, gulose, idose, mannose, talose, fructose, psicose, sorbose, tagatose, fucose, rhamnose; heptoses, like sedoheptulose and mannoheptulose; octooses, like octulose and 2-keto-3-deoxy-manno-octonate; nonoses like sialose; and decose; and oligosaccharides, such as, e.g., disaccharides, like sucrose, lactose, maltose, trehalose, cellobiose, gentiobiose, kojibiose, laminaribiose, mannobiose, melibiose, nigerose, rutinose, and xylobiose; trisaccharides like raffinose, acarbose, maltotriose, and melezitose and/or mixtures thereof. Sugars also include sugar substitutes like acesulfame potassium, alitame, aspartame, acesulfame, cyclamate, dulcin, glucin, neohesperidin dihydrochalcone, neotame, saccharin, and sucralose.

A natural or synthetic polysaccharide and its derivatives refer to a polymeric carbohydrate compound comprising more than 10 repeating monosaccharide of disaccharide units joined by glycosidic bonds. A polysaccharide can be linear or contain various degrees of branching. Depending on the structure, these macromolecules can have distinct properties from their monosaccharide building blocks. They may be amorphous or even insoluble in water. When all the monosaccharides in a polysaccharide are the same type the polysaccharide is called a homopolysaccharide, but when more than one type of monosaccharide is present they are called heteropolysaccharides. Non-limiting examples of polysaccharides include, amylose; cellulose; cellulose derivatives (like FICOLL, alkyl cellulose, carboxy cellulose, methyl cellulose, carboxymethyl cellulose, hemicellulose, hydroxyethyl cellulose, hydroxypropyl cellulose, hydroxyethyl methyl cellulose, hydroxypropyl methyl cellulose); chitin; chitosan; dextrans (like dextran 1K, dextran 4K, dextran 40K, dextran 60K, and dextran 70K); dextrin; glycogen; inulin; glcosaminoglycans (like chondrotin sulfates, keratin sulfates, heparin sulfates, alginic acid, hyaluronic acid); pectin; pullulan; starch; hetastarch; starch derivatives (like hydroxymethyl starch, hydroxyethyl starch, hydroxypropyl starch, hydroxybutyl starch, and hydroxypentyl starch); xanthan; and salts thereof.

A natural or synthetic wax and its derivatives refer to a type of lipid that contain a wide variety of long-chain alkanes, esters, polyesters and hydroxy esters of long-chain primary alcohols and fatty acids. Waxes are usually distinguished from fats by the lack of triglyceride esters of glycerin (propan-1,2,3-triol) and three fatty acids. Waxes include animal waxes, vegetable waxes, mineral waxes, petroleum waxes, synthetic waxes and/or mixtures thereof. Non-limiting examples of waxes include animal waxes like beeswax, Chinese wax, lanolin (wool wax), shellac wax, spermaceti; vegetable waxes like bayberry wax, candelilla wax, carnauba wax, castor wax, esparto wax, Japan wax, jojoba wax, ouricury wax, rice bran wax, soy wax; mineral waxes like ceresin wax, montan wax, ozocerite, peat wax; petroleum waxes like paraffin wax, microcrystalline wax, petroleum jelly; and synthetic waxes like polyethylene wax, Fischer-Tropsch wax, esterified wax, saponified wax, substituted amide wax, polymerized α-olefin wax.

A natural or synthetic metal and its derivatives refer to an element, compound, or alloy characterized by high electrical conductivity. An alloy is a mixture of two or more elements in solid solution in which the major component is a metal. A metal can be a base metal, a ferrous metal, a noble metal, or a precious metal. Non limiting examples of metals include alkali metals, like Lithium, Sodium, Potassium, Rubidium, Caesium, and Francium; alkaline earth metals like Beryllium, Magnesium, Calcium, Strontium, Barium, and Radium; transition metals like Zinc, Molybdenum, Cadmium, Scandium, Titanium, Vanadium, Chromium, Manganese, Iron, Cobalt, Nickel, Copper, Yttrium, Zirconium, Niobium, Technetium, Ruthenium, Rhodium, Palladium, Silver, Hafnium, Tantalum, Tungsten, Rhenium, Osmium, Iridium, Platinum, Gold, Mercury, Rutherfordium, Dubnium, Seaborgium, Bohrium, Hassium, Meitnerium, Darmstadtium, Roentgenium, and Copernicium; post-transition metals like Aluminium, Gallium, Indium, Tin, Thallium, Lead, Bismuth, Ununtrium, Ununquadium, Ununpentium, and Ununhexium; lanthanoids like Lanthanum, Cerium, Praseodymium, Neodymium, Promethium, Samarium, Europium, Gadolinium, Terbium, Dysprosium, Holmium, Erbium, Thulium, Ytterbium, and Lutetium; and actinoids like Actinium, Thorium, Protactinium, Uranium, Neptunium, Plutonium, Americium, Curium, Berkelium, Californium, Einsteinium, Fermium, Mendelevium, Nobelium, and Lawrencium.

A natural or synthetic surfactant and its derivatives refer to organic compounds that are amphiphilic and are soluble in both organic solvents and water. A surfactant includes, without limitation, ionic surfactants like cationic surfactants (based on quaternary ammonium cations) and anionic surfactants (based on sulfate, sulfonate or carboxylate anions), zwitterionic (amphoteric) surfactants, and/or non-ionic surfactants. Non-limiting examples of surfactants include anionic surfactants like perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate, also known as sodium lauryl ether sulfate (SLES), alkyl benzene sulfonate, soaps, and fatty acid salts; cationic surfactants like cetyl trimethylammonium bromide (CTAB), also known as hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); zwitterionic surfactants like dodecyl betaine, cocamidopropyl betaine, coco ampho glycinate; and nonionic surfactants like sucrose monolaurate, sodium cholate, dodecyl dimethylamine oxide, alkyl naphthalene sulfonates (ANS), alkyl poly(ethylene oxide), alkylphenol poly(ethylene oxide), poly(ethylene oxide) and poly(propylene oxide) co-polymers, also known as Poloxamers or Poloxamines including Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and Poloxamer 407 (PLURONIC® F127), alkyl polyglucosides, including octyl glucoside and decyl maltoside, fatty alcohols including cetyl alcohol and oleyl alcohol, cocamide MEA, cocamide DEA, polysorbates including polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN®

81); polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); and 3-[(3-Cholamidopropyl)dimethyl ammonio]-2-hydroxy-1-propanesulfonate (CHAPSO).

A natural or synthetic inorganic solid and its derivatives refer to a mineral not of biological origin. Non-limiting examples of inorganic solids include hydroxyapatite (HAP), carbonated hydroxyapatite, fluorinated hydroxyapatite, various calcium phosphates (CAP), glass, salts, oxides, silicates, and/or the like, and/or mixtures thereof.

A natural or synthetic water-soluble solid and its derivatives refer to any material that can be dissolved in water. Non-limiting examples of inorganic solids include sodium hydroxide and naphthalene.

A natural or synthetic polymer and its derivatives, refer to natural and synthetic macromolecules composed of repeating structural units typically connected by covalent chemical bonds. A polymer includes natural or synthetic hydrophilic polymers, natural or synthetic hydrophobic polymers, natural or synthetic amphiphilic polymers, degradable polymers, partially degradable polymers, non-degradable polymers, and combinations thereof. Polymers may be homopolymers or copolymers. Copolymers may be random copolymers, blocked copolymers, graft copolymers, and/or mixtures thereof. Non-limiting examples of polymers include poly (alkylene oxide), poly(acrylamide), poly(acrylic acid), poly (acrylamide-co-arylic acid), poly(acrylamide-co-diallyldimethylammonium chloride), poly(acrylonitrile), poly (allylamine), poly(amide), poly(anhydride), poly(butylene), poly(ε-caprolactone), poly(carbonate), poly(ester), poly (etheretherketone), poly(ethersulphone), poly(ethylene), poly(ethylene alcohol), poly(ethylenimine), poly(ethylene glycol), poly(ethylene oxide), poly(glycolide) ((like poly (glycolic acid)), poly(hydroxy butyrate), poly(hydroxyethylmethacrylate), poly(hydroxypropylmethacrylate), poly (hydroxystrene), poly(imide), poly(lactide), poly(L-lactic acid), poly(D, L-lactic acid), poly(lactide-co-glycolide), poly(lysine), poly(methacrylate), poly(methacrylic acid), poly(methylmethacrylate), poly(orthoester), poly(phenylene oxide), poly(phosphazene), poly(phosphoester), poly(propylene fumarate), poly(propylene), poly(propylene glycol), poly(propylene oxide), poly(styrene), poly(sulfone), poly (tetrafluoroethylene), poly(vinyl acetate), poly(vinyl alcohol), poly(vinyl chloride), poly(vinylidene fluoride), poly (vinyl pyrrolidone), poly(urethane), collagen, gelatin, any copolymer thereof (like poly(ethylene oxide) poly(propylene oxide) copolymers (poloxamers), poly(vinyl alcohol-co-ethylene), poly(styrene-co-allyl alcohol, and poly(ethylene)-block-poly(ethylene glycol), and/or any mixtures thereof.

A shell material may be comprised of a single material disclosed herein or a plurality of materials disclosed herein. In aspects of this embodiment, a shell material may comprise, e.g., at least two different materials disclosed herein, at least three different materials disclosed herein, at least four different materials disclosed herein, or at least five different materials disclosed herein. In aspects of this embodiment, a shell material may comprise, e.g., about 1 to about 2 different materials disclosed herein, about 1 to about 3 different materials disclosed herein, about 1 to about 4 different materials disclosed herein, about 1 to about 5 different materials disclosed herein, about 1 to about 6 different materials disclosed herein, about 2 to about 4 different materials disclosed herein, about 2 to about 5 different materials disclosed herein, about 2 to about 6 different materials disclosed herein, about 3 to about 4 different materials disclosed herein, about 3 to about 5 different materials disclosed herein, or about 3 to about 6 different materials disclosed herein.

A shell material has a thickness sufficient to allow formation of a porogen scaffold. As such, a shell material can be of any thickness, with the proviso that the amount of shell material is sufficient to create a porogen scaffold useful for its intended purpose. The thickness of the shell material is measured from the interior surface of the shell that is adjacent of the core material to the exterior surface of the shell.

Thus, in an embodiment, a porogen composition comprises a shell material. In an aspect of this embodiment, a porogen composition comprises a shell material having a melting point temperature that is lower than a melting point temperature of the core material. In aspects of this embodiment, a porogen composition comprises a shell material having a melting point temperature that is lower than a melting point temperature of the core material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a shell material having a melting point temperature that is lower than a melting point temperature of the core material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a shell material having a melting point temperature that is lower than a melting point temperature of the core material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In an aspect of this embodiment, a porogen composition comprises a shell material having a glass transition temperature that is lower than a glass transition temperature of the core material. In aspects of this embodiment, a porogen composition comprises a shell material having a glass transition temperature that is lower than a glass transition temperature of the core material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a shell material having a glass transition temperature that is lower than a glass transition temperature of the core material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a shell material having a glass transition temperature that is lower than a glass transition temperature of the core material by, e.g., about 5° C. to about 50° C., about 5° C. to about 75° C., about 5° C. to about 100° C., about 5° C. to about 200° C., about 5° C. to about 300° C., about 10° C. to about 50°

C., about 10° C. to about 75° C., about 10° C. to about 100° C., about 10° C. to about 200° C., or about 10° C. to about 300° C.

In another embodiment, a porogen composition comprises a shell material having a thickness sufficient to allow formation of a porogen scaffold. In aspects of this embodiment, a porogen composition comprises a shell material having a thickness of, e.g., about 1 µm, about 2 µm, about 3 µm, about 4 µm, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, or about 50 µm. In other aspects of this embodiment, a porogen composition comprises a shell material having a thickness of, e.g., at least 1 µm, at least 2 µm, at least 3 µm, at least 4 µm, at least 5 µm, at least 6 µm, at least 7 µm, at least 8 µm, at least 9 µm, at least 10 µm, at least 15 µm, at least 20 µm, at least 25 µm, at least 30 µm, at least 35 µm, at least 40 µm, at least 45 µm, or at least 50 µm. In yet other aspects of this embodiment, a porogen composition comprises a shell material having a thickness of, e.g., about 5 µm to about 50 µm, about 5 µm to about 75 µm, about 5 µm to about 100 µm, about 5 µm to about 200 µm, about 5 µm to about 300 µm, about 10 µm to about 50 µm, about 10 µm to about 75 µm, about 10 µm to about 100 µm, about 10 µm to about 200 µm, about 10 µm to about 300 µm, about 15 µm to about 50 µm, about 15 µm to about 75 µm, about 15 µm to about 100 µm, about 15 µm to about 200 µm, about 15 µm to about 300 µm, about 25 µm to about 50 µm, about 25 µm to about 75 µm, about 25 µm to about 100 µm, about 25 µm to about 200 µm, about 25 µm to about 300 µm, about 35 µm to about 50 µm, about 35 µm to about 75 µm, about 35 µm to about 100 µm, about 35 µm to about 200 µm, or about 35 µm to about 300 µm.

In another embodiment, a shell material comprises an inorganic material. In another embodiment, a shell material comprises an organic material. In another embodiment, a shell material comprises a salt and/or its derivatives, a ceramic and/or its derivatives, a sugar and/or its derivatives, a polysaccharide and/or its derivatives, a wax and/or its derivatives, a metal and/or its derivatives, a surfactant and/or its derivatives, a water soluble solid and/or its derivatives, or a polymer and/or its derivatives.

The present specification discloses, in part, a porogen comprising a core material. A core material of a porogen can be made of any material with the proviso that 1) the melting point temperature (Tm) of the core material is higher than the melting point temperature of the shell material; and/or 2) the glass transition temperature (Tg) of the core material is higher than the glass transition temperature of the shell material. A core material can be of any shape, with the proviso that the shape is useful to create a porogen scaffold. Useful core shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

A core material has a thickness sufficient to allow formation of a porogen scaffold. As such, a core material can be of any thickness, with the proviso that the amount of core material is sufficient to create a porogen scaffold useful for its intended purpose. The thickness of a core material can be measured base on its shape. For example, for triangular cores, quadrilateral cores, and any other type of polygonal shape, thickness is measured based on the base width of the core material. For example, for sided-shaped cores, like polyhedrons, triangles, pyramids, quadrilateral, or polygons, thickness is measured based on the base width of the core.

A core material can comprise a natural or synthetic, inorganic or organic material. Exemplary materials suitable as a core material disclosed herein, include, without limitation, natural and synthetic salts and its derivatives, natural and synthetic ceramics and/or its derivatives, natural and synthetic sugars and its derivatives, natural and synthetic polysaccharides and its derivatives, natural and synthetic waxes and its derivatives, natural and synthetic metals and its derivatives, natural and synthetic organic solids and its derivatives, natural and synthetic water soluble solids and its derivatives, and/or natural and synthetic polymers and its derivatives, composites thereof, and/or combinations thereof. Exemplary materials suitable as a core material are described above in the present specification.

A core material may be comprised of a single material disclosed herein or a plurality of materials disclosed herein. In aspects of this embodiment, a core material may comprise, e.g., at least two different materials disclosed herein, at least three different materials disclosed herein, at least four different materials disclosed herein, or at least five different materials disclosed herein. In aspects of this embodiment, a core material may comprise, e.g., about 1 to about 2 different materials disclosed herein, about 1 to about 3 different materials disclosed herein, about 1 to about 4 different materials disclosed herein, about 1 to about 5 different materials disclosed herein, about 1 to about 6 different materials disclosed herein, about 2 to about 4 different materials disclosed herein, about 2 to about 5 different materials disclosed herein, about 2 to about 6 different materials disclosed herein, about 3 to about 4 different materials disclosed herein, about 3 to about 5 different materials disclosed herein, or about 3 to about 6 different materials disclosed herein.

Thus, in an embodiment, a porogen composition comprises a core material. In an aspect of this embodiment, a porogen composition comprises a core material having a melting point temperature that is higher than a melting point temperature of the shell material. In aspects of this embodiment, a porogen composition comprises a core material having a melting point temperature that is higher than a melting point temperature of the shell material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a core material having a melting point temperature that is higher than a melting point temperature of the shell material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a core material having a melting point temperature that is higher than a melting point temperature of the shell material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In an aspect of this embodiment, a porogen composition comprises a core material having a glass transition temperature that is higher than a glass transition temperature of the shell material. In aspects of this embodiment, a porogen composition comprises a core material having a glass transition temperature that is higher than a glass transition temperature of the shell material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a core material having a glass transition temperature that is higher than a glass transition temperature of the shell material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a core material having a glass transition temperature that is higher than a glass transition temperature of the shell material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In another embodiment, a porogen composition comprises a core material having a thickness sufficient to allow formation of a porogen scaffold. In aspects of this embodiment, a porogen composition comprises a core material having a thickness of, e.g., about 10 µm, about 20 µm, about 30 µm, about 40 µm, about 50 µm, about 60 µm, about 70 µm, about 80 µm, about 90 µm, about 100 µm, about 200 µm, about 300 µm, about 400 µm, about 500 µm, about 600 µm, about 700 µm, about 800 µm, or about 900 µm. In other aspects of this embodiment, a porogen composition comprises a shell material having a thickness of, e.g., at least 10 µm, at least 20 µm, at least 30 µm, at least 40 µm, at least 50 µm, at least 60 µm, at least 70 µm, at least 80 µm, at least 90 µm, at least 100 µm, at least 200 µm, at least 300 µm, at least 400 µm, at least 500 µm, at least 600 µm, at least 700 µm, at least 800 µm, or at least 900 µm. In yet other aspects of this embodiment, a porogen composition comprises a shell material having a thickness of, e.g., about 10 µm to about 500 µm, about 10 µm to about 750 µm, about 10 µm to about 1000 µm, about 10 µm to about 2000 µm, about 10 µm to about 3000 µm, about 25 µm to about 500 µm, about 25 µm to about 750 µm, about 25 µm to about 1000 µm, about 25 µm to about 2000 µm, about 25 µm to about 3000 µm, about 50 µm to about 500 µm, about 50 µm to about 750 µm, about 50 µm to about 1000 µm, about 50 µm to about 2000 µm, about 50 µm to about 3000 µm, about 100 µm to about 500 µm, about 100 µm to about 750 µm, about 100 µm to about 1000 µm, about 100 µm to about 2000 µm, or about 100 µm to about 3000 µm.

In another embodiment, a core material comprises an inorganic material. In another embodiment, a core material comprises an organic material. In another embodiment, a core material comprises a salt and/or its derivatives, a ceramic and/or its derivatives, a sugar and/or its derivatives, a polysaccharide and/or its derivatives, a wax and/or its derivatives, a metal and/or its derivatives, a water soluble solid and/or its derivatives, or a polymer and/or its derivatives.

The present specification discloses, in part, a porogen comprising a shell material and a core material, where the core material has a higher melting point temperature or glass transition temperature relative to the melting point temperature or the glass transition temperature of the shell material. The melting point temperature or glass transition temperature of any of the shell and core materials is well known to a person of ordinary skill and is publicly available information. See, e.g., Polymer Physics, pp. 454 (Ed. Michael Rubinstein, Edmund T. Rolls, Ralph H. Colby, Oxford University Press, 2003); Inorganic Chemistry, pp. 822 (Ed. Peter Atkins, Duward F. Shriver, Tina Overton, Jonathan Rourke, W.H. Freeman, 2006); and Carbohydrate Chemistry, pp. 96 (B. G. Davis and A. J. Fairbanks, Oxford University Press 2002), each of which is incorporated by reference in its entirety.

In another embodiment, a porogen comprises a shell material comprising an inorganic material and a core material comprising an inorganic material, where the core material has a higher melting point temperature or glass transition temperature relative to the melting point temperature or the glass transition temperature of the shell material. In another embodiment, a porogen comprises a shell material comprising an organic material and a core material comprising an inorganic material, where the core material has a higher melting point temperature or glass transition temperature relative to the melting point temperature or the glass transition temperature of the shell material. In another embodiment, a porogen comprises a shell material comprising an inorganic material and a core material comprising an organic material, where the core material has a higher melting point temperature or glass transition temperature relative to the melting point temperature or the glass transition temperature of the shell material. In another embodiment, a porogen comprises a shell material comprising an organic material and a core material comprising an organic material, where the core material has a higher melting point temperature or glass transition temperature relative to the melting point temperature or the glass transition temperature of the shell material.

In another embodiment, a porogen comprises a shell material comprising a salt and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a salt and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a ceramic and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a sugar and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a polysaccharide and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a wax and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a metal and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a water-soluble solid and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a polymer and/or its derivatives, where the core material has a higher melting point temperature or glass transition temperature relative to the melting point temperature or the glass transition temperature of the shell material.

Aspects of the present specification disclose, in part, a porogen comprising a core material and shell material where the shell material is fusible and the core material is non-fusible under a given physical or physicochemical treatment. As used herein, the term "under a given physical or physicochemical treatment" refers to a physical or physicochemical treatment that permits the shell material to transition from its solid phase to its liquid phase, but maintains the core material in its solid phase.

Thus, in an embodiment, a porogen comprises a shell material comprising an inorganic material and a core material comprising an inorganic material, where under a given physical or physicochemical treatment the shell material is fusible and the core material is non-fusible. In another embodiment, a porogen comprises a shell material comprising an organic material and a core material comprising an inorganic material, where under a given physical or physicochemical treatment the shell material is fusible and the core material is non-fusible. In another embodiment, a porogen comprises a shell material comprising an inorganic material and a core material comprising an organic material, where under a given physical or physicochemical treatment the shell material is fusible and the core material is non-fusible. In another embodiment, a porogen comprises a shell material comprising an organic material and a core material comprising an organic material, where under a given physical or physicochemical treatment the shell material is fusible and the core material is non-fusible.

In another embodiment, a porogen comprises a shell material comprising a salt and/or its derivatives and a core material comprising a salt and/or its derivatives, where under a given physical or physicochemical treatment the shell material is fusible and the core material is non-fusible. In another embodiment, a porogen comprises a shell material comprising a ceramic and/or its derivatives and a core material comprising a salt and/or its derivatives, where under a given physical or physicochemical treatment the shell material is fusible and the core material is non-fusible. In another embodiment, a porogen comprises a shell material comprising a sugar and/or its derivatives and a core material comprising a salt and/or its derivatives, where under a given physical or physicochemical treatment the shell material is fusible and the core material is non-fusible. In another embodiment, a porogen comprises a shell material comprising a polysaccharide and/or its derivatives and a core material comprising a salt and/or its derivatives, where under a given physical or physicochemical treatment the shell material is fusible and the core material is non-fusible. In another embodiment, a porogen comprises a shell material comprising a wax and/or its derivatives and a core material comprising a salt and/or its derivatives, where under a given physical or physicochemical treatment the shell material is fusible and the core material is non-fusible. In another embodiment, a porogen comprises a shell material comprising a metal and/or its derivatives and a core material comprising a salt and/or its derivatives, where under a given physical or physicochemical treatment the shell material is fusible and the core material is non-fusible. In another embodiment, a porogen comprises a shell material comprising a surfactant and/or its derivatives and a core material comprising a salt and/or its derivatives, where under a given physical or physicochemical treatment the shell material is fusible and the core material is non-fusible. In another embodiment, a porogen comprises a shell material comprising a water-soluble solid and/or its derivatives and a core material comprising a salt and/or its derivatives, where under a given physical or physicochemical treatment the shell material is fusible and the core material is non-fusible. In another embodiment, a porogen comprises a shell material comprising a polymer and/or its derivatives and a core material comprising a salt and/or its derivatives, where under a given physical or physicochemical treatment the shell material is fusible and the core material is non-fusible.

In another embodiment, a porogen comprises a shell material comprising a salt and/or its derivatives and a core material comprising a ceramic and/or its derivatives, where under a given physical or physicochemical treatment the shell material is fusible and the core material is non-fusible. In another embodiment, a porogen comprises a shell material comprising a ceramic and/or its derivatives and a core material comprising a ceramic and/or its derivatives, where under a given physical or physicochemical treatment the shell material is fusible and the core material is non-fusible. In another embodiment, a porogen comprises a shell material comprising a sugar and/or its derivatives and a core material comprising a ceramic and/or its derivatives, where under a given physical or physicochemical treatment the shell material is fusible and the core material is non-fusible. In another embodiment, a porogen comprises a shell material comprising a polysaccharide and/or its derivatives and a core material comprising a ceramic and/or its derivatives, where under a given physical or physicochemical treatment the shell material is fusible and the core material is non-fusible. In another embodiment, a porogen comprises a shell material comprising a wax and/or its derivatives and a core material comprising a ceramic and/or its derivatives, where under a given physical or physicochemical treatment the shell material is fusible and the core material is non-fusible. In another embodiment, a porogen comprises a shell material comprising a metal and/or its derivatives and a core material comprising a ceramic and/or its derivatives, where under a given physical or physicochemical treatment the shell material is fusible and the core material is non-fusible. In another embodiment, a porogen comprises a shell material comprising a surfactant and/or its derivatives and a core material comprising a ceramic and/or its derivatives, where under a given physical or physicochemical treatment the shell material is fusible and the core material is non-fusible. In another embodiment, a porogen comprises a shell material comprising a water-soluble solid and/or its derivatives and a core material comprising a ceramic and/or its derivatives, where under a given physical or physicochemical treatment the shell material is fusible and the core material is non-fusible. In another embodiment, a porogen comprises a shell material comprising a polymer and/or its derivatives and a core material comprising a ceramic and/or its derivatives, where under a given physical or physicochemical treatment the shell material is fusible and the core material is non-fusible.

In another embodiment, a porogen comprises a shell material comprising a salt and/or its derivatives and a core material comprising a sugar and/or its derivatives, where under a given physical or physicochemical treatment the shell material is fusible and the core material is non-fusible. In another embodiment, a porogen comprises a shell material comprising a ceramic and/or its derivatives and a core material comprising a sugar and/or its derivatives, where under a given physical or physicochemical treatment the shell material is fusible and the core material is non-fusible. In another embodiment, a porogen comprises a shell material comprising a sugar and/or its derivatives and a core material comprising a sugar and/or its derivatives, where under a given physical or physicochemical treatment the shell material is fusible and the core material is non-fusible. In another embodiment, a porogen comprises a shell material comprising a polysaccharide and/or its derivatives and a core material comprising a sugar and/or its derivatives, where under a given physical or physicochemical treatment the shell material is fusible and the core material is non-fusible. In another embodiment, a porogen comprises a shell material comprising a wax and/or its derivatives and a core material comprising a sugar and/or its derivatives, where under a given physical or physicochemical treatment the shell material is fusible and the core material is non-fusible. In another embodiment, a porogen comprises a shell material comprising a metal and/or its derivatives and a core material comprising a sugar and/or its derivatives, where under a given physical or physicochemical treatment the shell material is fusible and the core material is non-fusible. In another embodiment, a porogen comprises a shell material comprising a surfactant and/or its derivatives and a core material comprising a sugar and/or its derivatives, where under a given physical or physicochemical treatment the shell material is fusible and the core material is non-fusible. In another embodiment, a porogen comprises a shell material comprising a water-soluble solid and/or its derivatives and a core material comprising a sugar and/or its derivatives, where under a given physical or physicochemical treatment the shell material is fusible and the core material is non-fusible. In another embodiment, a porogen comprises a shell material comprising a polymer and/or its derivatives and a core material comprising a sugar and/or its derivatives, where under a given physical or physicochemical treatment the shell material is fusible and the core material is non-fusible.

In another embodiment, a porogen comprises a shell material comprising a salt and/or its derivatives and a core material comprising a polysaccharide and/or its derivatives, where under a given physical or physicochemical treatment the shell material is fusible and the core material is non-fusible. In another embodiment, a porogen comprises a shell material comprising a ceramic and/or its derivatives and a core material comprising a polysaccharide and/or its derivatives, where under a given physical or physicochemical treatment the shell material is fusible and the core material is non-fusible. In another embodiment, a porogen comprises a shell material comprising a sugar and/or its derivatives and a core material comprising a polysaccharide and/or its derivatives, where under a given physical or physicochemical treatment the shell material is fusible and the core material is non-fusible. In another embodiment, a porogen comprises a shell material comprising a polysaccharide and/or its derivatives and a core material comprising a polysaccharide and/or its derivatives, where under a given physical or physicochemical treatment the shell material is fusible and the core material is non-fusible. In another embodiment, a porogen comprises a shell material comprising a wax and/or its derivatives and a core material comprising a polysaccharide and/or its derivatives, where under a given physical or physicochemical treatment the shell material is fusible and the core material is non-fusible. In another embodiment, a porogen comprises a shell material comprising a metal and/or its derivatives and a core material comprising a polysaccharide and/or its derivatives, where under a given physical or physicochemical treatment the shell material is fusible and the core material is non-fusible. In another embodiment, a porogen comprises a shell material comprising a surfactant and/or its derivatives and a core material comprising a polysaccharide and/or its derivatives, where under a given physical or physicochemical treatment the shell material is fusible and the core material is non-fusible. In another embodiment, a porogen comprises a shell material comprising a water-soluble solid and/or its derivatives and a core material comprising a polysaccharide and/or its derivatives, where under a given physical or physicochemical treatment the shell material is fusible and the core material is non-fusible. In another embodiment, a porogen comprises a shell material comprising a polymer and/or its derivatives and a core material comprising a polysaccharide and/or its derivatives, where under a given physical or physicochemical treatment the shell material is fusible and the core material is non-fusible.

In another embodiment, a porogen comprises a shell material comprising a salt and/or its derivatives and a core material comprising a wax and/or its derivatives, where under a given physical or physicochemical treatment the shell material is fusible and the core material is non-fusible. In another embodiment, a porogen comprises a shell material comprising a ceramic and/or its derivatives and a core material comprising a wax and/or its derivatives, where under a given physical or physicochemical treatment the shell material is fusible and the core material is non-fusible. In another embodiment, a porogen comprises a shell material comprising a sugar and/or its derivatives and a core material comprising a wax and/or its derivatives, where under a given physical or physicochemical treatment the shell material is fusible and the core material is non-fusible. In another embodiment, a porogen comprises a shell material comprising a polysaccharide and/or its derivatives and a core material comprising a wax and/or its derivatives, where under a given physical or physicochemical treatment the shell material is fusible and the core material is non-fusible. In another embodiment, a porogen comprises a shell material comprising a wax and/or its derivatives and a core material comprising a wax and/or its derivatives, where under a given physical or physicochemical treatment the shell material is fusible and the core material is non-fusible. In another embodiment, a porogen comprises a shell material comprising a metal and/or its derivatives and a core material comprising a wax and/or its derivatives, where under a given physical or physicochemical treatment the shell material is fusible and the core material is non-fusible. In another embodiment, a porogen comprises a shell material comprising a surfactant and/or its derivatives and a core material comprising a wax and/or its derivatives, where under a given physical or physicochemical treatment the shell material is fusible and the core material is non-fusible. In another embodiment, a porogen comprises a shell material comprising a water-soluble solid and/or its derivatives and a core material comprising a wax and/or its derivatives, where under a given physical or physicochemical treatment the shell material is fusible and the core material is non-fusible. In another embodiment, a porogen comprises a shell material comprising a polymer and/or its derivatives and a core material comprising a wax and/or its derivatives, where under a given physical or physicochemical treatment the shell material is fusible and the core material is non-fusible.

In another embodiment, a porogen comprises a shell material comprising a salt and/or its derivatives and a core material comprising a metal and/or its derivatives, where under a given physical or physicochemical treatment the shell material is fusible and the core material is non-fusible. In another embodiment, a porogen comprises a shell material comprising a ceramic and/or its derivatives and a core material comprising a metal and/or its derivatives, where under a given physical or physicochemical treatment the shell material is fusible and the core material is non-fusible. In another embodiment, a porogen comprises a shell material comprising a sugar and/or its derivatives and a core material comprising a metal and/or its derivatives, where under a given physical or physicochemical treatment the shell material is fusible and the core material is non-fusible. In another embodiment, a porogen comprises a shell material comprising a polysaccharide and/or its derivatives and a core material comprising a metal and/or its derivatives, where under a given physical or physicochemical treatment the shell material is fusible and the core material is non-fusible. In another embodiment, a porogen comprises a shell material comprising a wax and/or its derivatives and a core material comprising a metal and/or its derivatives, where under a given physical or physicochemical treatment the shell material is fusible and the core material is non-fusible. In another embodiment, a porogen comprises a shell material comprising a metal and/or its derivatives and a core material comprising a metal and/or its derivatives, where under a given physical or physicochemical treatment the shell material is fusible and the core material is non-fusible. In another embodiment, a porogen comprises a shell material comprising a surfactant and/or its derivatives and a core material comprising a metal and/or its derivatives, where under a given physical or physicochemical treatment the shell material is fusible and the core material is non-fusible. In another embodiment, a porogen comprises a shell material comprising a water-soluble solid and/or its derivatives and a core material comprising a metal and/or its derivatives, where under a given physical or physicochemical treatment the shell material is fusible and the core material is non-fusible. In another embodiment, a porogen comprises a shell material comprising a polymer and/or its derivatives and a core material comprising a metal and/or its derivatives, where under a given physical or physicochemical treatment the shell material is fusible and the core material is non-fusible.

In another embodiment, a porogen comprises a shell material comprising a salt and/or its derivatives and a core material comprising a water-soluble solid and/or its derivatives, where under a given physical or physicochemical treatment the shell material is fusible and the core material is non-fusible. In another embodiment, a porogen comprises a shell material comprising a ceramic and/or its derivatives and a core material comprising a water-soluble solid and/or its derivatives, where under a given physical or physicochemical treatment the shell material is fusible and the core material is non-fusible. In another embodiment, a porogen comprises a shell material comprising a sugar and/or its derivatives and a core material comprising a water-soluble solid and/or its derivatives, where under a given physical or physicochemical treatment the shell material is fusible and the core material is non-fusible. In another embodiment, a porogen comprises a shell material comprising a polysaccharide and/or its derivatives and a core material comprising a water-soluble solid and/or its derivatives, where under a given physical or physicochemical treatment the shell material is fusible and the core material is non-fusible. In another embodiment, a porogen comprises a shell material comprising a wax and/or its derivatives and a core material comprising a water-soluble solid and/or its derivatives, where under a given physical or physicochemical treatment the shell material is fusible and the core material is non-fusible. In another embodiment, a porogen comprises a shell material comprising a metal and/or its derivatives and a core material comprising a water-soluble solid and/or its derivatives, where under a given physical or physicochemical treatment the shell material is fusible and the core material is non-fusible. In another embodiment, a porogen comprises a shell material comprising a surfactant and/or its derivatives and a core material comprising a water-soluble solid and/or its derivatives, where under a given physical or physicochemical treatment the shell material is fusible and the core material is non-fusible. In another embodiment, a porogen comprises a shell material comprising a water-soluble solid and/or its derivatives and a core material comprising a water-soluble solid and/or its derivatives, where under a given physical or physicochemical treatment the shell material is fusible and the core material is non-fusible. In another embodiment, a porogen comprises a shell material comprising a polymer and/or its derivatives and a core material comprising a water-soluble solid and/or its derivatives, where under a given physical or physicochemical treatment the shell material is fusible and the core material is non-fusible.

In another embodiment, a porogen comprises a shell material comprising a salt and/or its derivatives and a core material comprising a polymer and/or its derivatives, where under a given physical or physicochemical treatment the shell material is fusible and the core material is non-fusible. In another embodiment, a porogen comprises a shell material comprising a ceramic and/or its derivatives and a core material comprising a polymer and/or its derivatives, where under a given physical or physicochemical treatment the shell material is fusible and the core material is non-fusible. In another embodiment, a porogen comprises a shell material comprising a sugar and/or its derivatives and a core material comprising a polymer and/or its derivatives, where under a given physical or physicochemical treatment the shell material is fusible and the core material is non-fusible. In another embodiment, a porogen comprises a shell material comprising a polysaccharide and/or its derivatives and a core material comprising a polymer and/or its derivatives, where under a given physical or physicochemical treatment the shell material is fusible and the core material is non-fusible. In another embodiment, a porogen comprises a shell material comprising a wax and/or its derivatives and a core material comprising a polymer and/or its derivatives, where under a given physical or physicochemical treatment the shell material is fusible and the core material is non-fusible. In another embodiment, a porogen comprises a shell material comprising a metal and/or its derivatives and a core material comprising a polymer and/or its derivatives, where under a given physical or physicochemical treatment the shell material is fusible and the core material is non-fusible. In another embodiment, a porogen comprises a shell material comprising a surfactant and/or its derivatives and a core material comprising a polymer and/or its derivatives, where under a given physical or physicochemical treatment the shell material is fusible and the core material is non-fusible. In another embodiment, a porogen comprises a shell material comprising a water-soluble solid and/or its derivatives and a core material comprising a polymer and/or its derivatives, where under a given physical or physicochemical treatment the shell material is fusible and the core material is non-fusible. In another embodiment, a porogen comprises a shell material comprising a polymer and/or its derivatives and a core material comprising a polymer and/or its derivatives, where under a given physical or physicochemical treatment the shell material is fusible and the core material is non-fusible.

In another embodiment, a porogen comprises a core having a mean diameter of about 200 µm to about 700 µm and a shell having a mean thickness of about 30 µm to about 70 µm. In an aspect of this embodiment, a porogen comprises a core comprising sugar and starch and having a mean diameter of about 200 µm to about 700 µm and a shell comprising PEG and having a mean thickness of about 30 µm to about 70 µm. In another aspect of this embodiment, a porogen comprises a core comprising sugar and starch and having a mean diameter of about 200 µm to about 650 µm and a shell comprising PEG and having a mean thickness of about 30 µm to about 70 µm. In yet another aspect of this embodiment, a porogen comprises a core comprising about 65% to about 85% sugar and about 15% to about 35% starch and having a mean diameter of about 200 µm to about 650 µm and a shell comprising PEG of about 2,000 Da to about 15,000 Da and having a mean thickness of about 30 µm to about 70 µm. In still another aspect of this embodiment, a porogen comprises a core comprising about 75% sugar and about 25% starch and having a mean diameter of about 200 µm to about 650 µm and a shell comprising PEG of about 8,000 Da and having a mean thickness of about 30 µm to about 70 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core having a mean diameter of about 200 µm to about 450 µm and a shell having a mean thickness of about 35 µm to about 65 µm. In another aspect of this embodiment, a porogen comprises a core having a mean diameter of about 250 µm to about 420 µm and a shell having a mean thickness of about 40 µm to about 60 µm. In yet another aspect of this embodiment, a porogen comprises a core having a mean diameter of about 400 µm and a shell having a mean thickness of about 50 µm. In another aspect of this embodiment, a porogen comprises a core having a mean diameter of about 350 µm and a shell having a mean thickness of about 50 µm.

In an aspect of this embodiment, a porogen comprises a core comprising sugar and starch and having a mean diameter of about 200 µm to about 450 µm and a shell comprising PEG and having a mean thickness of about 35 µm to about 65 µm. In another aspect of this embodiment, a porogen comprises a core comprising sugar and starch and having a mean diameter of about 250 µm to about 420 µm and a shell comprising PEG and having a mean thickness of about 40 µm to about 60 µm. In yet another aspect of this embodiment, a porogen comprises a core comprising sugar and starch and having a mean diameter of about 400 µm and a shell comprising PEG and having a mean thickness of about 50 µm. In another aspect of this embodiment, a porogen comprises a core comprising sugar and starch and having a mean diameter of about 350 µm and a shell comprising PEG and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core comprising about 65% to about 85% sugar and about 15% to about 35% starch and having a mean diameter of about 200 µm to about 450 µm and a shell comprising PEG of about 2,000 Da to about 15,000 Da and having a mean thickness of about 35 µm to about 65 µm. In another aspect of this embodiment, a porogen comprises a core comprising about 65% to about 85% sugar and about 15% to about 35% starch and having a mean diameter of about 250 µm to about 420 µm and a shell comprising PEG of about 2,000 Da to about 15,000 Da and having a mean thickness of about 40 µm to about 60 µm. In yet another aspect of this embodiment, a porogen comprises a core comprising about 65% to about 85% sugar and about 15% to about 35% starch and having a mean diameter of about 400 µm and a shell comprising PEG of about 2,000 Da to about 15,000 Da and having a mean thickness of about 50 µm. In another aspect of this embodiment, a porogen comprises a core comprising about 65% to about 85% sugar and about 15% to about 35% starch and having a mean diameter of about 350 µm and a shell comprising PEG of about 2,000 Da to about 15,000 Da and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core comprising about 75% sugar and about 25% starch and having a mean diameter of about 200 µm to about 450 µm and a shell comprising PEG of about 8,000 Da and having a mean thickness of about 35 µm to about 65 µm. In another aspect of this embodiment, a porogen comprises a core comprising about 75% sugar and about 25% starch and having a mean diameter of about 250 µm to about 420 µm and a shell comprising PEG of about 8,000 Da and having a mean thickness of about 40 µm to about 60 µm. In yet another aspect of this embodiment, a porogen comprises a core comprising about 75% sugar and about 25% starch and having a mean diameter of about 400 µm and a shell comprising PEG of about 8,000 Da and having a mean thickness of about 50 µm. In another aspect of this embodiment, a porogen comprises a core comprising about 75% sugar and about 25% starch and having a mean diameter of about 350 µm and a shell comprising PEG of about 8,000 Da and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core having a mean diameter of about 400 µm to about 650 µm and a shell having a mean thickness of about 35 µm to about 65 µm. In another aspect of this embodiment, a porogen comprises a core having a mean diameter of about 420 µm to about 500 µm and a shell material having a mean thickness of about 40 µm to about 60 µm. In yet another aspect of this embodiment, a porogen comprises a core having a mean diameter of about 500 µm and a shell having a mean thickness of about 50 µm. In another aspect of this embodiment, a porogen comprises a core having a mean diameter of about 450 µm and a shell having a mean thickness of about 50 µm.

In an aspect of this embodiment, a porogen comprises a core comprising sugar and starch and having a mean diameter of about 400 µm to about 650 µm and a shell comprising PEG and having a mean thickness of about 35 µm to about 65 µm. In another aspect of this embodiment, a porogen comprises a core comprising sugar and starch and having a mean diameter of about 420 µm to about 500 µm and a shell comprising PEG and having a mean thickness of about 40 µm to about 60 µm. In yet another aspect of this embodiment, a porogen comprises a core comprising sugar and starch and having a mean diameter of about 500 µm and a shell comprising PEG and having a mean thickness of about 50 µm. In another aspect of this embodiment, a porogen comprises a core comprising sugar and starch and having a mean diameter of about 450 µm and a shell comprising PEG and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core comprising about 65% to about 85% sugar and about 15% to about 35% starch and having a mean diameter of about 400 µm to about 650 µm and a shell comprising PEG of about 2,000 Da to about 15,000 Da and having a mean thickness of about 35 µm to about 65 µm. In another aspect of this embodiment, a porogen comprises a core comprising about 65% to about 85% sugar and about 15% to about 35% starch and having a mean diameter of about 420 µm to about 500 µm and a shell comprising PEG of about 2,000 Da to about 15,000 Da and having a mean thickness of about 40 µm to about 60 µm. In yet another aspect of this embodiment, a porogen comprises a core comprising about 65% to about 85% sugar and about 15% to about 35% starch and having a mean diameter of about 500 µm and a shell comprising PEG of about 2,000 Da to about 15,000 Da and having a mean thickness of about 50 µm. In another aspect of this embodiment, a porogen comprises a core comprising about 65% to about 85% sugar and about 15% to about 35% starch and having a mean diameter of about 450 µm and a shell comprising PEG of about 2,000 Da to about 15,000 Da and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core comprising about 75% sugar and about 25% starch and having a mean diameter of about 400 µm to about 650 µm and a shell comprising PEG of about 8,000 Da and having a mean thickness of about 35 µm to about 65 µm. In another aspect of this embodiment, a porogen comprises a core comprising about 75% sugar and about 25% starch and having a mean diameter of about 420 µm to about 500 µm and a shell comprising PEG of about 8,000 Da and having a mean thickness of about 40 µm to about 60 µm. In yet another aspect of this embodiment, a porogen comprises a core comprising about 75% sugar and about 25% starch and having a mean diameter of about 500 µm and a shell comprising PEG of about 8,000 Da and having a mean thickness of about 50 µm. In another aspect of this embodiment, a porogen comprises a core comprising about 75% sugar and about 25% starch and having a mean diameter of about 450 µm and a shell comprising PEG of about 8,000 Da and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core having a mean diameter of about 500 µm to about 750 µm and a shell having a mean thickness of about 35 µm to about 65 µm. In another aspect of this embodiment, a porogen comprises a core having a mean diameter of about 500 µm to about 600 µm and a shell having a mean thickness of about 40 µm to about 60 µm. In yet another aspect of this embodiment, a porogen comprises a core having a mean diameter of about 600 µm and a shell having a mean thickness of about 50 µm. In another aspect of this embodiment, a porogen comprises a core having a mean diameter of about 550 µm and a shell having a mean thickness of about 50 µm.

In an aspect of this embodiment, a porogen comprises a core comprising sugar and starch and having a mean diameter of about 500 µm to about 750 µm and a shell comprising PEG and having a mean thickness of about 35 µm to about 65 µm. In another aspect of this embodiment, a porogen comprises a core comprising sugar and starch and having a mean diameter of about 500 µm to about 600 µm and a shell comprising PEG and having a mean thickness of about 40 µm to about 60 µm. In yet another aspect of this embodiment, a porogen comprises a core comprising sugar and starch and having a mean diameter of about 600 µm and a shell comprising PEG and having a mean thickness of about 50 µm. In another aspect of this embodiment, a porogen comprises a core comprising sugar and starch and having a mean diameter of about 550 µm and a shell comprising PEG and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core comprising about 65% to about 85% sugar and about 15% to about 35% starch and having a mean diameter of about 500 µm to about 750 µm and a shell comprising PEG of about 2,000 Da to about 15,000 Da and having a mean thickness of about 35 µm to about 65 µm. In another aspect of this embodiment, a porogen comprises a core comprising about 65% to about 85% sugar and about 15% to about 35% starch and having a mean diameter of about 500 µm to about 600 µm and a shell comprising PEG of about 2,000 Da to about 15,000 Da and having a mean thickness of about 40 µm to about 60 µm. In yet another aspect of this embodiment, a porogen comprises a core comprising about 65% to about 85% sugar and about 15% to about 35% starch and having a mean diameter of about 600 µm and a shell comprising PEG of about 2,000 Da to about 15,000 Da and having a mean thickness of about 50 µm. In another aspect of this embodiment, a porogen comprises a core comprising about 65% to about 85% sugar and about 15% to about 35% starch and having a mean diameter of about 550 µm and a shell comprising PEG of about 2,000 Da to about 15,000 Da and having a mean thickness of about 50 µm. In other aspects of this embodiment, the sugar is a monosaccharide, a disaccharide or a trisaccharide. In other aspects of this embodiment, the disaccharide is sucrose.

In an aspect of this embodiment, a porogen comprises a core comprising about 75% sugar and about 25% starch and having a mean diameter of about 500 µm to about 750 µm and a shell comprising PEG of about 8,000 Da and having a mean thickness of about 35 µm to about 65 µm. In another aspect of this embodiment, a porogen comprises a core comprising about 75% sugar and about 25% starch and having a mean diameter of about 500 µm to about 600 µm and a shell comprising PEG of about 8,000 Da and having a mean thickness of about 40 µm to about 60 µm. In yet another aspect of this embodiment, a porogen comprises a core comprising about 75% sugar and about 25% starch and having a mean diameter of about 600 µm and a shell comprising PEG of about 8,000 Da and having a mean thickness of about 50 µm. In another aspect of this embodiment, a porogen comprises a core comprising about 75% sugar and about 25% starch and having a mean diameter of about 550 µm and a shell comprising PEG of about 8,000 Da and having a mean thickness of about 50 µm. In other aspects of this embodiment, the sugar is a monosaccharide, a disaccharide or a trisaccharide. In other aspects of this embodiment, the disaccharide is sucrose.

In another embodiment, a porogen disclosed herein comprises a core including sugar and starch and a shell including PEG. In an aspect of this embodiment, a porogen disclosed herein comprises a core including sugar and starch and a shell including PEG wherein the amount of sugar in the porogen is about 35% to about 50%, the amount of starch in the porogen is about 10% to about 15%, and the amount of PEG in the porogen is about 35% to about 50%. In an aspect of this embodiment, a porogen disclosed herein comprises a core including sugar and starch and a shell including PEG wherein the amount of sugar in the porogen is about 40% to about 45%, the amount of starch in the porogen is about 10% to about 15%, and the amount of PEG in the porogen is about 40% to about 50%. In another aspect of this embodiment, a porogen disclosed herein comprises a core including sugar and starch and a shell including PEG wherein the amount of sugar in the porogen is about 45%, the amount of starch in the porogen is about 10%, and the amount of PEG in the porogen is about 45%. In yet another aspect of this embodiment, a porogen disclosed herein comprises a core including sugar and starch and a shell including PEG wherein the amount of sugar in the porogen is about 45%, the amount of starch in the porogen is about 11%, and the amount of PEG in the porogen is about 44%. In still another aspect of this embodiment, a porogen disclosed herein comprises a core including sugar and starch and a shell including PEG wherein the amount of sugar in the porogen is about 40%, the amount of starch in the porogen is about 15%, and the amount of PEG in the porogen is about 45%.

The present specification discloses methods of making a porogen composition.

In one aspect, methods of making a porogen composition comprise the steps of: a) forming a particle out of a core material; and b) coating the particle with a shell material.

The present specification discloses, in part, forming a particle out of a core material. Suitable core materials are as described above. Forming a particle out of a core material can be accomplished by any suitable means, including, without limitation, pelletization by fluidized bed granulation, rotor granulation, or extrusion-spheronization; grinding by roller mills and sieving; solvent evaporation; or emulsion. Suitable particles of a core material are also commercially available from, e.g., Fisher Scientific (Pittsburgh, Pa.), Boehringer Ingelheim Pharmaceuticals, Inc. (Ridgefield, Conn.); and Paulaur Corp., (Cranbury, N. J.).

The present specification discloses, in part, coating a particle with a shell material. Suitable shell materials are as described above. Coating a particle with a shell material can be accomplished by any suitable means, including, without limitation, mechanical application such as, e.g., dipping, spraying, filtration, knifing, curtaining, brushing, or vapor deposition; physical adsorption application; thermal application; fluidization application; adhering application; chemical bonding application; self-assembling application; molecular entrapment application, and/or any combination thereof. The shell material is applied to the particle of core material in such a manner as to coat the particle with the desired thickness of shell material. Removal of excess shell material can be accomplished by any suitable means, including, without limitation, gravity-based filtering or sieving, vacuum-based filtering or sieving, blowing, and/or any combination thereof.

The present specification discloses in part, methods of making a porous material using the porogen compositions disclosed herein. The porogens disclosed herein can be used in any methods of making a porous material that utilized previously described porogens. Examples of such methods are described in, e.g., Gates, et al., Materials Containing Voids with Void Size Controlled on the Nanometer Scale, U.S. Pat. No. 7,674,521; Hart, et al., Discrete Nano-Textured Structures in Biomolecular Arrays and Method of Use, U.S. Pat. No. 7,651,872; Xu and Grenz, Methods and Devices Using a Shrinkable Support for Porous Monolithic Materials, U.S. Pat. No. 7,651,762; van den Hoek, et al., VLSI Fabrication Processes for Introducing Pores into Dielectric Materials, U.S. Pat. No. 7,629,224; Murphy, et al., Tissue Engineering Scaffolds, U.S. Pat. No. 7,575,759; Swetlin, et al., Polyester Compositions, Methods of Manufacturing Said Compositions, and Articles Made Therefrom, U.S. Pat. No. 7,557,167; Goodner, et al., Formation of Interconnect Structures by Removing Sacrificial Material with Supercritical Carbon Dioxide, U.S. Pat. No. 7,466,025; Xu, Ultraporous Sol Gel Monoliths, U.S. Pat. No. 7,439,272; Todd, Apparatus, Precursors and Deposition Methods for Silicon-Containing Materials, U.S. Pat. No. 7,425,350; Flodin and Aurell, Method for Preparing an Open Porous Polymer Material and an Open Porous Polymer Material, U.S. Pat. No. 7,425,288; Watkins and Pai, Mesoporous Materials and Methods, U.S. Pat. No. 7,419,772; Connor, et al., Porous Composition of Matter, and Method of Making Same, U.S. Pat. No. 7,368,483; Lukas, et al., Porous Low Dielectric Constant Compositions and Methods for Making and Using Same, U.S. Pat. No. 7,332,445; Wu, et al., Methods for Producing Low Stress Porous Low-K Dielectric Materials Using Precursors with Organic Functional Groups, U.S. Pat. No. 7,241,704; Yuan and Ding, Functionalized Porous Poly (Aryl Ether Ketone) Materials and Their Use, U.S. Pat. No. 7,176,273; Gleason, et al., Porous Material Formation by Chemical Vapor Deposition onto Colloidal Crystal Templates, U.S. Pat. No. 7,112,615; Bruza, et al., Composition Containing a Cross-Linkable Matrix Precursor and a Porogen, and Porous Matrix Prepared Therefrom, U.S. Pat. No. 7,109,249; Huang, et al., Nitrogen-Containing Polymers as Porogens in the Preparation of Highly Porous, Low Dielectric Constant Materials, U.S. Pat. No. 7,087,982; Taboas, et al., Controlled Local/Global and Micro/Macro-Porous 3D Plastic, Polymer and Ceramic/Cement Composite Scaffold Fabrication and Applications Thereof, U.S. Pat. No. 7,087, 200; Kloster, et al., Method of Forming a Selectively Converted Inter-Layer Dielectric Using A Porogen Material, U.S. Pat. No. 7,018,918; You, et al., Porous Materials, U.S. Pat. No. 6,998,148; Khanarian, et al., Porous Optical Materials, U.S. Pat. No. 6,967,222; Holmes and Cooper, Manufacturing Porous Cross-Linked Polymer Monoliths, U.S. Pat. No. 6,693,159; Ma, Reverse Fabrication of Porous Materials, U.S. Pat. No. 6,673,285; Kilaas, et al., Combined Liner and Matrix System, U.S. Pat. No. 6,672,385; Chaouk and Meijs, Hydratable Siloxane Comprising Porous Polymers, U.S. Pat. No. 6,663,668; Allen, et al., Porous Materials, U.S. Pat. No. 6,602,804; Hawker, et al., Porous Dielectric Material and Electronic Devices Fabricated Therewith, U.S. Pat. No. 6,541,865; Davankov, et al., Method of Making Biocompatible Polymeric Adsorbing Material for Purification of Physiological Fluids of Organism, U.S. Pat. No. 6,531,523; Shastri, et al., Three-Dimensional Polymer Matrices, U.S. Pat. No. 6,471,993; Yates, Photogenerated Nanoporous Materials, U.S. Pat. No. 6,380,270; Fonnum, Method for the Manufacture of Amino Group Containing Support Matrices, Support Matrices Prepared by the Method, and Use of the Support Matrices, U.S. Pat. No. 6,335,438; Chaouk, et al., Polymers, U.S. Pat. No. 6,225,367; Chaouk, et al., High Water Content Porous Polymer, U.S. Pat. No. 6,160,030; Hawker, et al., Dielectric Compositions and Method for Their Manufacture, U.S. Pat. No. 6,107,357; Li, et al., Polymeric Microbeads and Methods of Preparation, U.S. Pat. No. 6,100,306; Chaouk, et al., Process for Manufacture of A Porous Polymer by Use of A Porogen, U.S. Pat. No. 6,060,530; Li, et al., Polymeric Microbeads, U.S. Pat. No. 5,863,957; Frechet and Svec, Porous Polymeric Material with Gradients, U.S. Pat. No. 5,728,457; Frechet and Svec, Pore-Size Selective Modification of Porous Materials, U.S. Pat. No. 5,633,290; Yen, et al., Ion Exchange Polyethylene Membrane and Process, U.S. Pat. No. 5,531,899; Soria, et al., Membrane for a Filtration, Gas or Liquid Separation or Pervaporation Apparatus and A Manufacturing Method for Such Membrane, U.S. Pat. No. 5,066,398; Axisa, et al., Method of Fabricating A Porous Elastomer, U.S. Patent Pub. No. 2010/0075056; Liljensten and Persoon, Biodegradable Osteochondral Implant, U.S. Patent Pub. No. 2009/0164014; Favis, et al., Porous Nanosheath Networks, Method of Making and Uses Thereof, U.S. Patent Pub. No. 2009/0087641; Hosoya, et al., Porous Polymer and Process For Producing the Same, U.S. Patent Pub. No. 2009/0045119; Andersson, Chitosan Compositions, U.S. Patent Pub. No. 2009/0022770; Xie, Three-Dimensional Hydrophilic Porous Structures for Fuel Cell Plates, U.S. Patent Pub. No. 2008/0292939; Ratner and Marshall, Novel Porous Materials, U.S. Patent Pub. No. 2008/0075752; Ma and Chen, Porous Materials having Multi-Sized Geometries, U.S. Patent Pub. No. 2007/0036844; Ma, Reverse Fabrication of Porous Materials, U.S. Patent Pub. No. 2002/0005600; Liu, et al., Porous Materials, Methods of Making and Uses, and Liu, et al., Porous Materials, Methods of Making and Uses, each of which is incorporated by reference in its entirety.

In one aspect, a method of making a porous material comprises the steps of: a) fusing porogens disclosed herein to form a porogen scaffold comprising fused porogens; b) coating the porogen scaffold with a substance base to form a substance coated porogen scaffold; c) treating the substance coated porogen scaffold to stabilize the substance; and d) removing the porogen scaffold, wherein porogen scaffold removal results in a porous material, the porous material comprising a matrix defining an array of interconnected pores.

In another aspect, a method of making a porous material comprises the steps of: a) coating porogens disclosed herein with a substance base to form a substance coated porogen mixture; b) treating the substance coated porogen mixture to form a porogen scaffold and stabilize the substance; and c) removing the porogen scaffold, wherein porogen scaffold removal results in a porous material, the porous material comprising a matrix defining an array of interconnected pores.

In yet another aspect, a method of making a porous material comprises the steps of: a) packing porogens disclosed herein into a mold; b) fusing the porogens to form a porogen scaffold comprising fused porogens; c) coating the porogen scaffold with a substance base to form a substance coated porogen scaffold; d) treating the substance coated porogen scaffold to stabilize the substance; and e) removing the porogen scaffold, wherein porogen scaffold removal results in a porous material, the porous material comprising a matrix defining an array of interconnected pores.

In still another aspect, a method of making a porous material comprises the steps of: a) coating porogens disclosed herein with a substance base to form a substance coated porogen mixture; b) packing substance coated porogen mixture into a mold; c) treating the substance coated porogen mixture to form a porogen scaffold and stabilize the substance; and d) removing the porogen scaffold, wherein porogen scaffold removal results in a porous material, the porous material comprising a matrix defining an array of interconnected pores.

As used herein, the term "substance base" is synonymous with "uncured substance" and refers to a substance disclosed herein that is in its uncured state. A substance base may be an elastomer base. As used herein, the term "elastomer base" is synonymous with "uncured elastomer" and refers to an elastomer disclosed herein that is in its uncured state. An elastomer base may be a silicon-based elastomer base. As used herein, the term "silicon-based elastomer base" is synonymous with "uncured silicon-based elastomer" and refers to a silicon-based elastomer disclosed herein that is in its uncured state.

The present specification discloses, in part, packing porogens into a mold prior to fusion. Any mold shape may be used for packing the porogens. Porogens can be packed into the mold before coating of an uncured substance base, or can be first coated with a substance base before packing into a mold. If packed before coating, the porogens may be first treated to form a porogen scaffold before the addition of an uncured substance base. Alternatively, the porogens may be packed into the mold first, an uncured substance may then be added to the mold, and then the substance coated porogen mixture treated to form a porogen scaffold and cured substance. The substance coated porogen mixture may first have to be devolitalized before packing into a mold and/or before treating. The porogens and/or substance coated porogens may be packed into a mold using ultrasonic agitation, mechanical agitation, casting, or any other suitable method for obtaining a closely packed array of porogens.

A mold shape can be a shell that outlines the contours an implantable device, such as, e.g., a shell for a breast implant, a shell for a muscle implant, a tissue expander, a pacemaker, a defibrillator, any other tissue implant used for prosthetic, reconstructive, or aesthetic purposes, or any other implantable medical device. A mold shape can also be a three-dimensional form of a component or part whose shape the porous material is to represent. For instance, a mold shape can be shaped into a body part or portion of a body part, such as, e.g., a breast or portion thereof, an facial feature or portion thereof like a check, an ear, a nose or portion thereof, a muscle or portion thereof, a cartilage or portion thereof, a bone or portion thereof, a finger, a toe, or portion thereof, dura matter or portion thereof, any other soft tissue part or portion thereof, or any other implant used for prosthetic, reconstructive, or aesthetic purposes.

A mold shape can also be one that forms a sheet. Such sheets can be made in a wide variety or proportions based on the needed application. A sheet can be of any dimension or geometrical shape, such as, e.g., spherical, ellipsoidal, polyhedronal, triangular, pyramidal, quadrilateral like squares, rectangles, parallelograms, trapezoids, rhombus and kites, and other types of polygonal shapes. Sheets can be made in a size slightly bigger that an implantable device so that there is sufficient material to cover the device and allow for trimming of the excess. As another example, the sheets can be produced as a continuous roll that allows a person skilled in the art to take only the desired amount for an application, such as, e.g., creating strips having a textured surface for control of scar formation.

The thickness of a sheet may be of any thickness suitable for its application. For example, a sheet may be from about 0.1 mm to about 1 mm, about 0.25 mm to about 1.5 mm, about 0.25 mm to about 2.5 mm, or about 0.5 mm to about 5 mm in thickness. In aspects of this embodiment, a sheet comprises a thickness of, e.g., about 100 μm, about 200 μm, about 300 μm, about 400 μm, about 500 μm, about 600 μm, about 700 μm, about 800 μm, about 900 μm, about 1 mm, about 2 mm, about 3 mm, about 4 mm, about 5 mm, about 6 mm, about 7 mm, about 8 mm, about 9 mm, or about 10 mm. In other aspects of this embodiment, a sheet comprises a thickness of, e.g., at least 100 μm, at least 200 μm, at least 300 μm, at least 400 μm, at least 500 μm, at least 600 μm, at least 700 μm, at least 800 μm, at least 900 μm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a sheet comprises a thickness of, e.g., at most 100 μm, at most 200 μm, at most 300 μm, at most 400 μm, at most 500 μm, at most 600 μm, at most 700 μm, at most 800 μm, at most 900 μm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a sheet comprises a thickness of, e.g., about 100 μm to about 500 μm, about 100 μm to about 1 mm, about 100 μm to about 5 mm, about 300 μm to about 1 mm, about 300 μm to about 2 mm, about 300 μm to about 3 mm, about 300 μm to about 4 mm, about 300 μm to about 5 mm, about 500 μm to about 1 mm, about 500 μm to about 2 mm, about 500 μm to about 3 mm, about 500 μm to about 4 mm, about 500 μm to about 5 mm, about 800 μm to about 1 mm, about 800 μm to about 2 mm, about 800 μm to about 3 mm, about 800 μm to about 4 mm, about 800 μm to about 5 mm, about 1 mm to about 2 mm, about 1 mm to about 3 mm, about 1 mm to about 4 mm, about 1 mm to about 5 mm, or about 1.5 mm to about 3.5 mm.

In an embodiment, a substance coated porogen mixture is packed into a mold. In an aspect of this embodiment, a substance coated porogen mixture is packed into a mold in a manner suitable obtaining a closely packed array of porogens. In other aspects of this embodiment, a substance coated porogen mixture is packed into a mold using sonic agitation or mechanical agitation.

In another embodiment, porogens are packed into a mold. In an aspect of this embodiment, porogens are packed into a mold in a manner suitable obtaining a closely packed array of porogens. In other aspects of this embodiment, porogens are packed into a mold using sonic agitation or mechanical agitation.

As used herein, the term "porogen scaffold" refers to a three-dimensional structural framework composed of fused porogens that serves as the negative replica of a matrix defining an interconnected array or pores. The porogen compositions disclosed herein comprise a shell material and a core material.

The present specification discloses, in part, coating porogens with a substance base to form a substance coated porogen mixture. Coating the porogens with a substance base can be accomplished by any suitable means, including, without limitation, mechanical application such as, e.g., dipping, spraying, knifing, curtaining, brushing, or vapor deposition, thermal application, adhering application, chemical bonding, self-assembling, molecular entrapment, and/or any combination thereof. The substance is applied to the porogens in such a manner as to coat the porogens with the desired thickness of substance. Removal of excess substance base can be accomplished by any suitable means, including, without limitation, gravity-based filtering or sieving, vacuum-based filtering or sieving, blowing, and/or any combination thereof.

Any substance base can be used to coat the porogens with the proviso that the substance base is a suitable material to form a porous material. A substance base can be any organic or inorganic material, composites thereof, and/or combinations thereof. Suitable substance bases include, without limitation, natural and synthetic ceramics and/or its derivatives, natural and synthetic polysaccharides and its derivatives, natural and synthetic metals and its derivatives, natural and synthetic polymers and its derivatives, and/or natural and synthetic elastomers and its derivatives, composites thereof, and/or combinations thereof.

A natural or synthetic elastomer or elastic polymer refers to an amorphous polymer that exists above its glass transition temperature at ambient temperatures, thereby conferring the property of viscoelasticity so that considerable segmental motion is possible, and includes, without limitation, carbon-based elastomers, silicon-based elastomers, thermoset elastomers, and thermoplastic elastomers. As used herein, the term "ambient temperature" refers to a temperature of about 18° C. to about 22° C. Elastomers, ether naturally occurring or synthetically made, comprise monomers usually made of carbon, hydrogen, oxygen, and/or silicon which are linked together to form long polymer chains. Elastomers are typically covalently cross-linked to one another, although non-covalently cross-linked elastomers are known. Elastomers may be homopolymers or copolymers, degradable, substantially non-degradable, or non-degradable. Copolymers may be random copolymers, blocked copolymers, graft copolymers, and/or mixtures thereof. Unlike other polymers classes, elastomers can be stretched many times its original length without breaking by reconfiguring themselves to distribute an applied stress, and the cross-linkages ensure that the elastomers will return to their original configuration when the stress is removed. Elastomers can be a non-medical grade elastomer or a medical grade elastomer. Medical grade elastomers are typically divided into three categories: non-implantable, short term implantable and long-term implantable. Exemplary substantially non-degradable and/or non-degradable, biocompatible, elastomers include, without limitation, bromo isobutylene isoprene (BIIR), polybutadiene (BR), chloro isobutylene isoprene (CIIR), polychloroprene (CR), chlorosulphonated polyethylene (CSM), ethylene propylene (EP), ethylene propylene diene monomer (EPDM), fluorinated hydrocarbon (FKM), fluoro silicone (FVQM), hydrogenated nitrile butadiene (HNBR), polyisoprene (IR), isobutylene isoprene butyl (IIR), methyl vinyl silicone (MVQ), acrylonitrile butadiene (NBR), polyurethane (PU), styrene butadiene (SBR), styrene ethylene/butylene styrene (SEBS), polydimethylsiloxane (PDMS), polysiloxane (SI), and acrylonitrile butadiene carboxy monomer (XNBR).

Thus, in an embodiment, porogens are coated with a substance base to a thickness sufficient to allow formation of a porous material comprising a matrix defining an interconnected array or pores. In aspects of this embodiment, porogens are coated with a substance to a thickness of, e.g., about 1 μm, about 2 μm, about 3 μm, about 4 μm, about 5 μm, about 6 μm, about 7 μm, about 8 μm, about 9 μm, about 10 μm, about 20 μm, about 30 μm, about 40 μm, about 50 μm, about 60 μm, about 70 μm, about 80 μm, about 90 μm, or about 100 μm. In other aspects of this embodiment, porogens are coated with a substance base to a thickness of, e.g., at least 1 μm, at least 2 μm, at least 3 μm, at least 4 μm, at least 5 μm, at least 6 μm, at least 7 μm, at least 8 μm, at least 9 µm, at least 10 µm, at least 20 µm, at least 30 µm, at least 40 µm, at least 50 µm, at least 60 µm, at least 70 µm, at least 80 µm, at least 90 µm, or at least 100 µm. In yet other aspects of this embodiment, porogens are coated with a substance base to a thickness of, e.g., at most 1 µm, at most 2 µm, at most 3 µm, at most 4 µm, at most 5 µm, at most 6 µm, at most 7 µm, at most 8 µm, at most 9 µm, at most 10 µm, at most 20 µm, at most 30 µm, at most 40 µm, at most 50 µm, at most 60 µm, at most 70 µm, at most 80 µm, at most 90 µm, or at most 100 µm. In still other aspects of this embodiment, porogens are coated with a substance base to a thickness of, e.g., about 1 µm to about 5 µm, about 1 µm to about 10 µm, about 5 µm to about 10 µm, about 5 µm to about 25 µm, about 5 µm to about 50 µm, about 10 µm to about 50 µm, about 10 µm to about 75 µm, about 10 µm to about 100 µm, about 25 µm to about 100 µm, or about 50 µm to about 100 µm.

The present specification discloses, in part, devolitalizing a substance coated porogens. As used herein, the term "devolitalizing" or "devolitalization" refers to a process that removes volatile components from a substance base or a substance coated porogens. Devolitalization of a substance base and/or a substance coated porogens can be accomplished by any suitable means that substantially all the volatile components removed from the substance coated porogens. Non-limiting examples of devolitalizing procedures include evaporation, freeze-drying, sublimation, extraction, and/or any combination thereof.

In an embodiment, a substance base and/or substance coated porogen is devolatilized at a single temperature for a time sufficient to allow the evaporation of substantially all volatile components from the elastomer coated porogens. In aspects of this embodiment a substance base and/or substance coated porogen is devolatilized at ambient temperature for e.g., about 1 minute to about 5 minutes, about 4 minutes to about 5 minutes, about 4.5 minutes to about 5.5 minutes, about 4 minutes to about 6 minutes, about 3 minutes to about 8 minutes, about 5 minutes to about 10 minutes, about 10 minutes to about 15 minutes, about 10 minutes to about 20 minutes, about 15 minutes to about 20 minutes, about 15 minutes to about 25 minutes, or about 19 minutes to about 21 minutes. In other aspects of this embodiment, a substance base and/or substance coated porogen is devolatilized at ambient temperature for e.g., about 20 minutes to about 45 minutes, about 25 minutes to about 35 minutes, about 30 minutes to about 45 minutes, about 30 minutes to about 60 minutes, about 25 minutes to about 35 minutes, about 29 minutes to about 31 minutes, or about 40 minutes to about 50 minutes. In another aspect of this embodiment, a substance base and/or substance coated porogen is devolatilized at ambient temperature for 45 minutes or more. In another aspect of this embodiment, a substance base and/or substance coated porogen is devolatilized at ambient temperature for about 45 minutes to about 75 minutes. In yet another aspect of this embodiment, a substance base and/or substance coated porogen is devolatilized at ambient temperature for about 90 minutes to about 150 minutes.

In another aspect of this embodiment, a substance base and/or substance coated porogen is devolatilized at about 18° C. to about 22° C. for about 1 minute to about 5 minutes. In yet another aspect of this embodiment, a substance base and/or substance coated porogen is devolatilized at about 18° C. to about 22° C. for about 4 minutes to about 6 minutes. In still another aspect of this embodiment, a substance base and/or substance coated porogen is devolatilized at about 18° C. to about 22° C. for about 4 minutes to about 5 minutes. In another aspect of this embodiment, a substance base and/or substance coated porogen is devolatilized at about 18° C. to about 22° C. for about 4.5 minutes to about 5.5 minutes. In another aspect of this embodiment, a substance base and/or substance coated porogen is devolatilized at about 18° C. to about 22° C. for about 45 minutes to about 75 minutes. In yet another aspect of this embodiment, a substance base and/or substance coated porogen is devolatilized at about 18° C. to about 22° C. for about 15 minutes to about 25 minutes. In still another aspect of this embodiment, a substance base and/or substance coated porogen is devolatilized at about 18° C. to about 22° C. for about 18 minutes to about 22 minutes. In another aspect of this embodiment, a substance base and/or substance coated porogen is devolatilized at about 18° C. to about 22° C. for about 21 minutes to about 23 minutes. In yet another aspect of this embodiment, a substance base and/or substance coated porogen is devolatilized at about 18° C. to about 22° C. for about 25 minutes to about 35 minutes. In still another aspect of this embodiment, a substance base and/or substance coated porogen is devolatilized at about 18° C. to about 22° C. for about 29 minutes to about 31 minutes. In still another aspect of this embodiment, a substance base and/or substance coated porogen is devolatilized at about 18° C. to about 22° C. for about 90 minutes to about 150 minutes.

In another aspect of this embodiment, a substance base and/or substance coated porogen is devolatilized at about 23° C. to about 27° C. for about 1 minute to about 5 minutes. In yet another aspect of this embodiment, a substance base and/or substance coated porogen is devolatilized at about 23° C. to about 27° C. for about 4 minutes to about 6 minutes. In still another aspect of this embodiment, a substance base and/or substance coated porogen is devolatilized at about 23° C. to about 27° C. for about 4 minutes to about 5 minutes. In another aspect of this embodiment, a substance base and/or substance coated porogen is devolatilized at about 23° C. to about 27° C. for about 4.5 minutes to about 5.5 minutes. In another aspect of this embodiment, a substance base and/or substance coated porogen is devolatilized at about 23° C. to about 27° C. for about 45 minutes to about 75 minutes. In yet another aspect of this embodiment, a substance base and/or substance coated porogen is devolatilized at about 23° C. to about 27° C. for about 15 minutes to about 25 minutes. In still another aspect of this embodiment, a substance base and/or substance coated porogen is devolatilized at about 23° C. to about 27° C. for about 18 minutes to about 22 minutes. In another aspect of this embodiment, a substance base and/or substance coated porogen is devolatilized at about 23° C. to about 27° C. for about 21 minutes to about 23 minutes. In yet another aspect of this embodiment, a substance base and/or substance coated porogen is devolatilized at about 23° C. to about 27° C. for about 25 minutes to about 35 minutes. In still another aspect of this embodiment, a substance base and/or substance coated porogen is devolatilized at about 23° C. to about 27° C. for about 29 minutes to about 31 minutes. In still another aspect of this embodiment, a substance base and/or substance coated porogen is devolatilized at about 23° C. to about 27° C. for about 90 minutes to about 150 minutes.

The present specification discloses, in part, treating a substance coated porogen mixture to allow fusing of the porogens to form a porogen scaffold and stabilization of the substance. As used herein, the term "treating" refers to a process that 1) fuses the porogens to form a porogen scaffold useful to make a porous material comprising a matrix of interconnected array of pore and/or 2) stabilizes the substance. Non-limiting examples of treating include thermal treating like heating or freezing, chemical treating, catalyst treating, radiation treating, and physical treating. Treating of a substance coated porogen scaffold can be done under any condition for any length of time with the proviso that the treating fuses the porogens to form a porogen scaffold useful to make a porous material comprising a matrix of interconnected array of pore and stabilizes the substance and cures a substance base to form a substance matrix sufficient to allow tissue growth within its array of interconnected of pores as disclosed herein.

Thermal treating a substance coated porogen mixture can be at any temperature or temperatures for any length of time or times with the proviso that the thermal treatment fuses the porogens to form a porogen scaffold and stabilizes the substance base to form a substance matrix as disclosed herein. A non-limiting example of temperatures useful in a thermal treatment are temperatures higher than the glass transition temperature or melting temperature of the porogens, such as between about 5° C. to about 50° C. higher than the glass transition temperature or melting temperature of the porogens. Any temperature can be used in a thermal treatment with the proviso that the temperature is sufficient to cause fusion of the porogens. As a non-limiting example, the thermal treatment can be from about 30° C. to about 250° C. Increasing the duration of the thermal treatment at a given temperature increases the connection size; increases the sintering temperature, and increases the growth rate of the connections. Any time can be used in a thermal treatment with the proviso that the time is sufficient to cause fusion of the porogens and cures the substance. Suitable times are generally from about 0.5 hours to about 48 hours.

Thus, in an embodiment, a substance coated porogen scaffold is treated by thermal treatment, chemical treatment, catalyst treatment, radiation treatment, or physical treatment where the treatment is sufficient to stabilize a substance. In another embodiment, a substance coated porogen scaffold is treated at a single time, where the treating time is sufficient to stabilize a substance.

In another embodiment, substance coated porogens are thermal treated at a single temperature for a single time, where the treating temperature and time is sufficient to fuse the porogens to form a porogen scaffold and cure the substance to form a substance matrix sufficient to allow tissue growth within its array of interconnected of pores.

In other aspects of this embodiment, the thermal treatment comprises heating a substance coated porogens for a time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected of pores. In yet other aspects of this embodiment, the thermal treatment comprises heating a substance coated porogens for a time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected of pores. In still other aspects of this embodiment, the thermal treatment comprises heating a substance coated porogens for a time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected of pores. In further aspects of this embodiment, the thermal treatment comprises heating a substance coated porogens for a time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected of pores.

In another aspect of this embodiment, the thermal treatment comprises heating a substance coated porogen scaffold is treated at about 30° C. to about 140° C. for about 10 minutes to about 360 minutes, where the treating temperature and time is sufficient to fuse the porogens to form a porogen scaffold and cure the substance base to form a substance matrix sufficient to allow tissue growth within its array of interconnected of pores. In another aspect of this embodiment, the thermal treatment comprises heating a substance coated porogen scaffold is treated at about 110° C. to about 140° C. for about 65 minutes to about 105 minutes, where the treating temperature and time is sufficient to fuse the porogens to form a porogen scaffold and cure the substance base to form a substance matrix sufficient to allow tissue growth within its array of interconnected of pores. In another aspect of this embodiment, the thermal treatment comprises heating a substance coated porogen scaffold is treated at about 115° C. to about 135° C. for about 75 minutes to about 95 minutes, where the treating temperature and time is sufficient to fuse the porogens to form a porogen scaffold and cure the substance base to form a substance matrix sufficient to allow tissue growth within its array of interconnected of pores. In another aspect of this embodiment, the thermal treatment comprises heating a substance coated porogen scaffold is treated at about 120° C. to about 130° C. for about 80 minutes to about 90 minutes, where the treating temperature and time is sufficient to fuse the porogens to form a porogen scaffold and cure the substance base to form a substance matrix sufficient to allow tissue growth within its array of interconnected of pores. In another aspect of this embodiment, the thermal treatment comprises heating a substance coated porogen scaffold is treated at about 126° C. for about 85 minutes, where the treating temperature and time is sufficient to fuse the porogens to form a porogen scaffold and cure the substance base to form a substance matrix sufficient to allow tissue growth within its array of interconnected of pores. In another aspect of this embodiment, the thermal treatment comprises heating a substance coated porogen scaffold is treated at about 126° C. for about 75 minutes, where the treating temperature and time is sufficient to fuse the porogens to form a porogen scaffold and cure the substance base to form a substance matrix sufficient to allow tissue growth within its array of interconnected of pores.

In yet another embodiment, a substance-coated porogens are thermal treated at a plurality of temperatures for a plurality of times, where the treating temperatures and times are sufficient to fuse the porogens to form a porogen scaffold and cure the substance to form a substance matrix sufficient to allow tissue growth within its array of interconnected of pores. In an aspect of this embodiment, substance coated porogens are treated at a first temperature for a first time, and then a second temperature for a second time, where the treating temperatures and times are sufficient to fuse the porogens to form a porogen scaffold and cure the substance to form a substance matrix sufficient to allow tissue growth within its array of interconnected of pores, and where the first and second temperatures are different.

In aspects of this embodiment, thermal treatment comprises heating the substance coated porogens at a first temperature for a first time, and then heating the porogens at a second temperature for a second time, where the treating temperatures and times are sufficient to fuse the porogens to form a porogen scaffold and cure the substance to form a substance matrix sufficient to allow tissue growth within its array of interconnected of pores, and where the first and second temperatures are different, and where the first and second temperatures are different. In other aspects of this embodiment, the thermal treatment comprises heating a substance coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the substance coated porogens, then heating for a second time the porogens at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first and second temperatures are different. In yet other aspects of this embodiment, the thermal treatment comprises heating a substance coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating a substance coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first and second temperatures are different. In still other aspects of this embodiment, the thermal treatment comprises heating a substance coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating a substance coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first and second temperatures are different.

In further aspects of this embodiment, the thermal treatment comprises heating a substance coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating a substance coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first and second temperatures are different.

In other aspects of this embodiment, thermal treatment comprises heating the substance coated porogens at a first temperature for a first time, heating the porogens at a second temperature for a second time, and then heating the porogens at a third temperature at a third time, where the treating temperatures and times are sufficient to fuse the porogens to form a porogen scaffold and cure the substance to form a substance matrix sufficient to allow tissue growth within its array of interconnected of pores, and where the first temperature is different from the second temperature and the second temperature is different form the third temperature.

In other aspects of this embodiment, the thermal treatment comprises heating a substance coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating a substance coated porogens for a second time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating a substance coated porogens for a third time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first temperature is different from the second temperature and the second temperature is different form the third temperature. In yet other aspects of this embodiment, the thermal treatment comprises heating a substance coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating a substance coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating a substance coated porogens for a third time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first temperature is different from the second temperature and the second temperature is different form the third temperature. In still other aspects of this embodiment, the thermal treatment comprises heating a substance coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating a substance coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating a substance coated porogens for a third time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first temperature is different from the second temperature and the second temperature is different from the third temperature.

In further aspects of this embodiment, the thermal treatment comprises heating a substance coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating a substance coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating a substance coated porogens for a third time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected of pores, and where the first temperature is different from the second temperature and the second temperature is different from the third temperature.

In still other aspect of this embodiment, substance coated porogens are treated at about 60° C. to about 75° C. for about 15 minutes to about 45 minutes, and then at about 120° C. to about 130° C. for about 60 minutes to about 90 minutes, where the treating temperatures and times is sufficient to fuse the porogens to form a porogen scaffold and cure the substance to form a substance matrix sufficient to allow tissue growth within its array of interconnected of pores. In a further aspect of this embodiment, substance coated porogen mixture is treated at about 60° C. to about 75° C. for about 15 minutes to about 45 minutes, then at about 135° C. to about 150° C. for about 90 minutes to about 150 minutes, and then at about 150° C. to about 165° C. for about 15 minutes to about 45 minutes.

The present specification discloses, in part, to form a porogen scaffold. As used herein, the term "porogen scaffold" refers to a three-dimensional structural framework composed of fused porogens that serves as the negative replica of the elastomer matrix defining an interconnected array or pores as disclosed herein.

The porogen scaffold is formed in such a manner that substantially all the fused porogens in the porogen scaffold have a similar diameter. As used herein, the term "substantially", when used to describe fused porogen, refers to at least 90% of the porogen comprising the porogen scaffold are fused, such as, e.g., at least 95% of the porogens are fused or at least 97% of the porogen are fused. As used herein, the term "similar diameter", when used to describe fused porogen, refers to a difference in the diameters of the two fused porogen that is less than about 20% of the larger diameter. As used herein, the term "diameter", when used to describe fused porogen, refers to the longest line segment that can be drawn that connects two points within the fused porogen, regardless of whether the line passes outside the boundary of the fused porogen. Any fused porogen diameter is useful with the proviso that the fused porogen diameter is sufficient to allow formation of a porogen scaffold useful in making a substance matrix as disclosed herein.

The porogen scaffold is formed in such a manner that the diameter of the connections between each fused porogen is sufficient to allow formation of a porogen scaffold useful in making a substance matrix as disclosed herein. As used herein, the term "diameter", when describing the connection between fused porogens, refers to the diameter of the cross-section of the connection between two fused porogens in the plane normal to the line connecting the centroids of the two fused porogens, where the plane is chosen so that the area of the cross-section of the connection is at its minimum value. As used herein, the term "diameter of a cross-section of a connection" refers to the average length of a straight line segment that passes through the center, or centroid (in the case of a connection having a cross-section that lacks a center), of the cross-section of a connection and terminates at the periphery of the cross-section. As used herein, the term "substantially", when used to describe the connections between fused porogens refers to at least 90% of the fused porogens comprising the porogen scaffold make connections between each other, such as, e.g., at least 95% of the fused porogens make connections between each other or at least 97% of the fused porogens make connections between each other.

In an embodiment, a porogen scaffold comprises fused porogens where substantially all the fused porogens have a similar diameter. In aspects of this embodiment, at least 90% of all the fused porogens have a similar diameter, at least 95% of all the fused porogens have a similar diameter, or at least 97% of all the fused porogens have a similar diameter. In another aspect of this embodiment, difference in the diameters of two fused porogens is, e.g., less than about 20% of the larger diameter, less than about 15% of the larger diameter, less than about 10% of the larger diameter, or less than about 5% of the larger diameter.

In another embodiment, a porogen scaffold comprises fused porogens have a mean diameter sufficient to allow tissue growth into the array of interconnected porogens. In aspects of this embodiment, a porogen scaffold comprises fused porogens comprising mean fused porogen diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen scaffold comprises fused porogens comprising mean fused porogen diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen scaffold comprises fused porogens comprising mean fused porogen diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porogen scaffold comprises fused porogens comprising mean fused porogen diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen scaffold comprises fused porogens comprising mean fused porogen diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porogen scaffold comprises fused porogens comprising mean fused porogen diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen scaffold comprises fused porogens comprising mean fused porogen diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porogen scaffold comprises fused porogens connected to a plurality of other porogens. In aspects of this embodiment, a porogen scaffold comprises a mean fused porogen connectivity, e.g., about two other fused porogens, about three other fused porogens, about four other fused porogens, about five other fused porogens, about six other fused porogens, about seven other fused porogens, about eight other fused porogens, about nine other fused porogens, about ten other fused porogens, about 11 other fused porogens, or about 12 other fused porogens. In other aspects of this embodiment, a porogen scaffold comprises a mean fused porogen connectivity, e.g., at least two other fused porogens, at least three other fused porogens, at least four other fused porogens, at least five other fused porogens, at least six other fused porogens, at least seven other fused porogens, at least eight other fused porogens, at least nine other fused porogens, at least ten other fused porogens, at least 11 other fused porogens, or at least 12 other fused porogens. In yet other aspects of this embodiment, a porogen scaffold comprises a mean fused porogen connectivity, e.g., at most two other fused porogens, at most three other fused porogens, at most four other fused porogens, at most five other fused porogens, at most six other fused porogens, at most seven other fused porogens, at most eight other fused porogens, at most nine other fused porogens, at most ten other fused porogens, at most 11 other fused porogens, or at most 12 other fused porogens.

In still other aspects of this embodiment, a porogen scaffold comprises fused porogens connected to, e.g., about two other fused porogens to about 12 other fused porogens, about two other fused porogens to about 11 other fused porogens, about two other fused porogens to about ten other fused porogens, about two other fused porogens to about nine other fused porogens, about two other fused porogens to about eight other fused porogens, about two other fused porogens to about seven other fused porogens, about two other fused porogens to about six other fused porogens, about two other fused porogens to about five other fused porogens, about three other fused porogens to about 12 other fused porogens, about three other fused porogens to about 11 other fused porogens, about three other fused porogens to about ten other fused porogens, about three other fused porogens to about nine other fused porogens, about three other fused porogens to about eight other fused porogens, about three other fused porogens to about seven other fused porogens, about three other fused porogens to about six other fused porogens, about three other fused porogens to about five other fused porogens, about four other fused porogens to about 12 other fused porogens, about four other fused porogens to about 11 other fused porogens, about four other fused porogens to about ten other fused porogens, about four other fused porogens to about nine other fused porogens, about four other fused porogens to about eight other fused porogens, about four other fused porogens to about seven other fused porogens, about four other fused porogens to about six other fused porogens, about four other fused porogens to about five other fused porogens, about five other fused porogens to about 12 other fused porogens, about five other fused porogens to about 11 other fused porogens, about five other fused porogens to about ten other fused porogens, about five other fused porogens to about nine other fused porogens, about five other fused porogens to about eight other fused porogens, about five other fused porogens to about seven other fused porogens, or about five other fused porogens to about six other fused porogens.

In another embodiment, a porogen scaffold comprises fused porogens where the diameter of the connections between the fused porogens is sufficient to allow formation of a porogen scaffold useful in making a substance matrix that allows tissue growth within its array of interconnected of pores. In aspects of this embodiment, the porogen scaffold comprises fused porogens where the diameter of the connections between the fused porogens is, e.g., about 10% the mean fused porogen diameter, about 20% the mean fused porogen diameter, about 30% the mean fused porogen diameter, about 40% the mean fused porogen diameter, about 50% the mean fused porogen diameter, about 60% the mean fused porogen diameter, about 70% the mean fused porogen diameter, about 80% the mean fused porogen diameter, or about 90% the mean fused porogen diameter. In other aspects of this embodiment, the porogen scaffold comprises fused porogens where the diameter of the connections between the fused porogens is, e.g., at least 10% the mean fused porogen diameter, at least 20% the mean fused porogen diameter, at least 30% the mean fused porogen diameter, at least 40% the mean fused porogen diameter, at least 50% the mean fused porogen diameter, at least 60% the mean fused porogen diameter, at least 70% the mean fused porogen diameter, at least 80% the mean fused porogen diameter, or at least 90% the mean fused porogen diameter. In yet other aspects of this embodiment, the porogen scaffold comprises fused porogens where the diameter of the connections between the fused porogens is, e.g., at most 10% the mean fused porogen diameter, at most 20% the mean fused porogen diameter, at most 30% the mean fused porogen diameter, at most 40% the mean fused porogen diameter, at most 50% the mean fused porogen diameter, at most 60% the mean fused porogen diameter, at most 70% the mean fused porogen diameter, at most 80% the mean fused porogen diameter, or at most 90% the mean fused porogen diameter.

In still other aspects of this embodiment, a porogen scaffold comprises fused porogens where the diameter of the connections between the fused porogens is, e.g., about 10% to about 90% the mean fused porogen diameter, about 15% to about 90% the mean fused porogen diameter, about 20% to about 90% the mean fused porogen diameter, about 25% to about 90% the mean fused porogen diameter, about 30% to about 90% the mean fused porogen diameter, about 35% to about 90% the mean fused porogen diameter, about 40% to about 90% the mean fused porogen diameter, about 10% to about 80% the mean fused porogen diameter, about 15% to about 80% the mean fused porogen diameter, about 20% to about 80% the mean fused porogen diameter, about 25% to about 80% the mean fused porogen diameter, about 30% to about 80% the mean fused porogen diameter, about 35% to about 80% the mean fused porogen diameter, about 40% to about 80% the mean fused porogen diameter, about 10% to about 70% the mean fused porogen diameter, about 15% to about 70% the mean fused porogen diameter, about 20% to about 70% the mean fused porogen diameter, about 25% to about 70% the mean fused porogen diameter, about 30% to about 70% the mean fused porogen diameter, about 35% to about 70% the mean fused porogen diameter, about 40% to about 70% the mean fused porogen diameter, about 10% to about 60% the mean fused porogen diameter, about 15% to about 60% the mean fused porogen diameter, about 20% to about 60% the mean fused porogen diameter, about 25% to about 60% the mean fused porogen diameter, about 30% to about 60% the mean fused porogen diameter, about 35% to about 60% the mean fused porogen diameter, about 40% to about 60% the mean fused porogen diameter, about 10% to about 50% the mean fused porogen diameter, about 15% to about 50% the mean fused porogen diameter, about 20% to about 50% the mean fused porogen diameter, about 25% to about 50% the mean fused porogen diameter, about 30% to about 50% the mean fused porogen diameter, about 10% to about 40% the mean fused porogen diameter, about 15% to about 40% the mean fused porogen diameter, about 20% to about 40% the mean fused porogen diameter, about 25% to about 40% the mean fused porogen diameter, or about 30% to about 40% the mean fused porogen diameter.

The present specification discloses, in part, stabilizing a substance. As used herein, the term "stabilizing" refers to a process that exposes the substance base to a element which activates a phase change in the substance base to a more stable state, such as, e.g., by physically or chemically cross-linked components of the substance to one another. Such a stabilization forms, e.g., a substance matrix. Non-limiting examples of stabilizing include curing, such as, e.g., thermal curing, chemical curing, catalyst curing, radiation curing, and physical curing. Stabilizing of a substance coated porogen scaffold can be done under any condition for any length of time with the proviso that the conditions used stabilizes the substance.

The present specification discloses, in part, removing a porogen scaffold from a treated substance. Removal of the porogen scaffold can be accomplished by any suitable means, with the proviso that removal results in a porous material comprising a matrix defining an array of interconnected pores. Non-limiting examples of porogen removal include solvent extraction, thermal decomposition extraction, degradation extraction, mechanical extraction, and/or any combination thereof. As such, it is beneficial to use shell and core materials that are removable using an extraction method, but such method leaves the porous material intact. In extraction methods requiring exposure to another solution, such as, e.g., solvent extraction, the extraction can incorporate a plurality of solution changes over time to facilitate removal of the porogen scaffold. Non-limiting examples of solvents useful for solvent extraction include water, methylene chloride, acetic acid, formic acid, pyridine, tetrahydrofuran, dimethylsulfoxide, dioxane, benzene, and/or mixtures thereof. A mixed solvent can be in a ratio of higher than about 1:1, first solvent to second solvent or lower than about 1:1, first solvent to second solvent.

In an embodiment, a porogen scaffold is removed by extraction, where the extraction removes substantially all the porogen scaffold leaving a porous material comprising a matrix defining an array of interconnected pores. In aspects of this embodiment, a porogen scaffold is removed by extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold. In an aspect, a porogen scaffold is removed by a solvent extraction, a thermal extraction, a degradation extraction, a mechanical extraction, and/or any combination thereof.

In another embodiment, a porogen scaffold is removed by solvent extraction, where the extraction removes substantially all the porogen scaffold leaving a porous material comprising a matrix defining an array of interconnected pores. In aspects of this embodiment, a porogen scaffold is removed by solvent extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by solvent extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by solvent extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In yet another embodiment, a porogen scaffold is removed by thermal decomposition extraction, where the extraction removes substantially all the porogen scaffold leaving a porous material comprising a matrix defining an array of interconnected pores. In aspects of this embodiment, a porogen scaffold is removed by thermal decomposition extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by thermal decomposition extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by thermal decomposition extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by degradation extraction, where the extraction removes substantially all the porogen scaffold leaving a porous material comprising a matrix defining an array of interconnected pores. In aspects of this embodiment, a porogen scaffold is removed by degradation extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by degradation extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by degradation extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by mechanical extraction, where the extraction removes substantially all the porogen scaffold leaving a porous material comprising a matrix defining an array of interconnected pores. In aspects of this embodiment, a porogen scaffold is removed by mechanical extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by mechanical extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by mechanical extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In another embodiment, a porogen scaffold is removed by soaking in water. Removal of a porogen scaffold by soaking in water can be accomplished by a single cycle of soaking or a plurality of soaking cycles. One or more rinsing cycle using water may be performed after one, one or more, or all soaking cycles. In addition, scrubbing of the cured substance to remove the porogen scaffold is typically not necessary. In an aspect of this embodiment, removing a porogen scaffold from a cured substance may be accomplished by soaking in water for about 5 to about 30 minutes and then rinsing the resulting porous material. In another aspect of this embodiment, removing a porogen scaffold from a cured substance may be accomplished by soaking in water for about 5 to about 30 minutes, rinsing the resulting porous material, soaking in water for about 5 to about 30 minutes, and then rinsing the resulting porous material. In yet another aspect of this embodiment, removing a porogen scaffold from a cured substance may be accomplished by soaking in water for about 5 to about 30 minutes, rinsing the resulting porous material, soaking in water for about 5 to about 30 minutes, rinsing the resulting porous material, soaking in water for about 5 to about 30 minutes, and then rinsing the resulting porous material.

In an aspect of this embodiment, removing a porogen scaffold from a cured substance may be accomplished by soaking in about 30° C. to about 60° C. water for about 5 to about 30 minutes and then rinsing the resulting porous material. In another aspect of this embodiment, removing a porogen scaffold from a cured substance may be accomplished by soaking in about 30° C. to about 60° C. water for about 5 to about 30 minutes, rinsing the resulting porous material, soaking in about 30° C. to about 60° C. water for about 5 to about 30 minutes, and then rinsing the resulting porous material. In yet another aspect of this embodiment, removing a porogen scaffold from a cured substance may be accomplished by soaking in about 30° C. to about 60° C. water for about 5 to about 30 minutes, rinsing the resulting porous material, soaking in about 30° C. to about 60° C. water for about 5 to about 30 minutes, rinsing the resulting porous material, soaking in about 30° C. to about 60° C. water for about 5 to about 30 minutes, and then rinsing the resulting porous material. In other aspects, the rinsing is done in water less than 45° C., less than 40° C., less than 35° C., less than 30° C., less than 25° C., less than 20° C., or less than 15° C. In other aspects, the rinsing is done in water less than 45° C., less than 40° C., less than 35° C., less than 30° C., less than 25° C., less than 20° C., or less than 15° C. for about 1 minute to about 5 minutes, about 3 minute to about 7 minutes, or about 5 minute to about 10 minutes.

In an aspect of this embodiment, removing a porogen scaffold from a cured substance may be accomplished by soaking in about 40° C. to about 50° C. water for about 5 to about 30 minutes and then rinsing the resulting porous material. In another aspect of this embodiment, removing a porogen scaffold from a cured substance may be accomplished by soaking in about 40° C. to about 50° C. water for about 5 to about 30 minutes, rinsing the resulting porous material, soaking in about 40° C. to about 50° C. water for about 5 to about 30 minutes, and then rinsing the resulting porous material. In yet another aspect of this embodiment, removing a porogen scaffold from a cured substance may be accomplished by soaking in about 40° C. to about 50° C. water for about 5 to about 30 minutes, rinsing the resulting porous material, soaking in about 40° C. to about 50° C. water for about 5 to about 30 minutes, rinsing the resulting porous material, soaking in about 40° C. to about 50° C. water for about 5 to about 30 minutes, and then rinsing the resulting porous material. In other aspects, the rinsing is done in water less than 45° C., less than 40° C., less than 35° C., less than 30° C., less than 25° C., less than 20° C., or less than 15° C. In other aspects, the rinsing is done in water less than 45° C., less than 40° C., less than 35° C., less than 30° C., less than 25° C., less than 20° C., or less than 15° C. for about 1 minute to about 5 minutes, about 3 minute to about 7 minutes, or about 5 minute to about 10 minutes.

In an aspect of this embodiment, removing a porogen scaffold from a cured substance may be accomplished by soaking in about 44° C. to about 46° C. water for about 5 to about 30 minutes and then rinsing the resulting porous material. In another aspect of this embodiment, removing a porogen scaffold from a cured substance may be accomplished by soaking in about 44° C. to about 46° C. water for about 5 to about 30 minutes, soaking in about 40° C. to about 50° C. water for about 5 to about 30 minutes, and then rinsing the resulting porous material. In yet another aspect of this embodiment, removing a porogen scaffold from a cured substance may be accomplished by soaking in about 44° C. to about 46° C. water for about 5 to about 30 minutes, rinsing the resulting porous material, soaking in about 44° C. to about 46° C. water for about 5 to about 30 minutes, rinsing the resulting porous material, soaking in about 44° C. to about 46° C. water for about 5 to about 30 minutes, and then rinsing the resulting porous material. In other aspects, the rinsing is done in water less than 45° C., less than 40° C., less than 35° C., less than 30° C., less than 25° C., less than 20° C., or less than 15° C. In other aspects, the rinsing is done in water less than 45° C., less than 40° C., less than 35° C., less than 30° C., less than 25° C., less than 20° C., or less than 15° C. for about 1 minute to about 5 minutes, about 3 minute to about 7 minutes, or about 5 minute to about 10 minutes.

The present specification discloses, in part, a porous material comprising a substance matrix defining an array of interconnected pores. As used herein, the term "matrix" or "substance matrix" is synonymous with "treated substance" and refers to a three-dimensional structural framework composed of a substance in its treated or cured state. The porous materials formed by methods using the porogen compositions disclosed herein have a wide range of medical, commercial and household applications. In the medical field, porous materials have been used as a matrix for tissue engineering/regeneration, cell growth supporting matrices, wound dressings, drug release matrices, membranes for separations and filtration, sterile filters, artificial kidneys, absorbents, hemostatic devices, and the like. In various industrial and household applications, porous materials have been used as insulating materials, packaging materials, impact absorbers, liquid or gas absorbents, membranes, filters and so forth.

Examples of such matrixes and their uses are described in, e.g., Gates, et al., Materials Containing Voids with Void Size Controlled on the Nanometer Scale, U.S. Pat. No. 7,674,521; Hart, et al., Discrete Nano-Textured Structures in Biomolecular Arrays and Method of Use, U.S. Pat. No. 7,651,872; Xu and Grenz, Methods and Devices Using a Shrinkable Support for Porous Monolithic Materials, U.S. Pat. No. 7,651,762; van den Hoek, et al., VLSI Fabrication Processes for Introducing Pores into Dielectric Materials, U.S. Pat. No. 7,629,224; Murphy, et al., Tissue Engineering Scaffolds, U.S. Pat. No. 7,575,759; Swetlin, et al., Polyester Compositions, Methods of Manufacturing Said Compositions, and Articles Made Therefrom, U.S. Pat. No. 7,557,167; Goodner, et al., Formation of Interconnect Structures by Removing Sacrificial Material with Supercritical Carbon Dioxide, U.S. Pat. No. 7,466,025; Xu, Ultraporous Sol Gel Monoliths, U.S. Pat. No. 7,439,272; Todd, Apparatus, Precursors and Deposition Methods for Silicon-Containing Materials, U.S. Pat. No. 7,425,350; Flodin and Aurell, Method for Preparing an Open Porous Polymer Material and an Open Porous Polymer Material, U.S. Pat. No. 7,425,288; Watkins and Pai, Mesoporous Materials and Methods, U.S. Pat. No. 7,419,772; Connor, et al., Porous Composition of Matter, and Method of Making Same, U.S. Pat. No. 7,368,483; Lukas, et al., Porous Low Dielectric Constant Compositions and Methods for Making and Using Same, U.S. Pat. No. 7,332,445; Wu, et al., Methods for Producing Low Stress Porous Low-K Dielectric Materials Using Precursors with Organic Functional Groups, U.S. Pat. No. 7,241,704; Yuan and Ding, Functionalized Porous Poly(Aryl Ether Ketone) Materials and Their Use, U.S. Pat. No. 7,176,273; Gleason, et al., Porous Material Formation by Chemical Vapor Deposition onto Colloidal Crystal Templates, U.S. Pat. No. 7,112,615; Bruza, et al., Composition Containing a Cross-Linkable Matrix Precursor and a Porogen, and Porous Matrix Prepared Therefrom, U.S. Pat. No. 7,109,249; Huang, et al., Nitrogen-Containing Polymers as Porogens in the Preparation of Highly Porous, Low Dielectric Constant Materials, U.S. Pat. No. 7,087,982; Taboas, et al., Controlled Local/Global and Micro/Macro-Porous 3D Plastic, Polymer and Ceramic/Cement Composite Scaffold Fabrication and Applications Thereof, U.S. Pat. No. 7,087,200; Kloster, et al., Method of Forming a Selectively Converted Inter-Layer Dielectric Using A Porogen Material, U.S. Pat. No. 7,018,918; You, et al., Porous Materials, U.S. Pat. No. 6,998,148; Khanarian, et al., Porous Optical Materials, U.S. Pat. No. 6,967,222; Holmes and Cooper, Manufacturing Porous Cross-Linked Polymer Monoliths, U.S. Pat. No. 6,693,159; Ma, Reverse Fabrication of Porous Materials, U.S. Pat. No. 6,673,285; Kilaas, et al., Combined Liner and Matrix System, U.S. Pat. No. 6,672,385; Chaouk and Meijs, Hydratable Siloxane Comprising Porous Polymers, U.S. Pat. No. 6,663,668; Allen, et al., Porous Materials, U.S. Pat. No. 6,602,804; Hawker, et al., Porous Dielectric Material and Electronic Devices Fabricated Therewith, U.S. Pat. No. 6,541,865; Davankov, et al., Method of Making Biocompatible Polymeric Adsorbing Material for Purification of Physiological Fluids of Organism, U.S. Pat. No. 6,531,523; Shastri, et al., Three-Dimensional Polymer Matrices, U.S. Pat. No. 6,471,993; Yates, Photogenerated Nanoporous Materials, U.S. Pat. No. 6,380,270; Fonnum, Method for the Manufacture of Amino Group Containing Support Matrices, Support Matrices Prepared by the Method, and Use of the Support Matrices, U.S. Pat. No. 6,335,438; Chaouk, et al., Polymers, U.S. Pat. No. 6,225,367; Chaouk, et al., High Water Content Porous Polymer, U.S. Pat. No. 6,160,030; Hawker, et al., Dielectric Compositions and Method for Their Manufacture, U.S. Pat. No. 6,107,357; Li, et al., Polymeric Microbeads and Methods of Preparation, U.S. Pat. No. 6,100,306; Chaouk, et al., Process for Manufacture of A Porous Polymer by Use of A Porogen, U.S. Pat. No. 6,060,530; Li, et al., Polymeric Microbeads, U.S. Pat. No. 5,863,957; Frechet and Svec, Porous Polymeric Material with Gradients, U.S. Pat. No. 5,728,457; Frechet and Svec, Pore-Size Selective Modification of Porous Materials, U.S. Pat. No. 5,633,290; Yen, et al., Ion Exchange Polyethylene Membrane and Process, U.S. Pat. No. 5,531,899; Soria, et al., Membrane for a Filtration, Gas or Liquid Separation or Pervaporation Apparatus and A Manufacturing Method for Such Membrane, U.S. Pat. No. 5,066,398; Axisa, et al., Method of Fabricating A Porous Elastomer, U.S. Patent Pub. No. 2010/0075056; Liljensten and Persoon, Biodegradable Osteochondral Implant, U.S. Patent Pub. No. 2009/0164014; Favis, et al., Porous Nanosheath Networks, Method of Making and Uses Thereof, U.S. Patent Pub. No. 2009/0087641; Hosoya, et al., Porous Polymer and Process For Producing the Same, U.S. Patent Pub. No. 2009/0045119; Andersson, Chitosan Compositions, U.S. Patent Pub. No. 2009/0022770; Xie, Three-Dimensional Hydrophilic Porous Structures for Fuel Cell Plates, U.S. Patent Pub. No. 2008/0292939; Ratner and Marshall, Novel Porous Materials, U.S. Patent Pub. No. 2008/0075752; Ma and Chen, Porous Materials having Multi-Sized Geometries, U.S. Patent Pub. No. 2007/0036844; Ma, Reverse Fabrication of Porous Materials, U.S. Patent Pub. No. 2002/0005600; Liu, et al., Porous Materials, Methods of Making and Uses, U.S. Patent Pub. No. 2011/0282444; Liu, et al., Porous Materials, Methods of Making and Uses, U.S. Patent Pub. No. 2011/0276133; Liu, et al., Porous Materials, Methods of Making and Uses, U.S. Patent Pub. No. 2012/0077010; Liu, et al., Porous Materials, Methods of Making and Uses, U.S. Patent Pub. No. 2012/0077012; and Liu, et al., Porous Materials, Methods of Making and Uses, each of which is incorporated by reference in its entirety.

In an embodiment, a porous material comprising a substance matrix defining an array of interconnected pores has a porosity sufficient to allow tissue growth into the array of interconnected pores. In aspects of this embodiment, a porous material comprising a substance matrix comprises a porosity of, e.g., about 40% of the total volume of a substance matrix, about 50% of the total volume of a substance matrix, about 60% of the total volume of a substance matrix, about 70% of the total volume of a substance matrix, about 80% of the total volume of a substance matrix, about 90% of the total volume of a substance matrix, about 95% of the total volume of a substance matrix, or about 97% of the total volume of a substance matrix. In other aspects of this embodiment, a porous material comprising a substance matrix comprises a porosity of, e.g., at least 40% of the total volume of a substance matrix, at least 50% of the total volume of a substance matrix, at least 60% of the total volume of a substance matrix, at least 70% of the total volume of a substance matrix, at least 80% of the total volume of a substance matrix, at least 90% of the total volume of a substance matrix, at least 95% of the total volume of a substance matrix, or at least 97% of the total volume of a substance matrix. In yet other aspects of this embodiment, a porous material comprising a substance matrix comprises a porosity of, e.g., at most 40% of the total volume of a substance matrix, at most 50% of the total volume of a substance matrix, at most 60% of the total volume of a substance matrix, at most 70% of the total volume of a substance matrix, at most 80% of the total volume of a substance matrix, at most 90% of the total volume of a substance matrix, at most 95% of the total volume of a substance matrix, or at most 97% of the total volume of a substance matrix. In yet other aspects of this embodiment, a porous material comprising a substance matrix comprises a porosity of, e.g., about 40% to about 97% of the total volume of a substance matrix, about 50% to about 97% of the total volume of a substance matrix, about 60% to about 97% of the total volume of a substance matrix, about 70% to about 97% of the total volume of a substance matrix, about 80% to about 97% of the total volume of a substance matrix, about 90% to about 97% of the total volume of a substance matrix, about 40% to about 95% of the total volume of a substance matrix, about 50% to about 95% of the total volume of a substance matrix, about 60% to about 95% of the total volume of a substance matrix, about 70% to about 95% of the total volume of a substance matrix, about 80% to about 95% of the total volume of a substance matrix, about 90% to about 95% of the total volume of a substance matrix, about 40% to about 90% of the total volume of a substance matrix, about 50% to about 90% of the total volume of a substance matrix, about 60% to about 90% of the total volume of a substance matrix, about 70% to about 90% of the total volume of a substance matrix, or about 80% to about 90% of the total volume of a substance matrix.

In another embodiment, a porous material comprising a substance matrix includes a surface openness sufficient to allow tissue growth into the array of interconnected pores. Surface openness, or first level openness, refers to the percentage area that the pores at the surface of a porous material are exposed to the surroundings. Surface openness may be determined by examining a top view image of a porous material. In aspects of this embodiment, a porous material comprising a substance matrix includes a surface openness of, e.g., about 45%, about 50%, about 55%, about 60%, about 65%, about 70%, about 75%, about 80%, about 85%, about 90%, about 93%, about 95%, about 97%, or about 100%. In other aspects of this embodiment, a porous material comprising a substance matrix includes a surface openness of, e.g., at least 45%, at least 50%, at least 55%, at least 60%, at least 65%, at least 70%, at least 75%, at least 80%, at least 85%, at least 90%, at least 93%, at least 95%, at least 97%, or at least 100%. In yet other aspects of this embodiment, a porous material comprising a substance matrix includes a surface openness of, e.g., about 45% to about 100%, about 50% to about 100%, about 55% to about 100%, about 60% to about 100%, about 65% to about 100%, about 70% to about 100%, about 75% to about 100%, about 80% to about 100%, or about 85% to about 100%.

In another embodiment, a porous material comprising a substance matrix includes an interconnectivity between pores sufficient to allow tissue growth into the array of interconnected pores. Interconnectivity, or second level openness, may be determined by measuring the area of visible openings or interconnections within each pore or surface opening from a top view image of a porous material and relating that area to the total area of the analyzed image. In aspects of this embodiment, a porous material comprising a substance matrix includes an interconnectivity between pores of, e.g., about 8%, about 9%, about 10%, about 11%, about 12%, about 13%, about 14%, about 15%, about 16%, about 17%, about 18%, about 19%, or about 20%. In other aspects of this embodiment, a porous material comprising a substance matrix includes an interconnectivity between pores of, e.g., at least 8%, at least 9%, at least 10%, at least 11%, at least 12%, at least 13%, at least 14%, at least 15%, at least 16%, at least 17%, at least 18%, at least 19%, or at least 20%. In yet other aspects of this embodiment, a porous material comprising a substance matrix includes an interconnectivity between pores of, e.g., about 8% to about 20%, about 9% to about 20%, about 10% to about 20%, about 11% to about 20%, about 12% to about 20%, about 13% to about 20%, about 14% to about 20%, or about 15% to about 20%. In yet other aspects of this embodiment, a porous material comprising a substance matrix includes an interconnectivity between pores of, e.g., about 6% to about 22%, about 7% to about 21%, about 8% to about 20%, about 9% to about 19%, about 10% to about 18%, about 11% to about 17%, about 12% to about 16%, or about 13% to about 15%.

In another embodiment, a porous material comprising a substance matrix includes a thickness to allow tissue growth into the array of interconnected pores. For example, a porous material may be from about 0.1 mm to about 1 mm, about 0.25 mm to about 1.5 mm, about 0.25 mm to about 2.5 mm, or about 0.5 mm to about 5 mm in thickness. In aspects of this embodiment, a porous material comprises a thickness of, e.g., about 100 μm, about 200 μm, about 300 μm, about 400 μm, about 500 μm, about 600 μm, about 700 μm, about 800 μm, about 900 μm, about 1 mm, about 2 mm, about 3 mm, about 4 mm, about 5 mm, about 6 mm, about 7 mm, about 8 mm, about 9 mm, or about 10 mm. In other aspects of this embodiment, a porous material comprises a thickness of, e.g., at least 100 μm, at least 200 μm, at least 300 μm, at least 400 μm, at least 500 μm, at least 600 μm, at least 700 μm, at least 800 μm, at least 900 μm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a porous material comprises a thickness of, e.g., at most 100 μm, at most 200 μm, at most 300 μm, at most 400 μm, at most 500 μm, at most 600 μm, at most 700 μm, at most 800 μm, at most 900 μm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a porous material comprises a thickness of, e.g., about 100 μm to about 500 μm, about 100 μm to about 1 mm, about 100 μm to about 5 mm, about 300 μm to about 1 mm, about 300 μm to about 2 mm, about 300 μm to about 3 mm, about 300 μm to about 4 mm, about 300 μm to about 5 mm, about 500 μm to about 1 mm, about 500 μm to about 2 mm, about 500 μm to about 3 mm, about 500 μm to about 4 mm, about 500 μm to about 5 mm, about 800 μm to about 1 mm, about 800 μm to about 2 mm, about 800 μm to about 3 mm, about 800 μm to about 4 mm, about 800 μm to about 5 mm, about 1 mm to about 2 mm, about 1 mm to about 3 mm, about 1 mm to about 4 mm, about 1 mm to about 5 mm, or about 1.5 mm to about 3.5 mm.

In another embodiment, a porous material comprising a substance matrix includes substantially no trapped porogens within the cured elastomer matrix. Porogens may become trapped within the cured substance matrix in situations where there is no interconnection with other pores. In aspects of this embodiment, a porous material comprising a substance matrix comprises, e.g., about 1 porogens/mg of porous material, about 2 porogens/mg of porous material, about 4 porogens/mg of porous material, about 5 porogens/mg of porous material, about 6 porogens/mg of porous material, about 8 porogens/mg of porous material, about 10 porogens/mg of porous material, about 15 porogens/mg of porous material, or about 20 porogens/mg of porous material. In other aspects of this embodiment, a porous material comprising a substance matrix comprises, e.g., at most 1 porogens/mg of porous material, at most 2 porogens/mg of porous material, at most 4 porogens/mg of porous material, at most 5 porogens/mg of porous material, at most 6 porogens/mg of porous material, at most 8 porogens/mg of porous material, at most 10 porogens/mg of porous material, at most 15 porogens/mg of porous material, or at most 20 porogens/mg of porous material. In yet other aspects of this embodiment, a porous material comprising a substance matrix comprises, e.g., about 1 porogens/mg of porous material to about 5 porogens/mg of porous material, about 1 porogens/mg of porous material to about 10 porogens/mg of porous material, about 1 porogens/mg of porous material to about 15 porogens/mg of porous material, or about 1 porogens/mg of porous material to about 20 porogens/mg of porous material.

In aspects of this embodiment, a porous material comprising a substance matrix comprises, e.g., about 50 porogens, about 100 porogens, about 200 porogens, about 300 porogens, about 400 porogens, about 500 porogens, about 600 porogens, about 700 porogens, about 800 porogens, about 900 porogens, or about 1000 porogens. In other aspects of this embodiment, a porous material comprising a substance matrix comprises, e.g., at most 50 porogens, at most 100 porogens, at most 200 porogens, at most 300 porogens, at most 400 porogens, at most 500 porogens, at most 600 porogens, at most 700 porogens, at most 800 porogens, at most 900 porogens, or at most 1000 porogens. In yet other aspects of this embodiment, a porous material comprising a substance matrix comprises, e.g., about 50 porogens to about 100 porogens, about 50 porogens to about 200 porogens, about 50 porogens to about 300 porogens, about 50 porogens to about 400 porogens, about 50 porogens to about 500 porogens, about 50 porogens to about 600 porogens, about 50 porogens to about 700 porogens, about 50 porogens to about 800 porogens, about 50 porogens to about 900 porogens, about 50 porogens to about 1000 porogens, about 200 porogens to about 300 porogens, about 200 porogens to about 400 porogens, about 200 porogens to about 500 porogens, about 200 porogens to about 600 porogens, about 200 porogens to about 700 porogens, about 200 porogens to about 800 porogens, about 200 porogens to about 900 porogens, about 200 porogens to about 1000 porogens, about 500 porogens to about 600 porogens, about 500 porogens to about 700 porogens, about 500 porogens to about 800 porogens, about 500 porogens to about 900 porogens, or about 500 porogens to about 1000 porogens.

In another embodiment, a porous material comprising a substance matrix includes pores where the diameter of the connections between pores is sufficient to allow tissue growth into the array of interconnected pores. In aspects of this embodiment, a porous material comprising a substance matrix includes pores where the diameter of the connections between pores is, e.g., about 10% the mean pore diameter, about 20% the mean pore diameter, about 30% the mean pore diameter, about 40% the mean pore diameter, about 50% the mean pore diameter, about 60% the mean pore diameter, about 70% the mean pore diameter, about 80% the mean pore diameter, or about 90% the mean pore diameter. In other aspects of this embodiment, a porous material comprising a substance matrix includes pores where the diameter of the connections between pores is, e.g., at least 10% the mean pore diameter, at least 20% the mean pore diameter, at least 30% the mean pore diameter, at least 40% the mean pore diameter, at least 50% the mean pore diameter, at least 60% the mean pore diameter, at least 70% the mean pore diameter, at least 80% the mean pore diameter, or at least 90% the mean pore diameter. In yet other aspects of this embodiment, a porous material comprising a substance matrix includes pores where the diameter of the connections between pores is, e.g., at most 10% the mean pore diameter, at most 20% the mean pore diameter, at most 30% the mean pore diameter, at most 40% the mean pore diameter, at most 50% the mean pore diameter, at most 60% the mean pore diameter, at most 70% the mean pore diameter, at most 80% the mean pore diameter, or at most 90% the mean pore diameter.

In one aspect, a biocompatible implantable device comprises a porous material formed by methods using the porogen compositions disclosed herein.

The present specification discloses in part, biocompatible implantable device comprising a layer of porous material as disclosed herein, wherein the porous material covers a surface of the device. See, e.g., FIG. 2, and FIGS. 4-8. As used herein, the term "implantable" refers to any material that can be embedded into, or attached to, tissue, muscle, organ or any other part of an animal body. As used herein, the term "animal" includes all mammals including a human. A biocompatible implantable device is synonymous with "medical device", "biomedical device", "implantable medical device" or "implantable biomedical device" and includes, without limitation, pacemakers, dura matter substitutes, implantable cardiac defibrillators, tissue expanders, and tissue implants used for prosthetic, reconstructive, or aesthetic purposes, like breast implants, muscle implants or implants that reduce or prevent scarring. Examples of biocompatible implantable devices that the porous material disclosed herein can be attached to are described in, e.g., Schuessler, Rotational Molding System for Medical Articles, U.S. Pat. No. 7,628,604; Smith, Mastopexy Stabilization Apparatus and Method, U.S. Pat. No. 7,081,135; Knisley, Inflatable Prosthetic Device, U.S. Pat. No. 6,936,068; Falcon, Reinforced Radius Mammary Prostheses and Soft Tissue Expanders, U.S. Pat. No. 6,605,116; Schuessler, Rotational Molding of Medical Articles, U.S. Pat. No. 6,602,452; Murphy, Seamless Breast Prosthesis, U.S. Pat. No. 6,074,421; Knowlton, Segmental Breast Expander For Use in Breast Reconstruction, U.S. Pat. No. 6,071,309; VanBeek, Mechanical Tissue Expander, U.S. Pat. No. 5,882,353; Hunter, Soft Tissue Implants and Anti-Scarring Agents, Schuessler, Self-Sealing Shell For Inflatable Prostheses, U.S. Patent Pub. No. 2010/0049317; U.S. 2009/0214652; Schraga, Medical Implant Containing Detection Enhancing Agent and Method For Detecting Content Leakage, U.S. Patent Pub. No. 2009/0157180; Schuessler, All-Barrier Elastomeric Gel-Filled Breast Prosthesis, U.S. Patent Pub. No. 2009/0030515; Connell, Differential Tissue Expander Implant, U.S. Patent Pub. No. 2007/0233273; and Hunter, Medical implants and Anti-Scarring Agents, U.S. Patent Pub. No. 2006/0147492; Van Epps, Soft Filled Prosthesis Shell with Discrete Fixation Surfaces, International Patent Publication WO/2010/019761; Schuessler, Self-Sealing Shell for Inflatable Prosthesis, International Patent Publication WO/2010/022130; Yacoub, Prosthesis Implant Shell, International Application No. PCT/US09/61045, each of which is hereby incorporated by reference in its entirety.

A biocompatible implantable device disclosed herein can be implanted into the soft tissue of an animal during the normal operation of the device. Such implantable devices may be completely implanted into the soft tissue of an animal body (i.e., the entire device is implanted within the body), or the device may be partially implanted into an animal body (i.e., only part of the device is implanted within an animal body, the remainder of the device being located outside of the animal body). A biocompatible implantable device disclosed herein can also be affixed to soft tissue of an animal during the normal operation of the medical device. Such devices are typically affixed to the skin of an animal body.

The present specification discloses, in part, a porous material that covers a surface of the biocompatible implantable device. Any of the porous materials disclosed herein can be used as the porous material covering a surface of a biocompatible implantable device. In general, the surface of a biocompatible implantable device is one exposed to the surrounding tissue of an animal in a manner that promotes tissue growth, and/or reduces or prevents formation of fibrous capsules that can result in capsular contracture or scarring.

A biocompatible implantable device may be a base shell comprising a single layer or a plurality of layers. In an aspect of this embodiment, a base shell comprises one or more inner base layer of a substance or elastomer, a barrier or reinforcement layer and one or more outer base layer of a substance or an elastomer, wherein the barrier or reinforcement layer lays in between the one or more inner base layers and one or more outer base layers. In another aspect of this embodiment, a base shell comprises one inner base layer of a substance or an elastomer, a barrier or reinforcement layer and two outer base layer of a substance or an elastomer. In yet another aspect of this embodiment, a base shell comprises two inner base layers of a substance or an elastomer, a barrier or reinforcement layer and two outer base layers of a substance or an elastomer. In still another aspect of this embodiment, a base shell comprises two inner base layers of a substance or an elastomer, a barrier or reinforcement layer and three outer base layers of a substance or an elastomer. The barrier or reinforcement layer may comprise a synthetic polymer mesh or fabric. Exemplary base shells include, without limitation, a breast implant shell or a tissue expander shell.

Thus, in an embodiment, a porous material covers the entire surface of a biocompatible implantable device. In another embodiment, a porous material covers a portion of a surface of a biocompatible implantable device. In aspects of this embodiment, a porous material covers to a front surface of a biocompatible implantable device or a back surface of a biocompatible implantable device. In other aspects, a porous material covers only to, e.g., about 20%, about 30%, about 40%, about 50%, about 60%, about 70% about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70% at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70% at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material covering a biocompatible implantable device can be of any thickness with the proviso that the material thickness allows tissue growth within the array of interconnected of pores of a substance matrix in a manner sufficient to reduce or prevent formation of fibrous capsules that can result in capsular contracture or scarring.

Thus, in an embodiment, a layer of porous material covering a biocompatible implantable device is of a thickness that allows tissue growth within the array of interconnected of pores of a substance matrix in a manner sufficient to reduce or prevent formation of fibrous capsules that can result in capsular contracture or scarring. In aspects of this embodiment, a layer porous material covering a biocompatible implantable device comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a layer porous material covering a biocompatible implantable device comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer porous material covering a biocompatible implantable device comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer porous material covering a biocompatible implantable device comprises a thickness of, e.g., about 100 µm to about 500 µm, about 100 µm to about 1 mm, about 100 µm to about 5 mm, about 300 µm to about 1 mm, about 300 µm to about 2 mm, about 300 µm to about 3 mm, about 300 µm to about 4 mm, about 300 µm to about 5 mm, about 500 µm to about 1 mm, about 500 µm to about 2 mm, about 500 µm to about 3 mm, about 500 µm to about 4 mm, about 500 µm to about 5 mm, about 800 µm to about 1 mm, about 800 µm to about 2 mm, about 800 µm to about 3 mm, about 800 µm to about 4 mm, about 800 µm to about 5 mm, about 1 mm to about 2 mm, about 1 mm to about 3 mm, about 1 mm to about 4 mm, about 1 mm to about 5 mm, or about 1.5 mm to about 3.5 mm.

The present specification discloses in part, a method for making biocompatible implantable device comprising a porous material. In an aspect, a method for making biocompatible implantable device comprises the step of attaching a porous material to the surface of a biocompatible implantable device. In another aspect, a method for making biocompatible implantable device comprises the steps of a) preparing a surface of a biocompatible implantable device surface to receive porous material; b) attaching a porous material to the prepared surface of the device. Any of the porous materials disclosed herein can be used as the porous material attached to a surface of a biocompatible implantable device.

In yet another aspect, a method for making biocompatible implantable device comprising the step of: a) coating a mandrel with a substance base; b) curing the substance base to form a base layer; c) coating the cured base layer with a substance base; d) coating the substance base with porogens to form a substance coated porogen mixture, the porogens comprise a shell material and a core material, wherein the shell material as disclosed herein; e) treating the elastomer coated porogen mixture to form a porogen scaffold comprising fused porogens and cure the substance base; and f) removing the porogen scaffold, wherein porogen scaffold removal results in a porous material, the porous material comprising a non-degradable, biocompatible, elastomer matrix defining an array of interconnected pores. In this method steps (c) and (d) can be repeated multiple times until the desired thickness of the material layer is achieved.

The present specification discloses, in part, preparing a surface of a biocompatible implantable device to receive porous material. Preparing a surface of a biocompatible implantable device to receive porous material can be accomplished by any technique that does not destroy the desired properties of the porous material or the biocompatible implantable device. As a non-limiting example, a surface of a biocompatible implantable device can be prepared by applying a bonding substance. Non-limiting examples of bonding substances include silicone adhesives, such as, e.g., RTV silicone and HTV silicone. The bonding substance is applied to the surface of a biocompatible implantable device, the porous material, or both, using any method known in the art, such as, e.g., cast coating, spray coating, dip coating, curtain coating, knife coating, brush coating, vapor deposition coating, and the like.

The present specification discloses, in part, attaching a porous material to a surface of a biocompatible implantable device. The porous material can be attached to the entire surface of the device, or only to portions of the surface of the device. As a non-limiting example, porous material is attached only to the front surface of the device or only the back surface of the device. Attachment of a porous material to a surface of a biocompatible implantable device can be accomplished by any technique that does not destroy the desired properties of the porous material or the biocompatible implantable device.

For example, attachment can occur by adhering an already formed porous material onto a surface of a biocompatible implantable device using methods known in the art, such as, e.g., gluing, bonding, melting. For instance, a dispersion of silicone is applied as an adhesive onto a surface of a biocompatible implantable device, a porous material sheet, or both, and then the two materials are placed together in a manner that allows the adhesive to attached the porous material to the surface of the device in such a way that there are no wrinkles on the surface of the device. The silicone adhesive is allowed to cure and then the excess material is cut off creating a uniform seam around the device. This process results in a biocompatible implantable device comprising a porous material disclosed herein. Examples 2 and 4 illustrate method of this type of attachment.

Alternatively, attachment can occur by forming the porous material directly onto a surface of a biocompatible implantable device using methods known in the art, such as, e.g., cast coating, spray coating, dip coating, curtain coating, knife coating, brush coating, vapor deposition coating, and the like. For instance, a substance base is applied to a mandrel and cured to form a base layer of cured elastomer. The base layer is then initially coated with a substance base and then subsequently with porogens to create a substance coated porogen mixture. This mixture is then treated as disclosed herein to form a porogen scaffold and cure the elastomer. The porogen scaffold is then removed, leaving a layer of porous material on the surface of the device. The thickness of the porous material layer can be increased by repeated coatings of additional substance base and porogens. Examples 5-8 illustrate method of this type of attachment.

Regardless of the method of attachment, the porous material can be applied to the entire surface of a biocompatible implantable device, or only to portions of the surface of a biocompatible implantable device. As a non-limiting example, porous material is applied only to the front surface of a biocompatible implantable device or only the back surface of a biocompatible implantable device.

Thus, in an embodiment, a porous material is attached to a surface of a biocompatible implantable device by bonding a porous material to a surface of a biocompatible implantable device. In aspects of this embodiment, a porous material is attached to a surface of a biocompatible implantable device by gluing, bonding, or melting the porous material to a surface of a biocompatible implantable device.

In another embodiment, a porous material is attached to a surface of a biocompatible implantable device by forming the porous material onto a surface of a biocompatible implantable device. In aspects of this embodiment, a porous material is attached to a surface of a biocompatible implantable device by cast coating, spray coating, dip coating, curtain coating, knife coating, brush coating, or vapor deposition coating.

In another aspect of this embodiment, forming a porous material on a surface of a biocompatible implantable device comprises coating a cured substance base layer with a substance base and then coating the uncured substance base with porogens to form a substance coated porogen mixture. In other aspects of this embodiment, coating a cured substance base layer with an uncured substance base and then coating the uncured substance base with porogens to form a substance coated porogen mixture can be repeated, e.g., at least once, at least twice, at least three times, at least four times, at least five times, at least six times, at least seven times, at least eight times, at least nine times, or at least ten times, before the mixture is treated.

In another embodiment, a porous material is applied to the entire surface of a biocompatible implantable device. In another embodiment, a porous material is applied to a portion of a surface of a biocompatible implantable device. In aspects of this embodiment, a porous material is applied to a front surface of a biocompatible implantable device or a back surface of a biocompatible implantable device. In other aspects, a porous material is applied only to, e.g., about 20%, about 30%, about 40%, about 50%, about 60%, about 70% about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70% at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70% at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material applied to a biocompatible implantable device can be of any thickness with the proviso that the material thickness allows tissue growth within the array of interconnected of pores of a substance matrix in a manner sufficient to reduce or prevent formation of fibrous capsules that can result in capsular contracture or scarring.

Thus, in an embodiment, a layer of porous material applied to a biocompatible implantable device is of a thickness that allows tissue growth within the array of interconnected of pores of a substance matrix in a manner sufficient to reduce or prevent formation of fibrous capsules that can result in capsular contracture or scarring. In aspects of this embodiment, a layer porous material applied to a biocompatible implantable device comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a layer porous material applied to a biocompatible implantable device comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer porous material applied to a biocompatible implantable device comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer porous material applied to a biocompatible implantable device comprises a thickness of, e.g., about 100 µm to about 500 µm, about 100 µm to about 1 mm, about 100 µm to about 5 mm, about 300 µm to about 1 mm, about 300 µm to about 2 mm, about 300 µm to about 3 mm, about 300 µm to about 4 mm, about 300 µm to about 5 mm, about 500 µm to about 1 mm, about 500 µm to about 2 mm, about 500 µm to about 3 mm, about 500 µm to about 4 mm, about 500 µm to about 5 mm, about 800 µm to about 1 mm, about 800 µm to about 2 mm, about 800 µm to about 3 mm, about 800 µm to about 4 mm, about 800 µm to about 5 mm, about 1 mm to about 2 mm, about 1 mm to about 3 mm, about 1 mm to about 4 mm, about 1 mm to about 5 mm, or about 1.5 mm to about 3.5 mm.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 75 µm or less, has fiber disorganization comprising 50% or more of the fibers that are not parallel to the prosthesis surface, has tissue growth into the biomaterial of the prosthesis of 100 µm or more, has less than 40% collagen content, adheres to tissue with a peak force of at least 8 N and/or and has a stiffness of 20 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 50 µm or less, has fiber disorganization comprising 60% or more of the fibers that are parallel to the prosthesis surface, has tissue growth into the biomaterial of the prosthesis of 125 µm or more, has less than 30% collagen content, adheres to tissue with a peak force of at least 9 N and/or and has a stiffness of 15 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 25 µm or less, has fiber disorganization comprising 70% or more of the fibers that are not parallel to the prosthesis surface, has tissue growth into the biomaterial of the prosthesis of 150 µm or more, has less than 20% collagen content, adheres to tissue with a peak force of at least 10 N and/or and has a stiffness of 10 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of about 5 µm to about 75 µm, has fiber disorganization comprising about 50% to about 90% of the fibers that are not parallel to the prosthesis surface, has tissue growth into the biomaterial of the prosthesis of about 100 µm to about 300 µm, has about 5% to about 40% collagen content, adheres to tissue with a peak force of about 8 N to about 11 N, and/or and has a stiffness of about 5 mmHg/mL to about 20 mm Hg/m L.

EXAMPLES

The following examples illustrate representative embodiments now contemplated, but should not be construed to limit the disclosed porous materials, methods of forming such porous materials, biocompatible implantable devices comprising such porous materials, and methods of making such biocompatible implantable devices.

Example 1

A Method of Making a Porous Material Sheet

This example illustrates how to make a sheet of porous material using the porogen compositions disclosed herein.

To coat porogens with a substance, an appropriate amount of porogens comprising a sugar core of about 335 µm and a polyethylene glycol shell of about 15 µm were mixed with an appropriate amount of about 35% (v/v) silicone in xylene (PN-3206-1; NuSil Technology LLC, Carpinteria, Calif.). In other experiments, the porogen composition used were porogens comprising a sugar core of about 335 µm and a polyethylene glycol shell of about 53 µm, porogens comprising a sugar core of about 390 µm and a polyethylene glycol shell of about 83 µm, or porogens comprising a sugar core of about 460 µm and a polyethylene glycol shell of about 104 µm. The mixture was filtered through a 43 µm sieve to remove the excess silicone and was poured into an about 20 cm×20 cm square mold coated with a non-stick surface.

To treat a substance coated porogen mixture to allow fusing of the porogens to form a porogen scaffold and stabilization of the substance, the porogen/silicone mixture was placed into an oven and heated at a temperature of about 75° C. for about 60 min, and then about 126° C. for about 75 minutes. In another experiments, the porogen/silicone mixture was treated by placing into an oven and heated at a temperature of about 126° C. for about 75 minutes, or heated at a temperature of about 145° C. for about 150 minutes, or heated at a temperature of about 126° C. for about 85 min, and then about 30° C. for about 60 minutes. After curing, the sheet of cured elastomer coated porogen scaffold was removed.

To remove a porogen scaffold from the cured substance, the cured elastomer/porogen scaffold was immersed in hot water. After about 30 minutes, the hot water was removed and the resulting 20 cm×20 cm×1.5 mm sheet of porous material was air dried at an ambient temperature of about 18° C. to about 22° C. This process results in a porous material sheet as disclosed herein.

A sample from the sheet of porous material can be characterized by microCT analysis and/or scanning electron microscopy (SEM).

Example 2

A Method of Making a Porous Material Sheet

This example illustrates how to make a sheet of porous material using the porogen compositions disclosed herein.

To coat porogens with a substance, an appropriate amount of porogens were mixed with an appropriate amount of about 35% (v/v) silicone in xylene (PN-3206-1; NuSil Technology LLC, Carpinteria, Calif.). The porogens comprised a core of about 450 µm to about 500 µm in diameter comprising sucrose and corn starch and a PEG shell of about 50 µm to about 75 µm in depth, for a mean porogen diameter of about 550 µm The mixture was filtered through a 43 µm sieve to remove the excess silicone and was poured into an about 30 cm×30 cm square mold coated with a non-stick surface.

To treat a substance coated porogen mixture to allow fusing of the porogens to form a porogen scaffold and stabilization of the substance, the porogen/silicone mixture was placed into an oven and heated at a temperature of about 126° C. for about 75 minutes. In another experiments, the porogen/silicone mixture was treated by placing into an oven and heated at a temperature of about 126° C. for about 60 minutes to about 90 minutes. After curing, the sheet of cured elastomer coated porogen scaffold was removed.

To remove a porogen scaffold from the cured substance, the cured elastomer/porogen scaffold was immersed in hot water. After about 30 minutes, the hot water was removed and the resulting 30 cm×30 cm×2 mm sheet of porous material was air dried at an ambient temperature of about 18° C. to about 22° C. This process results in a porous material sheet as disclosed herein.

A sample from the sheet of porous material can be characterized by microCT analysis and/or scanning electron microscopy (SEM).

Example 3

A Method of Making a Biocompatible Implantable Device Comprising a Porous Material This example illustrates how to make a biocompatible implantable device comprising a porous material formed using the porogen compositions disclosed herein.

Sheets of porous material comprising an elastomer matrix defining an interconnected array of pores is obtained as described in Example 1 or 2.

Figure 2A:
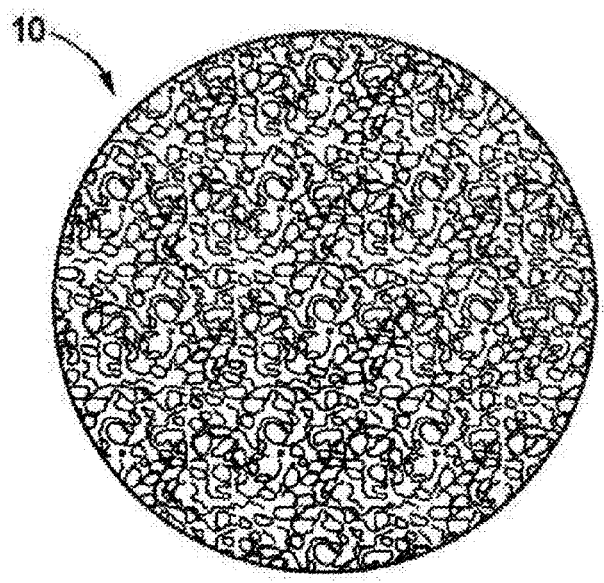
FIG. 2A is a top view of an implantable device covered with a porous material.
Figure 2B:
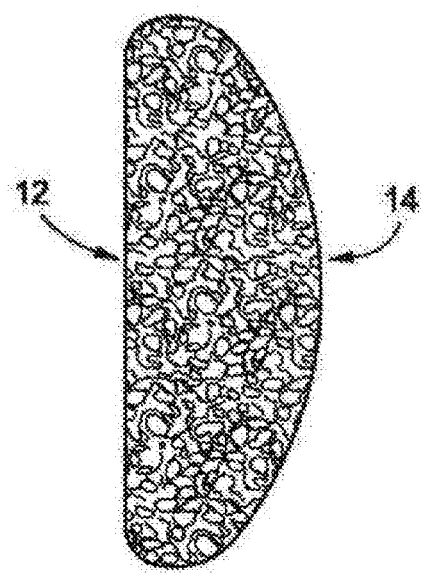
FIG. 2B is a side view of an implantable device covered with a porous material.
Figure 2C:
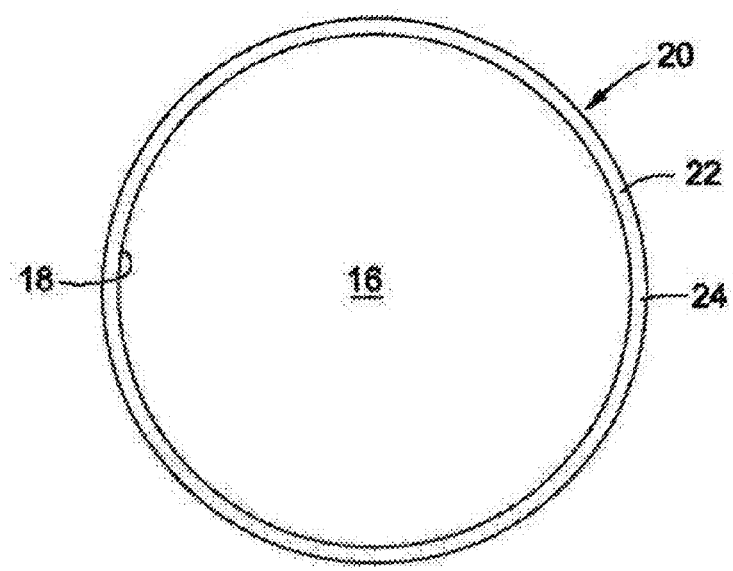
FIGS. 2C and 2D illustrate the cross-sectional view of the biocompatible implantable device covered with a porous material.
Figure 2D:
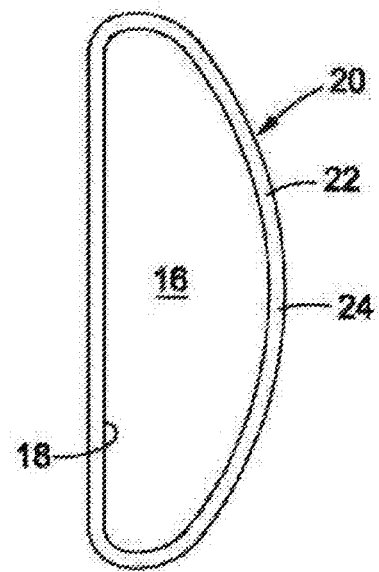

To attach a porous material to a biocompatible implantable device, a first porous material sheet is coated with a thin layer of silicone and then placed in the bottom cavity of a mold, adhesive side up. A biocompatible implantable device is then placed on top of the material surface coated with the adhesive. A second porous material sheet is then coated with a thin layer of silicone and applied to the uncovered surface of the biocompatible implantable device. The top piece of the mold cavity is then fixed in place pressing the two material sheets together creating a uniform interface. The silicone adhesive is allowed to cure by placing the covered device into an oven and heated at a temperature of about 126° C. for about 75 minutes. After curing, excess material is trimmed off creating a uniform seam around the biocompatible implantable device. This process results in a biocompatible implantable device 10 as disclosed herein (FIG. 2). FIG. 2A is a top view of an implantable device covered with a porous material 10. FIG. 2B is a side view of an implantable device covered with a porous material 10 to show a bottom 12 of the implantable device 10 and a top 14 of the implantable device 10. FIGS. 2C and 2D illustrate the cross-sectional view of the biocompatible implantable device covered with a porous material 10 to show an implantable device 16, a porous material layer 20 including an internal surface 22 and an external surface 24, where the internal surface 22 is attached to an implantable device surface 18. Due to the presence of the porous material on the device surface of the biocompatible implantable device there will be a reduction or prevention of the formation of fibrous capsules that can result in capsular contracture or scarring.

Alternatively, the porous material can be laminated onto a biocompatible implantable device while the device is still on a mandrel. In this process, a first porous material sheet is coated with a thin layer of silicone and then draped over the device on the mandrel in such a way that there are no wrinkles on the surface. After curing the silicone adhesive, as described above, another coating of silicone is applied to the uncovered surface of the biocompatible implantable device and a second porous material is stretched up to cover the back of the device. After curing the silicone adhesive, as described above, the biocompatible implantable device is then taken off the mandrel and the excess porous material is trimmed to create a uniform seam around the device. This process results in a biocompatible implantable device comprising a porous material as disclosed herein. See, e.g., FIG. 2.

Example 4

A Method of Making a Porous Material Shell

This example illustrates how to make a porous material shell using the porogen compositions disclosed herein.

To coat porogens with a substance, an appropriate amount of a porogen composition comprising a sugar core of about 335 µm and a polyethylene glycol shell of about 53 µm are mixed with an appropriate amount of about 35% (v/v) silicone in xylene (PN-3206-1; NuSil Technology LLC, Carpinteria, Calif.). In other experiments, the porogen composition used are porogens comprising a sugar core of about 335 µm and a polyethylene glycol shell of about 65 µm, porogens comprising a sugar core of about 320 µm and a polyethylene glycol shell of about 30 µm, or porogens comprising a sugar core of about 350 µm and a polyethylene glycol shell of about 50 μm. Alternatively, porogens comprising a core of about 450 μm to about 500 μm in diameter comprising sucrose and corn starch and a PEG shell of about 50 μm to about 75 μm in depth, for a mean porogen diameter of about 550 μm may be used. The mixture is filtered through a 43 μm sieve to remove the excess silicone.

To pour a substance coated porogen mixture into a mold, the filtered elastomer coated porogen mixture is poured into a mold in the shape of a breast implant shell and the mold is mechanically agitated to pack firmly the mixture. The thickness of the shell is controlled based upon the design of the shell mold.

To treat a substance coated porogen mixture to allow fusing of the porogens to form a porogen scaffold and cure the elastomer, the porogen/silicone mixture is placed into an oven and is heated at a temperature of about 75° C. for about 45 min, and then about 126° C. for about 75 minutes. In another experiments, the porogen/silicone mixture is treated by placing into an oven and heated at a temperature of about 126° C. for about 75 minutes, or heated at a temperature of about 145° C. for about 60 minutes. After treating, the shell mold is dismantled and the cured elastomer coated porogen scaffold is removed.

Figure 3A:
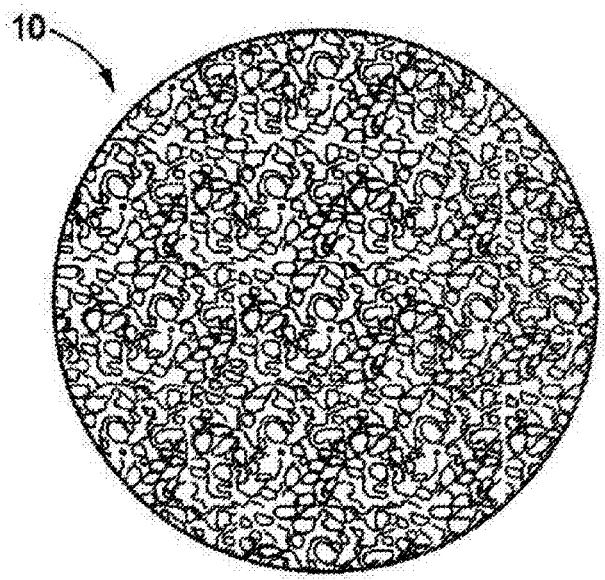
FIG. 3A is a top view of a material shell.
Figure 3B:
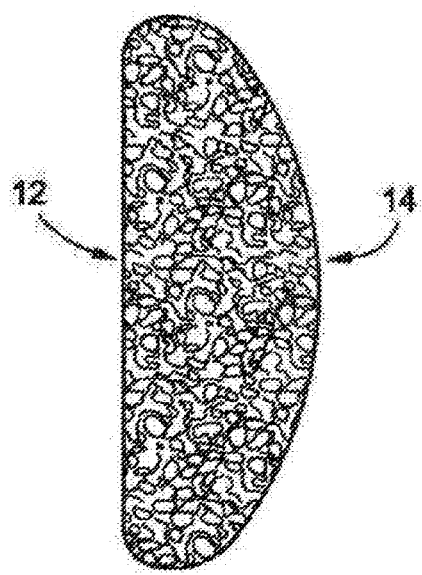
FIG. 3B is a side view of a material shell.
Figure 3C:
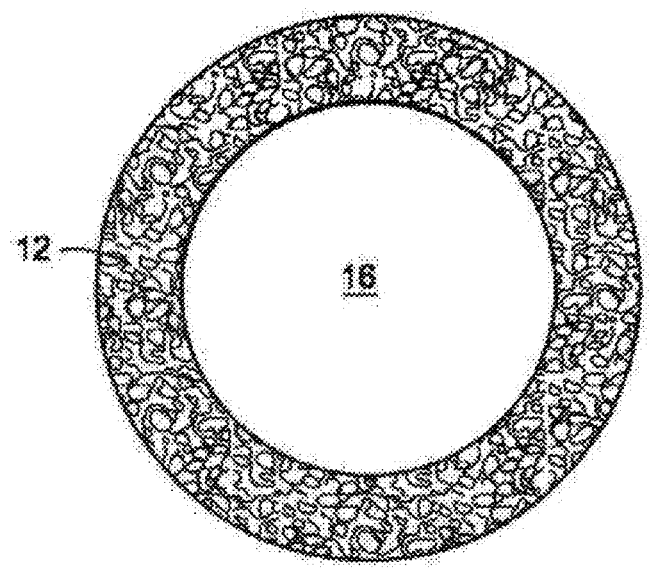
FIG. 3C is a bottom view of a material shell.
Figure 3D:
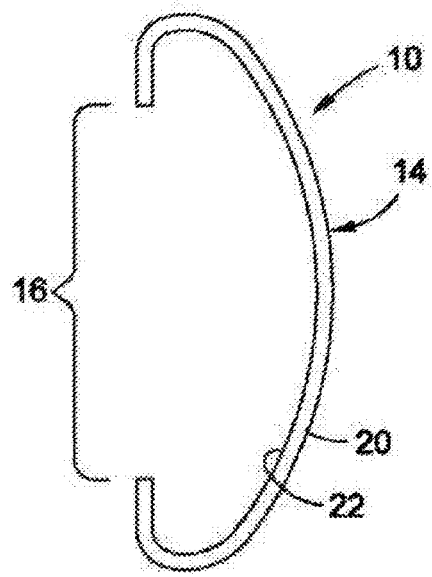
FIG. 3D illustrate the cross-sectional view of the material shell.

To remove a porogen scaffold from the cured substance, the cured elastomer/porogen scaffold is immersed in hot water. After about 3 hours, the hot water is removed and the resulting shell of porous material is dried in an oven of about 126° C. for 30 minutes. This process results in a porous material shell 10 as disclosed herein (FIG. 3). FIG. 3A is a top view of a material shell 10. FIG. 2B is a side view of a material shell 10 to show a bottom 12 of the material shell 10 and a top 14 of the material shell 10. FIG. 3C is a bottom view of a material shell 10 to show a hole 16 from which a biocompatible implantable device may be subsequently inserted through. FIG. 3D illustrate the cross-sectional view of the material shell 10 to show the hole 16, an internal surface 20 of the material shell 10 and an external surface 22 of the material shell 10.

A sample from the sheet of porous material can be characterized by microCT analysis and/or scanning electron microscopy (SEM).

Example 5

A Method of Making a Biocompatible Implantable Device Comprising a Porous Material This example illustrates how to make a biocompatible implantable device comprising a porous material formed using the porogen compositions disclosed herein.

A porous material shell comprising a matrix defining an interconnected array of pores is obtained as described in Example 4.

Figure 4A:
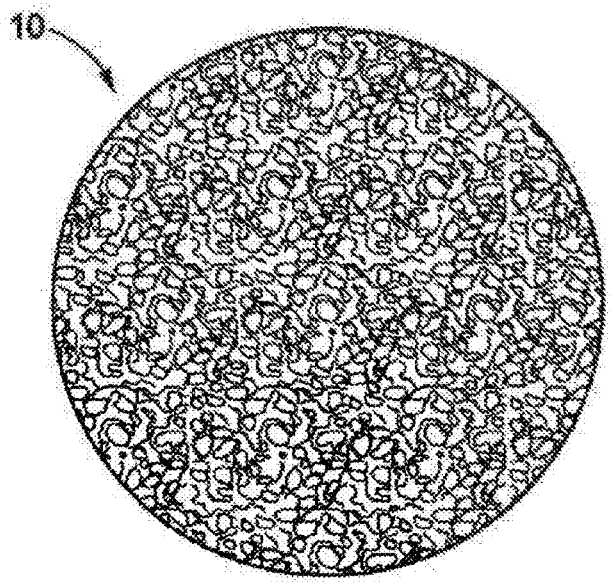
FIG. 4A is a top view of an implantable device covered with a porous material.
Figure 4B:
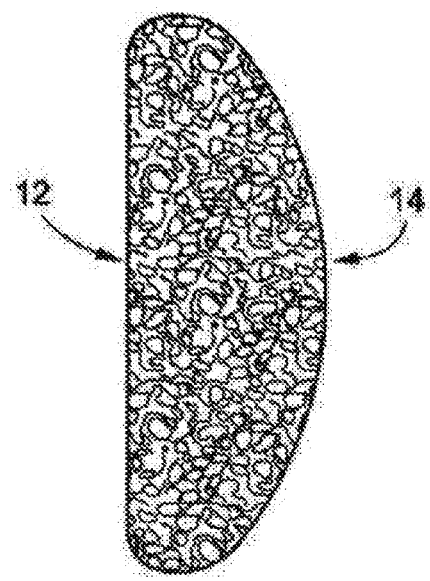
FIG. 4B is a side view of an implantable device covered with a porous material.
Figure 4C:
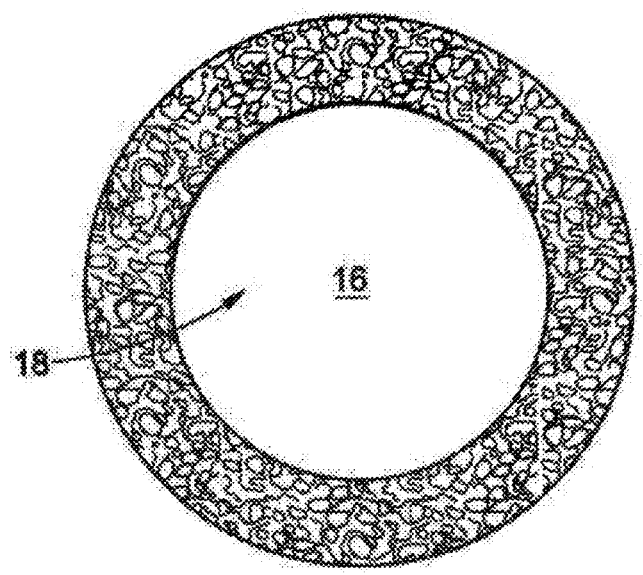
FIG. 4C is a bottom view of a biocompatible implantable device covered with a porous material.
Figure 4D:
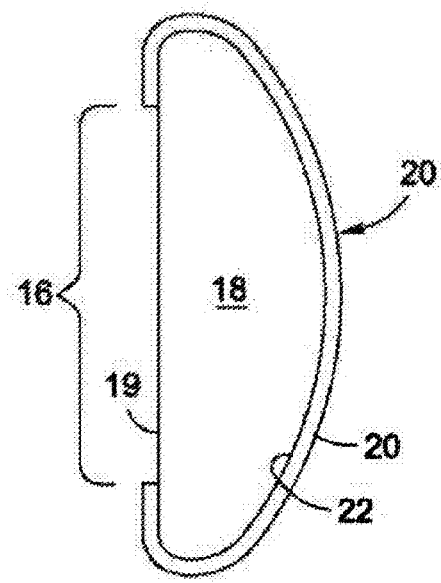
FIG. 4D illustrates the cross-sectional view of the biocompatible implantable device covered with a porous material.

To attach the porous material shell to a biocompatible implantable device, the surface of the device is coated with a thin layer of silicone. The material shell is then placed over the adhesive coated device in a manner that ensures no wrinkles in the material form. The silicone adhesive is allowed to cure by placing the covered device into an oven and heating at a temperature of 126° C. for 75 minutes. After curing, excess material is trimmed off creating a uniform seam around the biocompatible implantable device. This process results in a biocompatible implantable device comprising a porous material 10 as disclosed herein (FIG. 4). FIG. 4A is a top view of an implantable device covered with a porous material 10. FIG. 4B is a side view of an implantable device covered with a porous material 10 to show a bottom 12 of the implantable device 10 and a top 14 of the implantable device 10. FIG. 4C is a bottom view of a biocompatible implantable device covered with a porous material 10 to show a hole 16 and an implantable device 18. FIG. 4D illustrates the cross-sectional view of the biocompatible implantable device covered with a porous material 10 to show an implantable device 18, a porous material layer 20 including an internal surface 22 and an external surface 24, where the internal surface 22 is attached to implantable device surface 19. Due to the presence of the porous material on the device surface of the biocompatible implantable device there will be a reduction or prevention of the formation of fibrous capsules that can result in capsular contracture or scarring.

Example 6

A Method of Making an Implant Comprising a Porous Material

This example illustrates how to make an implant comprising a porous material disclosed herein of about 0.5 mm to about 1.5 mm in thickness.

To preparing the surface of a device to receive a porous material, a base layer of 35% (w/w) silicone in xylene (PN-3206-1; NuSil Technology LLC, Carpinteria, Calif.) was coated on a mandrel (LR-10), placed into an oven, and cured at a temperature of about 126° C. for about 75 minutes. Alternatively, a previously made biocompatible implantable device, such as, e.g., a base shell disclosed herein, can be attached to a mandrel and then processed beginning with the next step.

To coat the base layer with a mixture comprising a substance and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 μm and a polyethylene glycol shell of about 53 μm until the maximum amount of porogens were absorbed into the uncured silicone. In other experiments, the porogen composition used were porogens comprising a sugar core of about 335 μm and a polyethylene glycol shell of about 60 μm, porogens comprising a sugar core of about 390 μm and a polyethylene glycol shell of about 83 μm, or porogens comprising a sugar core of about 460 μm and a polyethylene glycol shell of about 104 μm. The mandrel with the uncured silicone/porogen coating was air dried for about 60 minutes to allow the xylene to evaporate.

To treat a substance coated porogen mixture to allow fusing of the porogens to form a porogen scaffold and stabilization of the substance, the mandrel coated with the uncured silicone/porogen mixture was placed into an oven and cured at a temperature of about 75° C. for 30 min, and then about 126° C. for 75 minutes. In another experiments, the porogen/silicone mixture was treated by placing into an oven and heated at a temperature of about 126° C. for about 75 minutes, or heated at a temperature of about 145° C. for about 60 minutes.

To remove porogen scaffold, the cured silicone/porogen scaffold was immersed in hot water. After about 3 hours, the hot water was removed and the resulting implant comprising a porous material of about 0.5 mm to about 1.5 mm was dried in an oven of about 126° C. for 30 minutes. This process resulted in a biocompatible implantable device comprising a porous material as disclosed herein. See, e.g., FIG. 2 and FIG. 4.

Figure 5A:
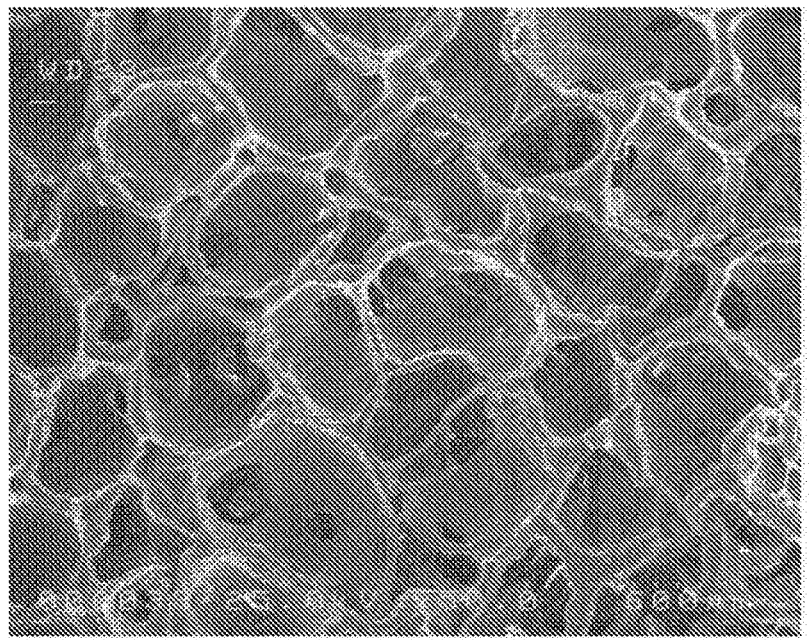
FIGS. 5A and 5B show an analysis of a porous material as disclosed in the present specification.
Figure 5B:
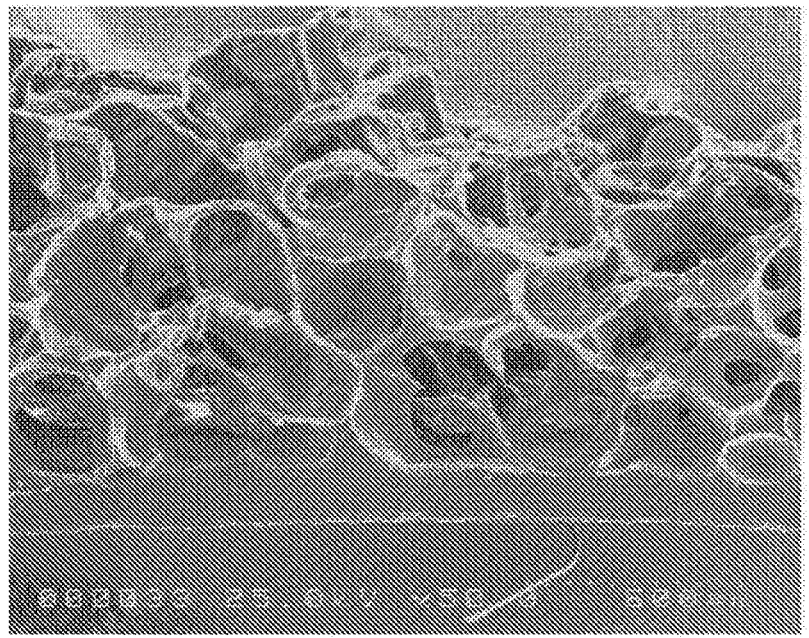

A sample from the implant was characterized by microCT analysis. This analysis revealed that the porous material was about 1.4 mm to about 1.6 mm in thickness with a porosity of about 80%, with open pores comprising at least 80% and close pores comprising at most 0.07%. The mean strut thickness was about 90 µm, with a mean pore size of about 400 µm. The porous material has a compressive modulus of about 20 kPa, elongation at break of about 350%, and a tensile strength of about 14 µPa. Scanning electron analysis of the porous material is shown in FIG. 5.

To increase the thickness of the porous material covering the base layer, multiple dippings were performed to produce a mandrel coated with multiple layers of an uncured silicone/porogen mixture. Dippings were repeated until the desired thickness is achieved. Examples 7-9 below describe specific examples of this multiple dipping technique.

Example 7

A Method of Making an Implant Comprising a Porous Material

This example illustrates how to make an implant comprising a porous material of about 1 mm to about 2.5 mm in thickness formed using the porogen compositions disclosed herein.

A mandrel comprising a base layer of elastomer was prepared as described in Example 6 or a previously made biocompatible implantable device, such as, e.g., a base shell disclosed herein, can be attached to the mandrel as described in Example 6 and then processed beginning with the next step.

To coat the base layer with a mixture comprising a substance and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 µm and a polyethylene glycol shell of about 53 µm until the maximum amount of porogens were absorbed into the uncured silicone. In other experiments, the porogen composition used were porogens comprising a sugar core of about 335 µm and a polyethylene glycol shell of about 60 µm, porogens comprising a sugar core of about 390 µm and a polyethylene glycol shell of about 83 µm, or porogens comprising a sugar core of about 460 µm and a polyethylene glycol shell of about 104 µm. The mandrel with the uncured silicone/porogen mixture coating was air dried for about 60 minutes to allow the xylene to evaporate. After xylene evaporation, the mandrel coated with the uncured silicone/porogen mixture was dipped first in about 35% (w/w) silicone in xylene, air dried to allow xylene evaporation (about 3 minutes), and then dipped in porogen composition until the maximum amount of porogens were absorbed into the uncured silicone. The mandrel with the second coating of uncured silicone/porogen mixture was air dried for about 60 minutes to allow the xylene to evaporate.

The mandrel comprising the two coats of uncured silicone/porogen mixture was treating as described in Example 6.

Removal of the porogen scaffold was as described in Example 5, and the resulting implant comprising a porous material of about 1 mm to about 2.5 mm was dried in an oven of about 126° C. for 30 minutes. This process resulted in a biocompatible implantable device comprising a porous material as disclosed herein. See, e.g., FIG. 2 and FIG. 4.

Figure 6A:
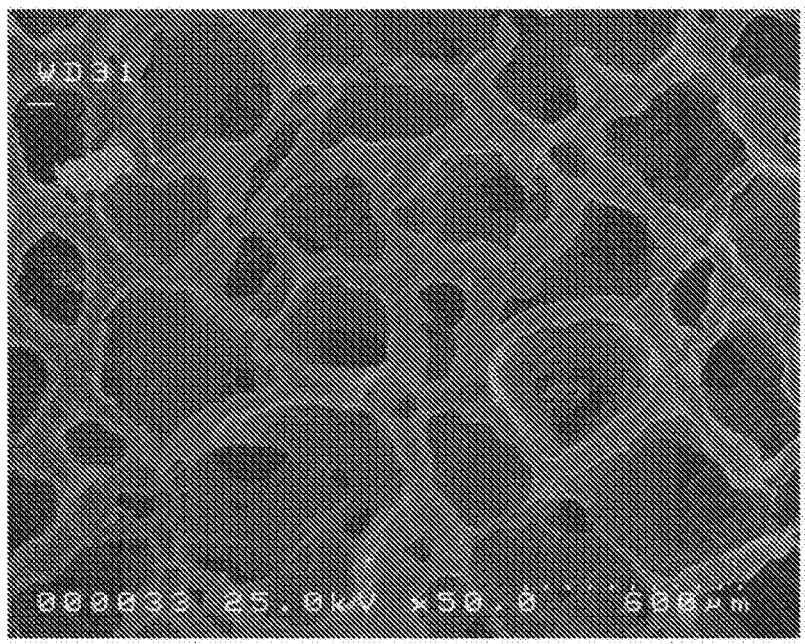
FIGS. 6A and 6B show an analysis of a porous material as disclosed in the present specification.
Figure 6B:
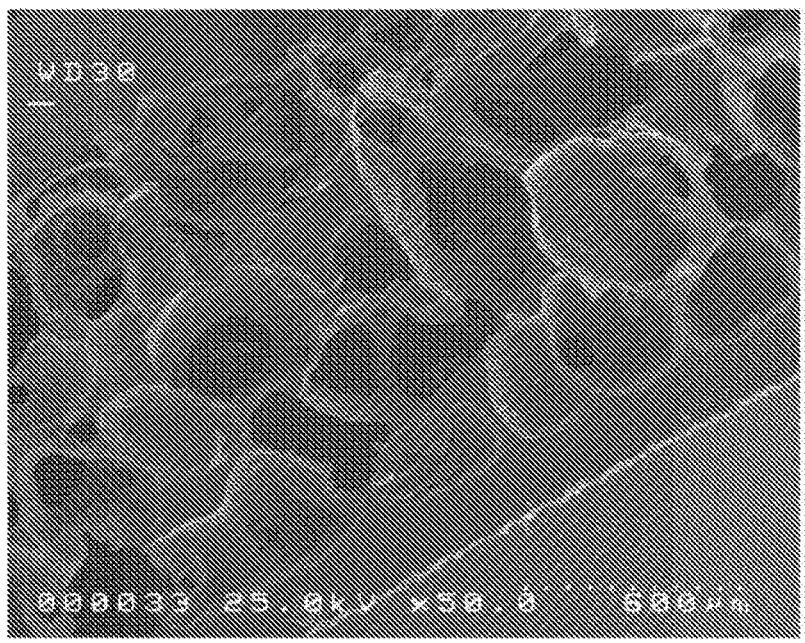

A sample from the implant was characterized by microCT analysis. This analysis revealed that the porous material was about 1.0 mm to about 3.0 mm in thickness with a porosity of about 85%, with open pores comprising at least 80% and close pores comprising at most 10%. The mean strut thickness was about 90 µm, with a mean pore size of about 400 µm. The porous material has a compressive modulus of about 20 kPa, elongation at break of about 300%, and a tensile strength of about 14 µPa. Scanning electron analysis of the porous material is shown in FIG. 6.

Example 8

A Method of Making an Implant Comprising a Porous Material

This example illustrates how to make an implant comprising a porous material of about 2.5 mm to about 4.5 mm in thickness formed using the porogen compositions disclosed herein.

A mandrel comprising a base layer of elastomer was prepared as described in Example 6 or a previously made biocompatible implantable device, such as, e.g., a base shell disclosed herein, can be attached to the mandrel as described in Example 6 and then processed beginning with the next step.

To coat the base layer with a mixture comprising a substance and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 µm and a polyethylene glycol shell of about 53 µm until the maximum amount of porogens were absorbed into the uncured silicone. In other experiments, the porogen composition used were porogens comprising a sugar core of about 335 µm and a polyethylene glycol shell of about 60 µm, porogens comprising a sugar core of about 390 µm and a polyethylene glycol shell of about 83 µm, or porogens comprising a sugar core of about 460 µm and a polyethylene glycol shell of about 104 µm. The mandrel with the uncured silicon/PGLA coating was air dried for about 60 minutes to allow the xylene to evaporate. After xylene evaporation, the mandrel coated with the uncured silicone/porogen mixture was dipped first in about 35% (w/w) silicone in xylene, air dried to allow xylene evaporation (about 3 minutes), and then dipped in the porogen composition until the maximum amount of porogens were absorbed into the uncured silicone. The mandrel with the second coating of uncured silicone/porogen mixture was air dried for about 60 minutes to allow the xylene to evaporate. After xylene evaporation, the mandrel coated with the two layers of the uncured silicone/porogen mixture was dipped first in about 32% (w/w) silicone in xylene, air dried to allow xylene evaporation (about 3 minutes), and then dipped in the porogen composition until the maximum amount of porogens were absorbed into the uncured silicone. The mandrel with the third coating of uncured silicone/porogen mixture was air dried for about 60 minutes to allow the xylene to evaporate.

The mandrel comprising the three coats of uncured silicone/porogen mixture was treating as described in Example 6.

Removal of the porogen scaffold was as described in Example 5, and the resulting implant comprising a porous material of about 2.5 mm to about 4.5 mm was air dried at an ambient temperature of about 18° C. to about 22° C. This process resulted in a biocompatible implantable device comprising a porous material as disclosed herein. See, e.g., FIG. 2 and FIG. 4.

Figure 7A:
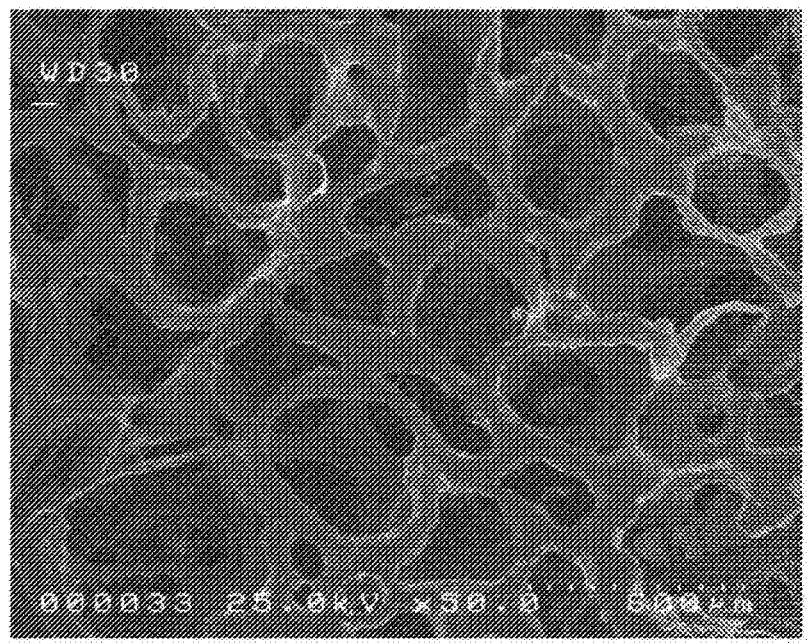
FIGS. 7A and 7B show an analysis of a porous material as disclosed in the present specification.
Figure 7B:
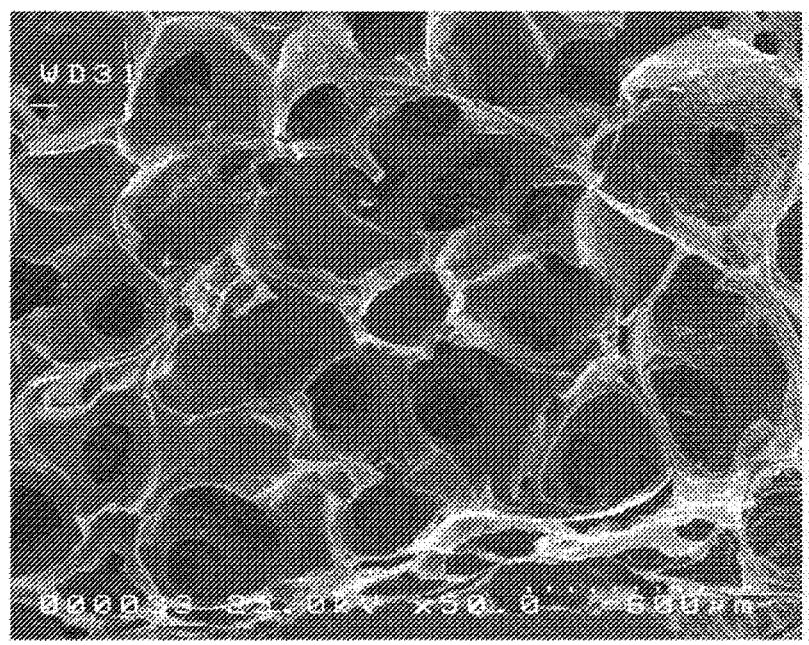

A sample from the implant was characterized by microCT analysis. This analysis revealed that the porous material was about 2.0 mm to about 3.0 mm in thickness with a porosity of about 80%, with open pores comprising at least 75% and close pores comprising at most 25%. The mean strut thickness was about 100 µm, with a mean pore size of about 90 µm. Scanning electron analysis of the porous material is shown in FIG. 7.

Example 9

A Method of Making an Implant Comprising a Porous Material

This example illustrates how to make an implant comprising a porous material of about 3.5 mm to about 5.5 mm in thickness formed using the porogen compositions disclosed herein.

A mandrel comprising a base layer of elastomer was prepared as described in Example 6 or a previously made biocompatible implantable device, such as, e.g., a base shell disclosed herein, can be attached to the mandrel as described in Example 6 and then processed beginning with the next step.

To coat the base layer with a mixture comprising a substance and porogens, the cured base layer was dipped first in about 35% (w/w) silicone in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 µm and a polyethylene glycol shell of about 53 µm until the maximum amount of porogens were absorbed into the uncured silicone. In other experiments, the porogen composition used were porogens comprising a sugar core of about 335 µm and a polyethylene glycol shell of about 60 µm, porogens comprising a sugar core of about 390 µm and a polyethylene glycol shell of about 80 µm, or porogens comprising a sugar core of about 460 µm and a polyethylene glycol shell of about 104 µm. The mandrel with the uncured silicone/porogen mixture coating was air dried for about 60 minutes to allow the xylene to evaporate. After xylene evaporation, the mandrel coated with the uncured silicone/porogen mixture was dipped first in about 35% (w/w) silicone in xylene, air dried to allow xylene evaporation (about 3 minutes), and then dipped in the porogen composition until the maximum amount of porogens were absorbed into the uncured silicone. The mandrel with the second coating of uncured silicone/porogen mixture was air dried for about 60 minutes to allow the xylene to evaporate. After xylene evaporation, the mandrel coated with the two layers of the uncured silicone/porogen mixture was dipped first in about 32% (w/w) silicone in xylene, air dried to allow xylene evaporation (about 3 minutes), and then dipped in the porogen composition until the maximum amount of porogens were absorbed into the uncured silicone. The mandrel with the third coating of uncured silicone/porogen mixture was air dried for about 60 minutes to allow the xylene to evaporate. After xylene evaporation, the mandrel coated with the three layers of the uncured silicone/porogen mixture was dipped first in about 28% (w/w) silicone in xylene, air dried to allow xylene evaporation (about 3 minutes), and then dipped in the porogen composition until the maximum amount of porogens were absorbed into the uncured silicone. The mandrel with the fourth coating of uncured silicone/porogen mixture was air dried for about 60 minutes to allow the xylene to evaporate.

The mandrel comprising the four coats of uncured silicone/porogen mixture was treating as described in Example 6.

Removal of the porogen scaffold was as described in Example 5, and the resulting implant comprising a porous material of about 3.5 mm to about 5.5 mm was dried in an oven of about 126° C. for 30 minutes. This process resulted in a biocompatible implantable device comprising a porous material as disclosed herein. See, e.g., FIG. 2 and FIG. 4.

Figure 8A:
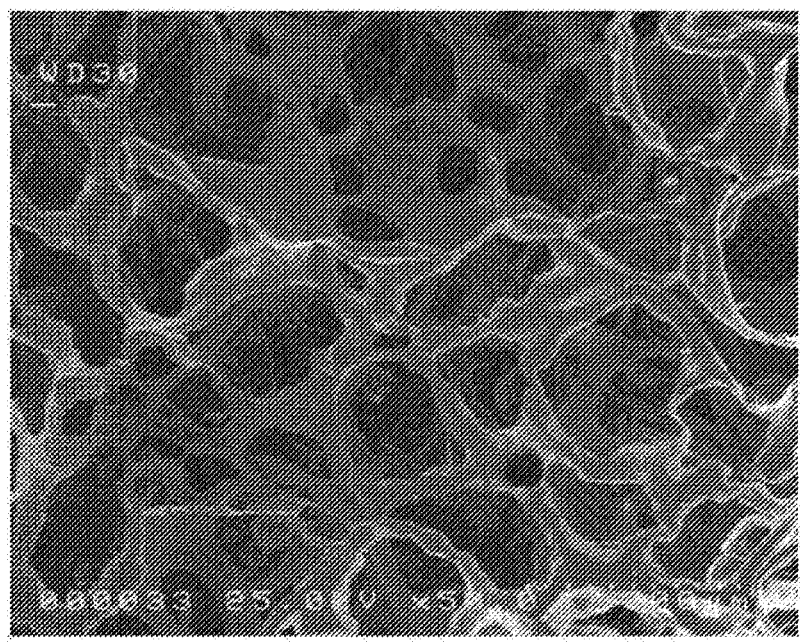
FIGS. 8A and 8B show an analysis of a porous material as disclosed in the present specification.
Figure 8B:
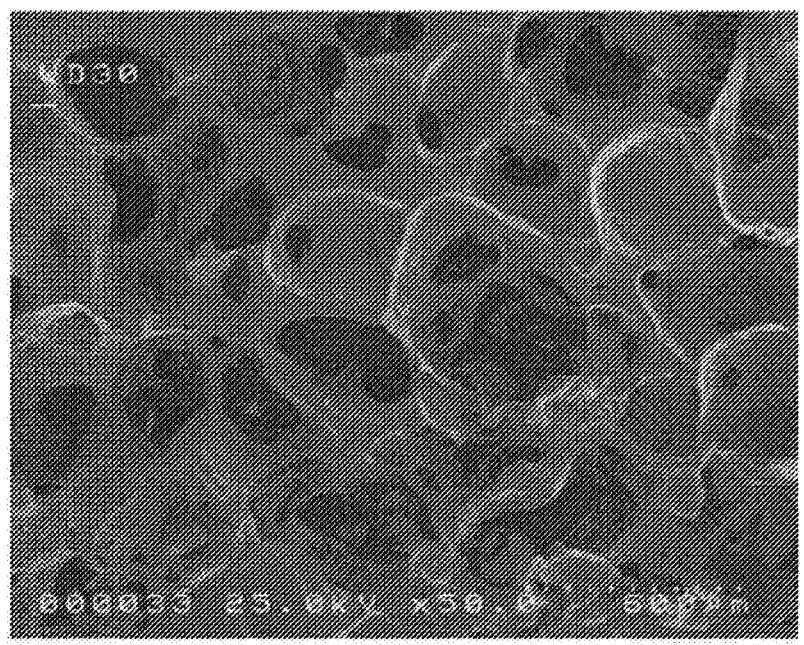

A sample from the implant will be characterized by microCT analysis. Scanning electron analysis of the porous material is shown in FIG. 8.

Example 10

A Method of Making an Implant Comprising a Porous Material

This example illustrates how to make a biocompatible implantable device (an implant) comprising a porous material layer as disclosed herein, wherein the porous material layer is about 2.5 mm to about 4.5 mm in thickness. Except as otherwise indicated, all steps in this Example were conducted at 25° C.

A substance coated porogen mixture was created, the substance in this Example being silicone. To prepare a surface to act as the base for the substance coated porogen mixture, a base layer of 35% (w/w) silicone in xylene (PN-3206-1; NuSil Technology LLC, Carpinteria, Calif.) was coated on a mandrel (LR-10), placed into an oven, and cured at a temperature of 126° C. for 75 minutes. Alternatively, a previously made biocompatible implantable device, such as, e.g., a base shell disclosed herein, can be attached to a mandrel and then processed beginning with the next step.

The cured base layer was then dipped in about 35% (w/w) silicone in xylene (PN-3206-1; NuSil Technology LLC, Carpinteria, Calif.) and air dried for about 18 minutes to about 22 minutes to allow the xylene to evaporate (devolatilization), thus creating a tacky pore coat.

The mandrel with the base layer covered by the tacky pore coat was then dipped in a composition of core/shell porogens until the maximum amount of porogens were absorbed into the uncured silicone, to create a texture bead coat. The core/shell porogens comprised a core of about 450 µm to about 500 µm comprising sucrose and corn starch, and a PEG shell of about 50 µm to about 75 µm in depth, for a mean porogen diameter of about 550 µm. The total composition of the porogens was about 45% sucrose, about 10% starch and about 45% PEG. The texture bead coat (uncured silicone/porogen coating) was then air dried for about 4.5 minutes to about 5.5 minutes to allow for continued devolatilization.

The texture bead coat was then dipped again in silicone as described above to add additional pore coat, and permitted to devolatilize for about 4 minutes to about 5 minutes. The pore coat was then dipped again in porogens as described above to create another layer of texture bead coat, and permitted to devolatilize for about 25 minutes to about 35 minutes. The texture bead coat was then dipped a third time in silicone as described above to create another layer of pore coat, and permitted to devolatilize for about 4 minutes to about 5 minutes. Then the pore coat was dipped in porogens a final time as described above, and permitted to devolatilize for at least 45 minutes. The process resulted in a substance coated porogen mixture having three layers of texture bead (porogen) coat.

To treat the substance coated porogen mixture to allow fusing of the porogens to form a porogen scaffold and to stabilize the substance, the substance coated porogen mixture was placed into an oven at a temperature of about 126° C. for about 85 minutes. This treatment permitted fusion of the PEG shells of the porogens to form a PEG scaffold, followed by stabilization (curing) of the silicone substance. After curing, the shell mold is dismantled and the cured elastomer coated porogen scaffold is removed.

To remove the porogen scaffold, the cured silicone/porogen scaffold was then subjected to more than one repetition of soaking in hot water followed by rinsing in water until all scaffold was dissolved and removed from the substance. In this Example, the substance coated porogen mixture was immersed in hot water (about 60° C.) for about 8 minutes to about 10 minutes, followed by rinsing in water (less than 45° C.). The mixture was then immersed again in hot water (about 60° C.) for about 20 minutes to about 30 minutes, and rinsed again. Finally the substance was immersed one more time in hot water (about 60° C.) for about 20 minutes to about 30 minutes, followed by rinsing in water while massaging (squeezing) the submerged substance about 10 to about 15 times to remove the now dissolved porogen scaffold material.

This process resulted in a biocompatible implantable device comprising an outer porous material layer (or shell) comprising a layer of interconnected pores, as disclosed herein. See, e.g., FIGS. 2 and 4. Because the diameter of the porogens was about 550 µm, the average pore size of the porous material was likewise about 550 µm. A sample from the porous material was characterized by microCT analysis. This analysis revealed that the porous material was about 0.8 mm to about 3.0 mm in thickness, with a porosity of about 85% or more, with a surface openness (pore area/total area) of about 60-75%. The porous material has an elongation at break of ≥450%. Scanning electron microscopy (SEM) analysis of the porous material is shown in FIG. 1.

As an alternative example of creating a biocompatible implantable device comprising a porous material layer, the porous material layer is created separately and then attached to the device. In such example, a first porous material layer is created as described above, and is coated with a thin layer of adhesive, for example silicone, and then placed in the bottom cavity of a mold, adhesive side up. A biocompatible implantable device is then placed on top of the porous material surface coated with the adhesive. A second porous material layer is then coated with a thin layer of adhesive such as silicone and applied to the uncovered surface of the biocompatible implantable device. The top piece of the mold cavity is then fixed in place, pressing the two porous material sheets together to create a uniform interface. The silicone adhesive is allowed to cure by placing the covered device into an oven and heated at a temperature of 126° C. for 75 minutes. After curing, excess material is trimmed off creating a uniform seam around the biocompatible implantable device. This process results in a biocompatible implantable device comprising a porous material as disclosed herein.

Alternatively, the porous material created as described above can be laminated onto a biocompatible implantable device while the device is still on a mandrel. In this process, a first porous material layer is coated with a thin layer of silicone and then draped over the device on the mandrel in such a way that there are no wrinkles on the surface. After curing the silicone adhesive, as described above, another coating of silicone is applied to the uncovered surface of the biocompatible implantable device and a second porous material layer is stretched up to cover the back of the device.

After curing the silicone adhesive, as described above, the biocompatible implantable device is then taken off the mandrel and the excess porous material is trimmed to create a uniform seam around the device. This process results in a biocompatible implantable device comprising a porous material as disclosed herein. See, e.g., FIGS. 2 and 4.

Example 11

A Method of Making a Porogen Composition

This example illustrates how to make porogen compositions disclosed herein.

To make a porogen composition comprising a sugar core material and a polymer shell material, sugar particles suitable for a core material were purchased from Paular Corp, (Cranbury, N. J.). These sugar particles were sieved through an about 40 to about 60 mesh to separate particles of about 250 µm to about 450 µm in size. To coat sugar core particles with a polymer, poly(ethylene glycol) was coated onto the sugar core material to a thickness of about 53 µm by fluidization using a fluid bed dryer. The resulting porogen compositions yielded porogens comprising a sugar core material of about 335 µm in diameter and a poly(ethylene glycol) shell material of about 53 µm in thickness.

To make a porogen composition comprising a polymer core material and a wax shell material, a polycaprolactone (PCL) core material will be made using a solvent evaporation process. Briefly, about 500 mL of a 30% (w/v) solution of PCL in dichloromethane will be poured into 3 L of a 6% (w/v) solution of poly(vinyl alcohol), MW 23000, with constant stirring. The mixture will be continuously stirred for enough time to allow methylene chloride to evaporate. The resulting PCL particles of core material will be filtered to remove debris and then will be washed with deionized water to remove the poly(vinyl alcohol). This process will result in about 100 g of PCL particles of core material with a mean diameter of about 400 µm to about 500 µm. To coat polymer core particles with a wax, paraffin will be coated onto the PCL core material to a thickness of about 50 µm by fluidization using a fluid bed dryer. The resulting porogen compositions will yield porogens comprising a polymer core material of about 450 µm in diameter and a paraffin shell material of about 50 µm in thickness.

To make a porogen composition comprising a salt core material and a surfactant shell material, sodium chloride particles suitable for a core material will be purchased from a commercial supplier. These salt particles will be sieved through an about 40 to about 60 mesh to separate particles of about 250 µm to about 450 µm in size. To coat salt core particles with a surfactant, polysorbate 20 will be coated onto the salt core material to a thickness of about 15 µm by fluidization using a fluid bed dryer. The resulting porogen compositions will yield porogens comprising a salt core material of about 350 µm in diameter and a polysorbate 20 shell material of about 15 µm in thickness.

To make a porogen composition comprising a PGLA (50:50) core and a PCL shell material, PGLA (50:50) and polycaprolactone (PCL) were co-dissolved in methylene chloride, where at least 2 parts of PGLA (50:50) and at most at 1 part of PCL were dissolved in methylene chloride. Solvent evaporation was applied to form microparticles. A PGLA (50:50) core with PCL shell was formed by annealing the microparticles at 60° C. to allow phase separation between PGLA and PCL. About 500 mL of a 30% (w/v) solution of PGLA (50:50) and PCL in dichloromethane was poured into 3 L of a 6% (w/v) solution of poly(vinyl alcohol), MW 23000, with constant stirring until the methylene chloride evaporated. The resulting particles in polyvinyl alcohol dispersions were heated at 60° C. to allow phase separation between PGLA (50:50) and PCL. After cooling down, the microparticles were filtered to remove debris and then washed with deionized water to remove the poly(vinyl alcohol). This process resulted in about 100 g of a PGLA (50:50) core and PCL shell composition with a mean diameter of about 400 µm to about 500 µm.

Example 12

A Method of Making a Porogen Composition

This example illustrates how to make porogen compositions disclosed herein.

To make a porogen composition comprising a sugar core material comprising two compounds and a polymer shell material, sugar particles suitable for a core material were purchased from Paular Corp. (#703540 MESH 35-40; Cranbury, N.J.), comprising about 75% sucrose with about 25% corn starch binder. To coat sugar core particles with a polymer, poly(ethylene glycol) (PEG with a molecular weight=8000 nominal (PEG 8000)) was coated onto the sugar core material to a thickness of about 50 µm by fluidization using a fluid bed dryer. The total composition of the porogens in this Example was about 45% sucrose, about 10% starch and about 45% PEG. The resulting porogen compositions yielded porogens comprising a sugar core material of about 420-500 µm in diameter and a PEG shell material of about 50 µm in thickness. Particles were sieved through an about 35 US mesh to separate particles of about 500 µm to about 550 µm in size.

Example 13

Capsule Thickness and Disorganization

In order to measure the thickness and disorganization of capsules formed, disks (1 cm in diameter) of various porous biomaterials were implanted subcutaneously in Sprague-Dawley rats using standard procedures. The biomaterials tested were taken from commercially available implants or experimentally produced as follows: Smooth 1, a biomaterial having a smooth surface (NATRELLE®, Allergan, Inc., Irvine, Calif.); Smooth 2, a biomaterial having a smooth surface (MEMORYGEL®, Mentor, Inc., Santa Barbara, Calif.); Textured 1, a biomaterial having a closed-cell textured surface produced from a lost-salt method (BIOCELL®, Allergan, Inc., Irvine, Calif.); Textured 2, a biomaterial having a closed-cell textured surface produced from an imprinting method (SILTEX®, Mentor, Inc., Santa Barbara, Calif.); Textured 3, a biomaterial having a closed-cell textured surface produced from either an imprinting or gas foam method (SILIMED®, Sientra, Inc., Santa Barbara, Calif.); Textured 4, a biomaterial having a closed-cell textured surface produced from an imprinting method (Perouse Plastie, Mentor, Inc., Santa Barbara, Calif.); Textured 5, a biomaterial having an open-cell polyurethane surface; Textured 6, a biomaterial having an open-cell textured surface produced according to the methods disclosed herein. Samples were harvested at 6 weeks, fixed in formalin, and processed to produce paraffin blocks. The paraffin blocks were sectioned using a microtome at 2 µm thickness and stained with hematoxylin and eosin (H&E).

Capsules were characterized by measuring the thickness and disorganization of the capsule formed over the porous biomaterials. Capsule thickness was measured by acquiring 2 representative 20× images of the H&E stained biomaterials and measuring the thickness of the capsule at 3 points in the image. Capsule disorganization was evaluated by acquiring 3 representative 20× images of the H&E stained biomaterials, and then drawing a reference vector tangent to the implant surface, as well as, drawing vectors along collagen fibers within the capsule. The angle of each vector relative to the reference vector was then measured, and the standard deviation of the angles was calculated, where greater standard deviations reflected a higher degree of disorganization. All image analysis calculations were performed on the Nikon Elements Advanced Research software.

All thickness and disorganization measurements were acquired blinded and each measurement was normalized to the data obtained from Textured 1 biomaterial. For the thickness data collected, a one-way ANOVA was run to determine significant effects ($p<0.05$). If there were any statistically significant effects from the ANOVA analysis, the Tukey's post-hoc test was run for multiple comparisons at $\alpha=0.05$. For the disorganization data collected, a Levene's Test for Equal Variance was used to determine whether there was a statistically significant difference in disorganization between experimental groups ($p<0.05$). Between individual groups, the criteria for non-significance were overlap of confidence intervals (95%), adjusted for the number of groups.

Figure 9A:
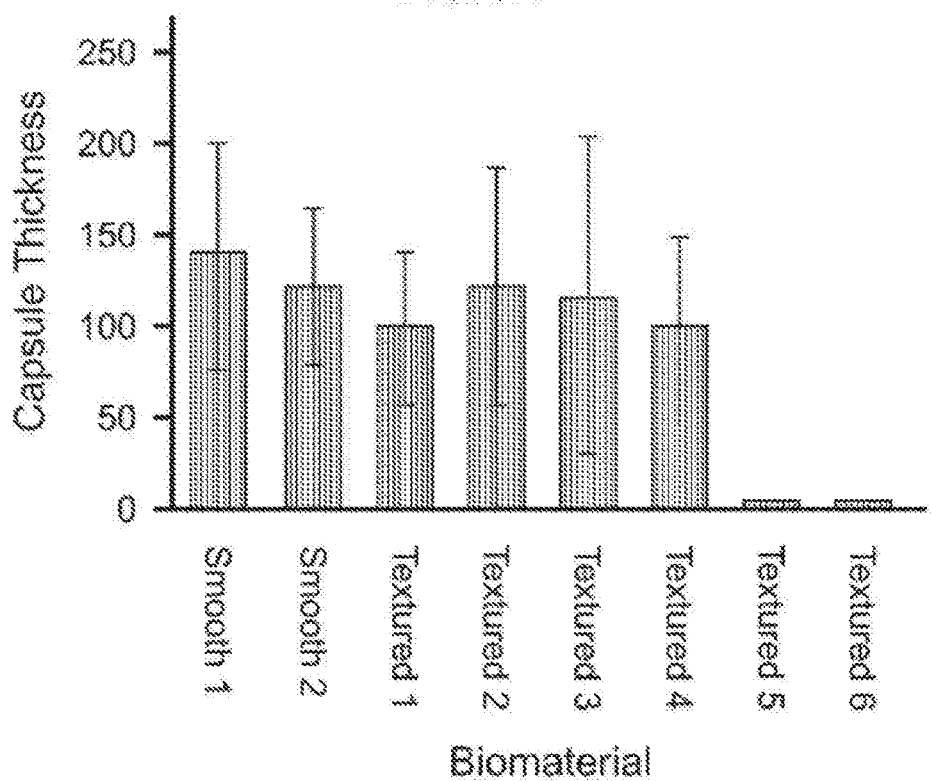
FIGS. 9A and 9B are bar graphs showing data of thickness and disorganization of capsules from various biomaterials, normalized to Textured 1 biomaterial.
Figure 9B:
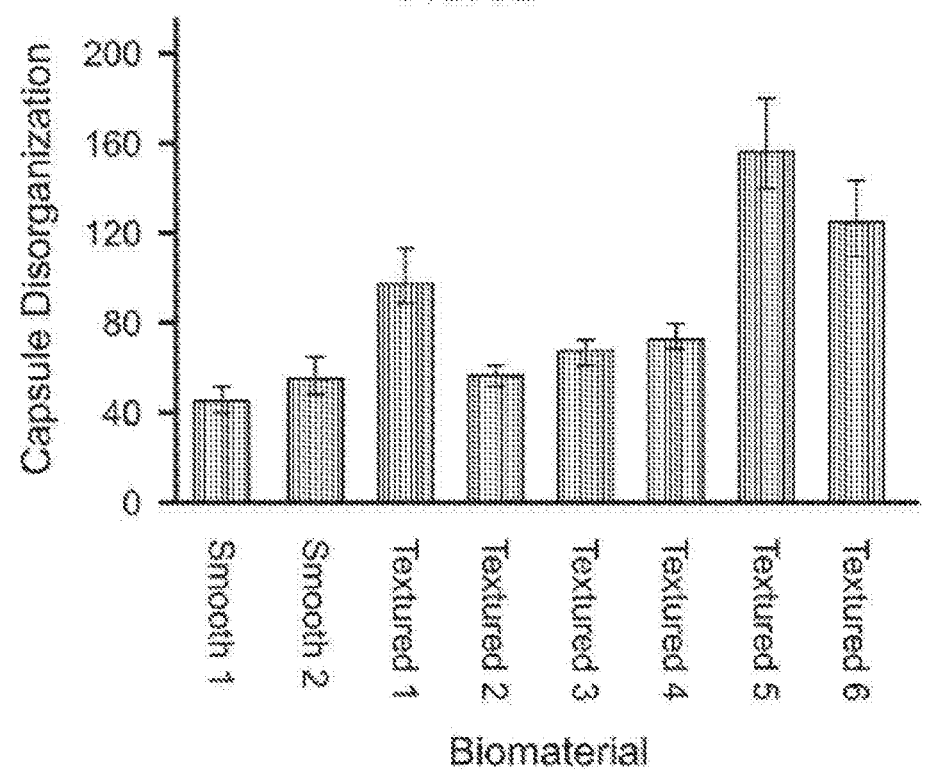

The capsule thicknesses and disorganization, normalized to the Texture 1 biomaterial within each respective study, are shown in FIG. 9. Smooth Texture 1 and 2 biomaterials, and Textures 1-4 biomaterials (having closed-cell texture) exhibited pronounced capsule formation, and the capsules formed were of equivalent thicknesses of about 100 µm to about 140 µm (FIG. 9A). Texture 5-6 biomaterials exhibited minimal capsule formation with capsules formed having a thickness of less than 10 µm (FIG. 9A). With respect to capsule organization, it was found that Texture 1 biomaterial resulted in a capsule that was more disorganized than Smooth 1 and 2 and Texture 2-4 biomaterials (FIG. 9B). Texture 5 and 6 biomaterials demonstrated extensive ingrowth (about 200 µm) that was interconnected and significantly more disorganized (≥50% of fibers were not parallel to implant surface) than Smooth 1 and 2 and Texture 1-4 biomaterials (FIG. 9B). These findings show that Smooth 1 and 2 biomaterials (smooth surface) and Textures 1-4 biomaterials (closed-cell textured surfaces) resulted in a capsule with predominantly organized collagen. Textures 5-6 biomaterials (open-cell textured surfaces), in contrast, induce significant ingrowth that can eliminate capsule and disorganize the tissue at the material-tissue interface.

Example 14

Capsule Collagen

In order to measure the collagen content of capsules formed, disks (1 cm in diameter) of various porous biomaterials were implanted subcutaneously in Sprague-Dawley rats using standard procedures. The biomaterials tested were taken from commercially available implants or experimentally produced as follows: Smooth 1, a biomaterial having a smooth surface (NATRELLE®, Allergan, Inc., Irvine, Calif.); Smooth 2, a biomaterial having a smooth surface (MEMORYGEL®, Mentor, Inc., Santa Barbara, Calif.); Textured 1, a biomaterial having a closed-cell textured surface produced from a lost-salt method (BIOCELL®, Allergan, Inc., Irvine, Calif.); Textured 2, a biomaterial having a closed-cell textured surface produced from an imprinting method (SILTEX®, Mentor, Inc., Santa Barbara, Calif.); Textured 3, a biomaterial having a closed-cell textured surface produced from an imprinting method (Perouse Plastie, Mentor, Inc., Santa Barbara, Calif.); Textured 4, a biomaterial having a closed-cell textured surface produced from either an imprinting or gas foam method (SILIMED®, Sientra, Inc., Santa Barbara, Calif.); Textured 5, a biomaterial having an inverse foam polyurethane-polyethylene glycol surface; Textured 6, a biomaterial having an inverse foam polyurethane-polyethylene glycol surface; Textured 7, a biomaterial having an open-cell polyurethane surface; Textured 8, a biomaterial having a non-woven felt surface. Samples were harvested at 6 weeks, fixed in formalin, and processed to produce paraffin blocks. The paraffin blocks were sectioned using a microtome at 2 μm thickness and stained with aniline blue.

Capsules were characterized by measuring staining darkness of the capsule formed over the implanted porous biomaterials. The darkness of the capsule was measured from 5 representative 20× images, with overall intensity averaged over the capsules to reflect the depth of staining. To account for variations in parameters, such as section thickness and precise staining times, all measurements were normalized to the intensity measured within the dermis of the same section, which was utilized as a standard due to the consistent staining that was observed in this region. A one-way ANOVA was run to determine significant effects ($p<0.05$). If there were any statistically significant effects from the ANOVA analysis, the Tukey's post-hoc test was run for multiple comparisons at $\alpha=0.05$.

Figure 10:
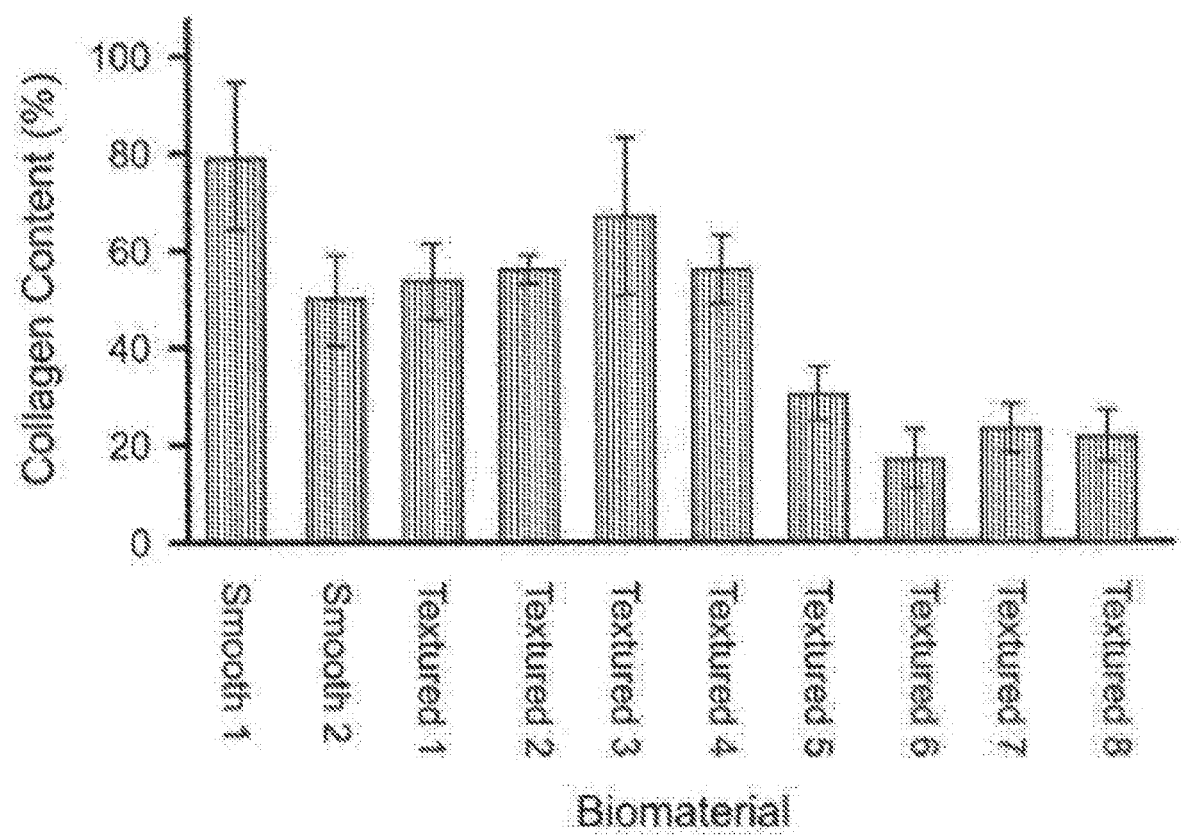
FIG. 10 is bar graph showing data of collagen content of capsules formed over various biomaterials (n=6). Results are shown as mean±standard deviation. Asterisks (*) indicates a statistically significant from Texture 1 biomaterial.

FIG. 10 shows the mean collagen density of capsules and ingrowth formed over smooth and textured biomaterials. It was found that the capsules formed over Smooth 1 and 2 biomaterials and Textured 1-4 biomaterials (closed-cell textured surfaces) showed a statistically significant increase in collagen density over the Texture 5 and 6 biomaterials (inverse foam textured surface), Textured 7 biomaterial (open-cell textured surface), and Textured 8 biomaterial (non-woven felt textured surface). As such, the prevention of capsule formation was shown to be linked to significant ingrowth into an open, interconnected texture, where the ingrowth has a low collagen density.

Example 15

Tissue Adherence

In order to evaluate the effect of texture on tissue adherence to a porous biomaterials, strips of various biomaterial were implanted subcutaneously in a Sprague-Dawley rat using standard procedures. The biomaterials tested were taken from commercially available implants or experimentally produced as follows: Smooth 1, n=38, a biomaterial having a smooth surface (NATRELLE®, Allergan, Inc., Irvine, Calif.); Textured 1, n=64, a biomaterial having a closed-cell textured surface produced from a lost-salt method (BIOCELL®, Allergan, Inc., Irvine, Calif.); Textured 2, n=6, a biomaterial having a closed-cell textured surface produced from an imprinting method (SILTEX®, Mentor, Inc., Santa Barbara, Calif.); Textured 3, n=6, a biomaterial having an inverse foam polyurethane-polyethylene glycol surface; Textured 4, n=45, a biomaterial having an inverse foam polyurethane-polyethylene glycol surface; Textured 5, n=45, a biomaterial having an open-cell polyurethane surface; Textured 6, n=6, a biomaterial having an open-cell polyurethane surface; Textured 7, n=6, a biomaterial having an open-cell textured surface of 0.8 mm produced according to the methods disclosed herein; Textured 8, n=6, a biomaterial having an open-cell textured surface of 1.5 mm produced according to the methods disclosed herein. Samples were harvested at 4 weeks, and tissue was pulled from the test strip on a mechanical tester with a pullout speed of 2 mm/second. Adherence strength was measured as the peak force required to separate the implant from the surrounding tissue. A one-way ANOVA was run to determine significant effects ($p<0.05$). If there were any statistically significant effects from the ANOVA analysis, the Tukey's post-hoc test was run for multiple comparisons at $\alpha=0.05$.

Figure 11:
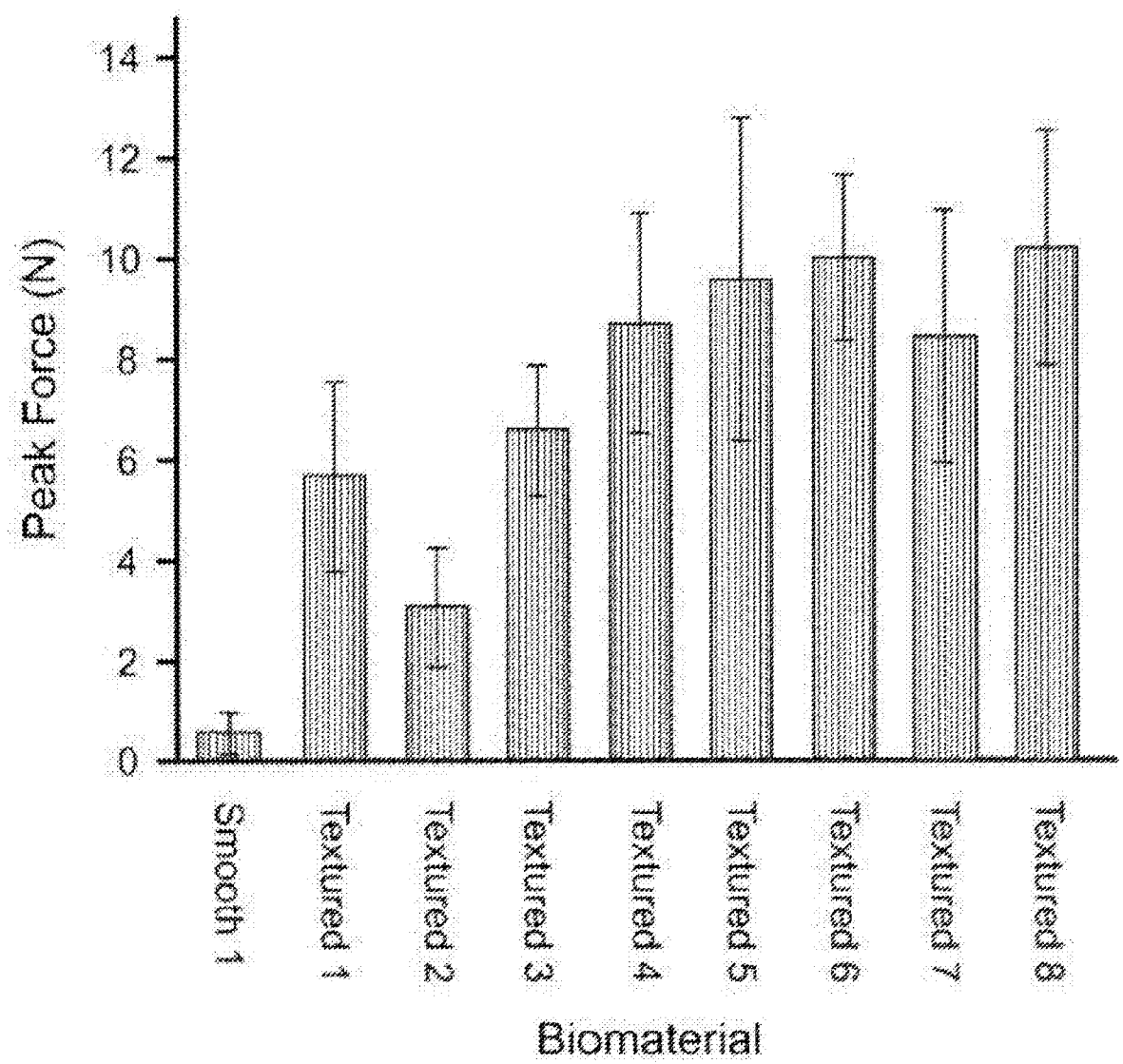
FIG. 11 is a bar graph showing data from a tissue adherence test of various biomaterials. Results are shown as mean±standard deviation.

Smooth 1 biomaterial showed little adherence, as there were no significant protrusions above a micro-scale and had minimal drag on the surrounding tissue (FIG. 11). Textured 1 and 2 biomaterials (closed-cell textured surfaces) exhibited limited amount of tissue interaction and showed greater adherence than Smooth 1 (FIG. 11). Textured 3 and 4 biomaterials (inverse Foam textured surface) and Textures 5-8 biomaterials (open-cell textured surfaces) showed the highest degree of tissue adherence (FIG. 11). As such, Textured 5-8 biomaterials promoted significant tissue infiltration/ingrowth because of the highly porous and interconnected textures.

Example 16

Capsule Stiffness

In order to evaluate stiffness of capsules/ingrowth formed over a porous biomaterials, 7 mL mini-expanders comprising silicone biomaterial of various textures were implanted subcutaneously in a Sprague-Dawley rat using standard procedures. The biomaterials tested were taken from commercially available implants or experimentally produced as follows: Smooth 1, a biomaterial having a smooth surface (NATRELLE®, Allergan, Inc., Irvine, Calif.); Textured 1, a biomaterial having a closed-cell textured surface produced from a lost-salt method (BIOCELL®, Allergan, Inc., Irvine, Calif.); Textured 2, a biomaterial having an open-cell textured surface of 0.8 mm produced according to the methods disclosed herein; Textured 3, a biomaterial having an open-cell textured surface of 1.5 mm produced according to the methods disclosed herein. At time 0 (immediately post-implantation) and at 6 weeks, saline was incrementally added to each expander, and the resulting pressure exerted on and by the expander at each step was measured with a digital manometer. Stiffness was calculated by fitting a trend-line to the linear region of the pressure-volume curve and measuring the slope of the line. Increases in the stiffness of the capsule/ingrowth were reflected by increases in the slope. To account for expander-to-expander variability, each stiffness measurement was normalized to the stiffness of the expander itself. A one-way ANOVA was run to determine significant effects ($p<0.05$). If there were any statistically significant effects from the ANOVA analysis, the Tukey's post-hoc test was run for multiple comparisons at $\alpha=0.05$.

Figure 12:
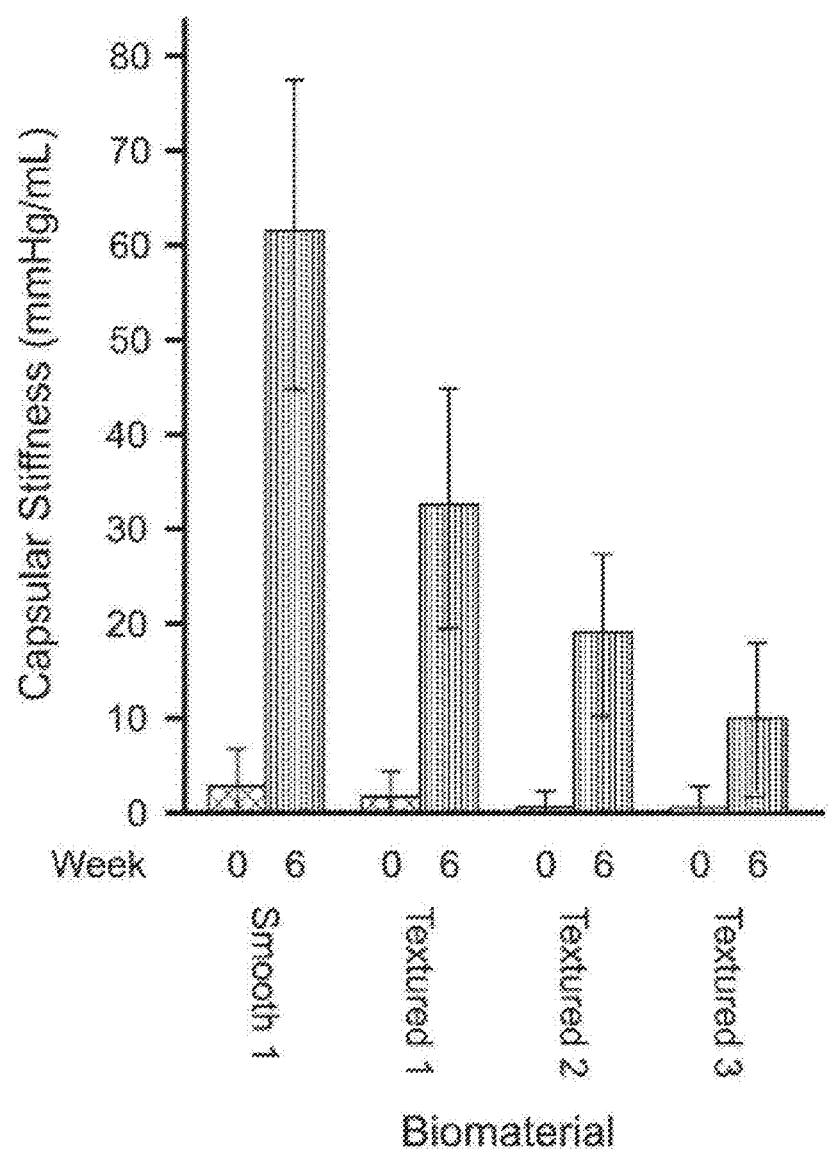
FIG. 12 is bar graph showing data of stiffness of capsule/ingrowth formed over various tissue expanders at time 0 and at 6 weeks (n=8). Results are shown as mean±standard deviation.

Capsules formed over Smooth 1 biomaterial expander showed the greatest stiffness after 6 weeks (FIG. 12). Textured 1 biomaterial expander (closed-cell textured surface) showed lower stiffness than Smooth 1 biomaterial expander but greater stiffness than the Textured 2 and 3 biomaterial expanders (open-cell textured surface) (FIG. 12). This data demonstrates that closed-cell biomaterials result in capsules that are stiffer than those that result from open-cell biomaterials that support ingrowth and prevent capsule formation.

Example 17

Capsule Response

In order to identify critical morphological and physical characteristics of the porous biomaterials disclosed herein, disks (1 cm in diameter) of various biomaterials were implanted subcutaneously in a Sprague-Dawley rat using standard procedures and the response to such implantation in terms of capsule formation was determined. The morphological and physical characteristics tested for each biomaterial are given in Tables 1 and 2.

TABLE 1

Morphological Characteristics of Biomaterials

| Biomaterial | Mean thickness (mm) | Mean porosity (%) | Mean pore size (µm) | Mean interconnections/pore | Mean interconnection size (µm) |
|---|---|---|---|---|---|
| Polyurethane 1 | 2.40 ± 0.10 | 98.0 ± 0.4 | 522 ± 87 | 14.2 ± 3.2 | 166 ± 48 |
| Polyurethane 2 | 2.90 ± 0.01 | 98.0 ± 0.0 | 488 ± 119 | 14.2 ± 1.4 | 230 ± 69 |
| Mesh 1 | 0.89 ± 0.06 | 72.2 ± 1.5 | 522 ± 137 | N/A | N/A |
| Mesh 2 | 1.38 ± 0.10 | 70.9 ± 2.9 | 560 ± 134 | N/A | N/A |
| Fused Porogen 1 | 0.56 ± 0.38 | 55.6 ± 0.5 | 530 ± 150 | 7.0 ± 3.1 | 325 ± 242 |
| Fused Porogen 2 | 0.79 ± 0.06 | 72.6 ± 5.4 | 458 ± 48 | 7.8 ± 1.5 | 151 ± 59 |
| Fused Porogen 3 | 1.10 ± 0.00 | 77.6 ± 1.0 | 596 ± 150 | 4.6 ± 1.9 | 106 ± 42 |
| Fused Porogen 4 | 1.14 ± 0.09 | 66.4 ± 3.2 | 424 ± 68 | 8.0 ± 1.1 | 111 ± 49 |
| Fused Porogen 5 | 1.32 ± 0.02 | 77.9 ± 0.9 | 408 ± 64 | 7.6 ± 2.0 | 118 ± 44 |
| Fused Porogen 6 | 1.60 ± 0.10 | 77.8 ± 1.2 | N/D | N/D | N/D |
| Fused Porogen 7 | 1.60 ± 0.10 | 81.2 ± 1.3 | 608 ± 268 | 4.9 ± 1.9 | 130 ± 85 |
| Fused Porogen 8 | 1.60 ± 0.00 | 85.3 ± 1.4 | 421 ± 48 | 8.2 ± 2.1 | 128 ± 38 |
| Fused Porogen 9 | 1.61 ± 0.03 | 80.3 ± 1.0 | 456 ± 81 | 7.4 ± 1.6 | 154 ± 50 |
| Fused Porogen 10 | 1.80 ± 1.20 | 80.6 ± 0.4 | 634 ± 124 | 7.5 ± 2.6 | 95 ± 33 |
| Fused Porogen 11 | 1.93 ± 0.78 | 82.8 ± 0.5 | 456 ± 65 | 7.1 ± 2.2 | 133 ± 46 |
| Fused Porogen 12 | 1.95 ± 0.19 | 76.5 ± 2.0 | 431 ± 57 | 7.0 ± 1.2 | 114 ± 58 |
| Fused Porogen 13 | 2.34 ± 0.06 | 74.0 ± 0.5 | 478 ± 112 | 7.1 ± 2.0 | 141 ± 47 |
| Fused Porogen 14 | 2.36 ± 0.12 | 81.1 ± 0.5 | 399 ± 93 | 7.4 ± 0.8 | 126 ± 64 |

TABLE 2

Physical Characteristics of Biomaterials

| Biomaterial | Compressive Response (kPa) | | | Elongation at Break (%) |
|---|---|---|---|---|
| | at 5% strain | at 10% strain | at 20% strain | |
| Polyurethane 1 | 1.74 ± 0.40 | 2.60 ± 0.53 | 3.38 ± 0.52 | N/D |
| Polyurethane 2 | 1.41 ± 0.13 | 2.63 ± 0.03 | 2.89 ± 0.20 | 454 ± 7 |
| Mesh 1 | 0.07 ± 0.01 | 0.20 ± 0.02 | 0.74 ± 0.08 | 336 ± 39 |
| Mesh 2 | 0.09 ± 0.04 | 0.22 ± 0.09 | 0.74 ± 0.39 | 439 ± 56 |
| Fused Porogen 1 | 0.05 ± 0.00 | 0.18 ± 0.01 | 1.01 ± 0.14 | N/D |
| Fused Porogen 2 | 0.05 ± 0.03 | 0.23 ± 0.10 | 1.59 ± 0.46 | N/D |
| Fused Porogen 3 | 0.04 ± 0.01 | 0.14 ± 0.06 | 0.86 ± 0.36 | N/D |
| Fused Porogen 4 | 0.55 ± 0.21 | 1.55 ± 0.50 | 5.21 ± 1.18 | 287 ± 78 |
| Fused Porogen 5 | 0.13 ± 0.02 | 0.59 ± 0.14 | 3.26 ± 0.64 | N/D |
| Fused Porogen 6 | 0.10 ± 0.02 | 0.38 ± 0.11 | 2.24 ± 0.92 | N/D |
| Fused Porogen 7 | 0.094 ± 0.00 | 0.35 ± 0.06 | 1.86 ± 0.36 | N/D |
| Fused Porogen 8 | 0.04 ± 0.01 | 0.15 ± 0.04 | 0.61 ± 0.13 | 222 ± 33 |
| Fused Porogen 9 | 0.11 ± 0.03 | 0.46 ± 0.12 | 2.00 ± 0.26 | N/D |
| Fused Porogen 10 | 0.14 ± 0.01 | 0.43 ± 0.03 | 1.48 ± 0.01 | N/D |
| Fused Porogen 11 | 0.17 ± 0.00 | 0.64 ± 0.01 | 2.15 ± 0.03 | N/D |
| Fused Porogen 12 | 0.42 ± 0.14 | 1.07 ± 0.29 | 3.17 ± 0.61 | 384 ± 20 |
| Fused Porogen 13 | 0.19 ± 0.04 | 0.84 ± 0.16 | 3.48 ± 0.39 | N/D |
| Fused Porogen 14 | 0.06 ± 0.02 | 0.16 ± 0.06 | 0.61 ± 0.10 | 335 ± 11 |

Implanted porous biomaterials were harvested, fixed in formalin, and processed to produce paraffin blocks. The paraffin blocks were sectioned using a microtome at 2 µm thickness and stained with hematoxylin and eosin (H&E). Depending on the morphological characteristic being assessed, capsule response was measured by acquiring at least 3 representative 1×, 4×, 20×, or 50× images of sectioned biomaterial, digitally capturing the images, and measuring the characteristic at 3 or more point in each captured image. All image analysis calculations were performed on the Nikon Elements Advanced Research software. Physical characteristics were measured using routine methods. See, e.g., Winnie, Softness Measurements for Open-Cell Foam Materials and Human Soft Tissue, Measurement Science and Technology (2006).

TMore strikingly, increasing the number of interconnections per pore decreased capsule formation seen in the animals in response to the implanted porous biomaterials (Table 3). Lastly, a fine balance in the stiffness of a porous biomaterial, as measured by compressive forces, was needed to provide the optimal in vivo responses.

TABLE 3

Capsule Response of Biomaterials

| Characteristic | Capsule Response | |
|---|---|---|
| | No Capsule | Capsule |
| Mean thickness (mm) | 0.8-2.9 | 0.6-2.9 |
| Mean porosity (%) | 72-98 | 56-81 |
| Mean pore size (μm) | 456-641 | 408-634 |
| Mean interconnections/pore | 7.1-14 | 4.6-9.5 |
| Mean interconnection size (μm) | 456-641 | 408-634 |
| Compressive at 5% strain (kPa) | 0.05-1.70 | 0.00-2.57 |
| Compressive at 10% strain (kPa) | 0.22-4.17 | 0.10-8.00 |
| Compressive at 20% strain (kPa) | 1.10-7.60 | 0.90-16.0 |

Analyzing all the data obtained from these experiments revealed optimal morphological and physical characteristics for a porous material produced from the porogen method disclosed herein, was as follows: having a porosity of about 80% to about 88%, having an interconnection size of about 110 μm to about 140 μm, having about 7 to about 11 interconnections per pore, having a compressive force of about 0.50 kPa to about 0.70 kPa at 5% strain, having a compressive force of about 1.0 kPa to about 2.0 kPa at 10% strain, and having a compressive force of about 3.5 kPa to about 5.5 kPa at 20% strain. In an aspect of this embodiment, optimal morphological and physical characteristics for a porous material produced from the porogen method disclosed herein, was as follows: having a porosity of about 83% to about 85%, having an interconnection size of about 120 μm to about 130 μm, having about 8 to about 10 interconnections per pore, having a compressive force of about 0.55 kPa to about 0.65 kPa at 5% strain, having a compressive force of about 1.3 kPa to about 1.7 kPa at 10% strain, and having a compressive force of about 4.0 kPa to about 5.0 kPa at 20% strain.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. An uncured elastomer/porogen mixture comprising an elastomer and a porogen composition for coating a biocompatible implantable device comprising a porous material formed using the porogen composition, the porogen composition comprising a core material and a shell material, wherein the shell material comprises about 40% to 50% polyethylene glycol, by weight, wherein the core material comprises about 35% to about 50% sucrose and about 10% to about 15% starch, by weight, wherein the shell material has a melting temperature that is lower than a melting temperature of the core material, and wherein the shell material is adjacent to the core material.

2. The mixture of claim 1, wherein the core material comprises a sugar or a derivative thereof, a polysaccharide sugar or a derivative thereof, a composite thereof, or a combination thereof.

3. The mixture of claim 1, wherein the porogen composition comprises about 45% sucrose, about 10% starch, and about 45% polyethylene glycol, by weight.

4. The mixture of claim 1, wherein the porogen composition comprises about 40% sucrose, about 15% starch, and about 45% polyethylene glycol, by weight.

5. The mixture of claim 1, wherein the porogen composition comprises a mean porogen diameter of about 300 μm to about 650 μm.

6. The mixture of claim 5, wherein the porogen composition comprises a mean porogen diameter of about 550 μm.

7. An uncured elastomer/porogen mixture comprising an elastomer and a porogen composition for coating a biocompatible implantable device comprising a porous material formed using the porogen composition, the porogen composition comprises a mean porogen diameter of between about 1500 μm and about 3000 μm and a mean roundness of at least 0.1, the porogen composition comprising a core material and a shell material, wherein the core material comprises at least two compounds, wherein under a given physical or physicochemical treatment the shell material transitions from a solid phase to a liquid phase and the core material remains in a solid phase, and wherein the shell material is adjacent to the core material.

8. The mixture of claim 7, wherein under the given physical or physicochemical treatment, shell fusion occurs by a physical state change from solid phase to liquid or rubbery phase.

9. The mixture of claim 7, wherein the shell material comprises at least two compounds.

10. The mixture of claim 7, wherein the core material comprises a sugar or a derivative thereof, a polysaccharide or a derivative thereof, a composite thereof, or a combination thereof.

11. The mixture of claim 7, wherein the core material comprises sucrose and starch.

12. The mixture of claim 7, wherein the shell material comprises polyethylene glycol.

13. The mixture of claim 11, wherein the porogen composition comprises about 35% to about 50% sucrose, about 10% to about 15% starch, and about 40% to 50% polyethylene glycol, by weight.

14. The mixture of claim 13, wherein the porogen composition comprises about 45% sucrose, about 10% starch, and about 45% polyethylene glycol, by weight.

15. The mixture of claim 13, wherein the porogen composition comprises about 40% sucrose, about 15% starch, and about 45% polyethylene glycol, by weight.

16. A biocompatible implantable device formed by a process comprising:
    applying an uncured elastomer/porogen mixture to form a layer of the device, the layer comprising an elastomer and a porogen composition;
    transitioning the layer from a solid phase to a liquid phase under a given physical or physiochemical treatment to fuse porogens of the porogen composition together to form a porogen scaffold; and
    removing the porogen scaffold from the layer under a given physical or physicochemical treatment.

17. The device of claim 16, wherein the porogen composition comprises a shell material and a core material that has a melting temperature that is higher than a melting temperature of the shell material.

18. The device of claim 16, wherein the porogen composition comprises a mean porogen diameter of at least 50 μm.

19. The device of claim 16, wherein the porogen composition comprises a core material and a shell material, wherein the shell material comprises about 40% to 50% polyethylene glycol, by weight, and wherein the core material comprises about 35% to about 50% sucrose and about 10% to about 15% starch, by weight.

\* \* \* \* \*

UNITED STATES PATENT AND TRADEMARK OFFICE
CERTIFICATE OF CORRECTION

PATENT NO. : 11,202,853 B2
APPLICATION NO. : 16/850981
DATED : December 21, 2021
INVENTOR(S) : Futian Liu et al.

It is certified that error appears in the above-identified patent and that said Letters Patent is hereby corrected as shown below:

In the Specification

Column 9, Lines 5 to 6, "hexoaccharides, heptoaccharides, octoaccharides, nonoaccharides, decoaccharides, etc." should read --hexasaccharides, heptasaccharides, octoasaccharides, nonasaccharides, decasaccharides, etc.--.
Column 9, Line 8, "monosacchrides" should read --monosaccharides--.
Column 9, Line 15, "octooses" should read --octoses--.
Column 9, Line 16, "octonate" should read --octanoate--.
Column 9, Line 46, "glcosaminoglycans (like condrotin" should read --glycosaminoglycans (like chondroitin--.
Column 11, Line 6, "dimethyl ammonia" should read --dimethylammonia--.
Column 11, Line 30, "arylic" should read --acrylic--.
Column 11, Line 36, "((like" should read --(like--.
Column 11, Line 39, "(hydroxystrene)," should read --(hydroxystyrene)--.
Column 11, Line 40, "poly(D, L-lactic" should read --poly(D,L-lactic--.
Column 11, Line 49, "oxide)" should read --oxide))--.
Column 11, Line 51, "alcohol," should read --alcohol),--.
Column 36, Line 33, "devolitalized" should read --devolatilized--.
Column 38, Line 48, "fluoro silicone (FVQM)," should read --fluorosilicone (FVMQ),--.
Column 39, Line 18, "devolitalizing" should read --devolatilizing--.
Column 39, Line 20, ""devolitalizing or devitalization"" should read --"devolatilizing or devolatilization"--.
Column 39, Line 22, "Devolitalization" should read --Devolatilization--.
Column 39, Line 26, "devolitalizing" should read --devolatilizing--.
Column 44, Line 67, "form" should read --from--.
Column 45, Line 26, "form" should read --from--.
Column 45, Line 52, "form" should read --from--.
Column 66, Line 33, "mm Hg/m L." should read --mmHg/mL.--.
Column 76, Line 16, "Paular" should read --Paulaur--.
Column 77, Line 15, "Paular" should read --Paulaur--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*

Column 83, Line 4, "TMore" should read --More--.

In the Claims

Column 85, Line 36, Claim 1, "about 40% to 50%" should read --about 40% to about 50%--.
Column 86, Line 28, Claim 13, "about 40% to 50%" should read --about 40% to about 50%--.
Column 86, Line 55, Claim 19, "about 40% to 50%" should read --about 40% to about 50%--.